US011047866B2

(12) United States Patent
Karl et al.

(10) Patent No.: US 11,047,866 B2
(45) Date of Patent: Jun. 29, 2021

(54) IGFBP7 FOR DIAGNOSING DIASTOLIC DYSFUNCTION

(71) Applicant: Roche Diagnostics Operations, Inc., Indianapolis, IN (US)

(72) Inventors: Johann Karl, Peissenberg (DE); Ursula-Henrike Wienhues-Thelen, Krailing (DE); Dirk Block, Bichl (DE); Christian Zaugg, Rheinfelden (CH); Hans-Peter Brunner, Muenchenstein (CH); James Januzzi, Wellesley, MA (US); Andre Ziegler, Laeufelfingen (CH); Julian Braz, Greenwood, IN (US); Thomas Dieterle, Freiburg (DE); Edelgard Kaiser, Huenenberg See (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/420,385

(22) Filed: May 23, 2019

(65) Prior Publication Data

US 2019/0277861 A1 Sep. 12, 2019

Related U.S. Application Data

(60) Division of application No. 15/274,533, filed on Sep. 23, 2016, now Pat. No. 10,345,315, which is a continuation of application No. PCT/EP2015/056418, filed on Mar. 25, 2015.

(30) Foreign Application Priority Data

Mar. 26, 2014 (EP) ..................... 14161732

(51) Int. Cl.
*G01N 33/53* (2006.01)
*G01N 33/68* (2006.01)

(52) U.S. Cl.
CPC ..... *G01N 33/6893* (2013.01); *G01N 33/6887* (2013.01); *G01N 2333/47* (2013.01); *G01N 2800/325* (2013.01)

(58) Field of Classification Search
None
See application file for complete search history.

(56) References Cited

U.S. PATENT DOCUMENTS

| 4,016,043 | A | 4/1977 | Schuurs et al. |
| 4,018,653 | A | 4/1977 | Mennen |
| 4,424,279 | A | 1/1984 | Bohn et al. |
| 5,695,761 | A | 12/1997 | Denhardt et al. |
| 5,736,343 | A * | 4/1998 | Landry ............ G01N 33/5308 435/188.5 |
| 5,744,305 | A | 4/1998 | Fodor et al. |
| 6,414,219 | B1 | 7/2002 | Denhardt et al. |
| 2003/0100010 | A1 * | 5/2003 | Jackowski ......... G01N 33/6851 435/7.1 |
| 2003/0232385 | A1 | 12/2003 | Breit et al. |
| 2007/0266778 | A1 | 11/2007 | Corey et al. |
| 2010/0285491 | A1 | 11/2010 | Wienhues-Thelen et al. |
| 2011/0256155 | A1 | 10/2011 | Huang et al. |

FOREIGN PATENT DOCUMENTS

| EP | 0648228 B1 | 11/1998 |
| WO | 1999/006445 A1 | 2/1999 |
| WO | 2000070051 A1 | 11/2000 |
| WO | 2002/083913 A1 | 10/2002 |
| WO | 2002/089657 A2 | 11/2002 |
| WO | 2005/113585 A2 | 12/2005 |
| WO | 2008/089994 A1 | 7/2008 |
| WO | 2009/047283 A2 | 4/2009 |
| WO | 2010/007041 A1 | 1/2010 |
| WO | 2010/124821 A1 | 11/2010 |
| WO | 2011/012268 A1 | 2/2011 |
| WO | 2012/025355 A1 | 3/2012 |
| WO | 2014/040759 A1 | 3/2014 |
| WO | 2014/043421 A1 | 3/2014 |

OTHER PUBLICATIONS

Torzewski et al., Animal Models of C-Reactive Protein, Hindawl Publishing Corporation, Mediators of Inflammation, vol. 2014, Article ID 683598, 2014, pp. 1-7 (Year: 2014).*
Van Der Vekiens et al., Human and equine cardiovascular endocrinology: beware to compare, Cardiovascular Endocrinology 2013, vol. 2, No. 4, pp. 67-76. (Year: 2013).*
Abdollahi, Amir et al., Endostatin's Antiangiogenic Signaling Network, Molecular Cell, 2004, pp. 649-663, vol. 13.
Akaogi, Kotaro et al., Specific accumulation of tumor-derived adhesion factor in turmor blood vessels and in capillary tube-like structures of cultured vascular endothelial cells, Proceedings of the National Academy of Sciences USA, 1996, pp. 8384-8389, vol. 96.
Ameye, Laurent and Young, Marian F., Mice deficient in small leucine-rich proteoglycans: novel in vivo models for osteoporosis, osteoarthritis, Ehlers-Danlos syndrome, muscular dystrophy, and corneal diseases, Glycobiology, 2002, pp. 107R-116R, vol. 12, No. 9.
Baek, Seung Joon et al., Cyclooxygenase Inhibitors Regulate the Expression of a TGF-β Superfamily Member That Has Proapoptotic and Antitumorigenic Activities, Molecular Pharmacology, 2001, pp. 901-908, vol. 59, No. 4.

(Continued)

*Primary Examiner* — Gary Counts
(74) *Attorney, Agent, or Firm* — Stinson LLP

(57) ABSTRACT

Presented is a method for diagnosing and/or grading diastolic dysfunction or at least one structural or functional abnormality associated with diastolic dysfunction. The method involves measuring the level of IGFBP7 (Insulin like growth factor binding protein 7) and, optionally, the level of at least one further marker in a patient suffering from heart failure, and comparing the level to a reference level. Further envisaged is a method of monitoring diastolic function in a patient suffering from heart failure. Also described are kits and devices adapted to carry out the method.

10 Claims, 13 Drawing Sheets

(56) References Cited

OTHER PUBLICATIONS

Banfi, Giuseppe et al., The role of ethylenediamine tetraacetic acid (EDTA) as in vitro anticoagulant for diagnostic purposes, Clinical Chemistry & Laboratory Medicine, 2007, pp. 565-576, vol. 45, No. 5.

Bauskin, Asne R. et al., The propeptide of macrophage inhibitory cytokine (MIC-1), a TGF-β superfamily member, acts as a quality control determinant for correctly folded MIC-1, The EMBO Journal, 2000, pp. 2212-2220, vol. 19, No. 10.

Bhardwaj, Anju et al., Design and methods of the Pro-B Type Natriuretic Peptide Outpatient Tailored Chronic Heart Failure Therapy (PROTECT) Study, American Heart Journal, 2010, pp. 532-538.e.1, vol. 159, No. 4.

Bootcov, Michelle R. et al., MIC-1, a novel macrophase inhibitory cytokine, is a divergent member of the TGF-β superfamily, Proceedings of the National Academy of Sciences USA, 1997, pp. 11514-11519, vol. 94.

Brown, David A. et al., Concentration in plasma of macrophage inhibitory cytokine-1 and risk of cardiovascular events in women: a nested case-control study, Lancet, 2002, pp. 2159-2163, vol. 359.

Burger, Angelika M. et al., Down-regulation of T1A12/mac25, a novel insulin-like growth factor binding protein related gene, is associated with disease progression in breast carcinomas, Oncogene, 1998, pp. 2459-2467, vol. 15.

Bursi, Francesca et al., Systolic and Diastolic Heart Failure in the Community, JAMA, 2006, pp. 2209-2216, vol. 296, No. 18.

Böttner, Martina et al., Characterization of the rat, mouse, and human genes of growth/differentiation factor-15/macrophage inhibiting cytokine-1 (GDF-15/MIC-1), Gene, 1999, pp. 105-111, vol. 237.

Chen, Doug et al., Insulin-like Growth Factor-Binding Protein-7 Functions as a Potential Tumor Suppressor in Hepatocellular Carcinoma, Clinical Cancer Research, 2011, pp. 6693-6701, vol. 17, No. 21.

Chugh, Shaan et al., Pilot study identifying myosin heavy chain 7, desmin, insulin-like growth factor 7, and annexin A2 as circulating biomarkers of human heart failure, Proteomics, 2013, pp. 2324-2334, vol. 13.

Daniels, Lori B. and Maisel, Alan S., Natriuretic Peptides, Journal of the American College of Cardiology, 2007, pp. 2357-2368, vol. 50, No. 25.

Definition of "serum", Taber's Cyclopedic Medical Dictionary, 1993, p. 1786, 17th Edition.

Denhardt, David T. and Guo, Xiaojia, Osteopontin: a protein with diverse functions, FASEB Journal, 1993, pp. 1475-1482, vol. 7.

Dinh, W. et al., P1288-Serum insulin like growth factor-I and its binding protein-7; novel promising biomarker in heart failure with preserved ejection fraction, Clinical Research in Cardiology, 2012, 1 page, Supplement 1.

Drazner, Mark H. et al., Left Ventricular Hypertrophy is More Prevalent in Blacks Than Whites in the General Population the Dallas Heart Study, Hypertension, 2005, pp. 124-129, vol. 46.

Evdokimova, Valentina et al., IGFBP7 Binds to the IGF-1 Receptor and Blocks Its Activation by Insulin-Like Growth Factors, Science Signaling, 2012, 11 pps., vol. 5, Issue 225 ra92.

Fonarow, Gregg C. et al., Usefulness of B-Type Natriuretic Peptide and Cardiac Troponin Levels to Predict In-Hospital Mortality from ADHERE, American Journal of Cardiology, 2008, pp. 231-237, vol. 101.

Gandhi, Parul U. et al., Prognostic Usefulness of Insulin-Like Growth Factor-Binding Protein 7 in Heart Failure With Reduced Ejection Fraction: A Novel Biomarker of Myocardial Diastolic Function?, American Journal of Cardiology, 2014, pp. 1543-1549, vol. 114.

Giachelli, Cecilia M. et al., Molecular and Cellular Biology of Osteopontin, Trends in Cardiovascular Medicine, 1995, pp. 88-95, vol. 5, No. 3.

Hammerer-Lercher, Angelika et al, Analysis of Circulating Forms of proBNP and NT-proBNP in Patients with Severe Heart Failure, Clinical Chemistry, 2008, pp. 858-865, vol. 54, No. 5.

Hromas, Robert et al., PLAB, a novel placental bone morphogenetic protein, Biochimica et Biophysica Acta, 1997, pp. 40-44, vol. 1354.

Hunt, Sharon A. et al., ACC/AHA Guidelines for the Evaluation and Management of Chronic Heart Failure in the Adult: Executive Summary, Journal of the American College of Cardiology, 2001, pp. 2101-2113, vol. 38, No. 7.

Hunt, Sharon Ann et al., ACC/AHA 2005 Guideline Update for the Diagnosis and Management of Chronic Heart Failure in the Adult, Journal of the American College of Cardiology, 2005, pp. e1-e82, vol. 46.

Hwa, Vivian et al., The Insulin-Like Growth Factor-Binding Protein (IGFBP) Superfamily, Endocrine Reviews, 1999, pp. 761-787, vol. 20, No. 6.

International Search Report dated Jul. 14, 2015, in Application No. PCT/EP2015/056418, 6 pages.

Irby, R. B. et al., Osteopontin regulates multiple functions contributing to human colon cancer development and progression, Clinical & Experimental Metastasis, 2004, pp. 515-523, vol. 21.

Januzzi, James L., Jr. et al., The N-Terminal Pro-BNP Investigation of Dyspnea in the Emergency Department (PRIDE) Study, American Journal of Cardiology, 2005, pp. 948-954, vol. 95.

Januzzi, James L., Jr., The role of natriuretic peptide testing in guiding chronic heart failure management: Review of available data and recommendations for use, Archives of Cardiovascular Disease, 2012, pp. 40-50, vol. 105.

Jones, John I. and Clemmons, David R., Insulin-Like Growth Factors and Their Binding Proteins: Biological Actions, Endocrine Reviews, 1995, pp. 3-34, vol. 16, No. 1.

Kashani, Kianoush et al., Discovery and validation of cell cycle arrest biomarkers in human acute kidney injury, Critical Care, 2013, 12 pps., vol. 17.

Kempf, Tibor et al., Circulating Concentrations of Growth-Differentiation Factor 15 in Apparently Healthy Elderly Individuals and Patients with Chronic Heart Failure as Assessed by a New Immunoradiometric Sandwich Assay, Clinical Chemistry, 2007, pp. 284-291, vol. 53, No. 2.

Kempf, Tibor et al., Prognostic Utility of Growth Differentiation Factor-15 in Patients With Chronic Heart Failure, Journal of the American College of Cardiology, 2007, pp. 1054-1060, vol. 50, No. 11.

Kempf, Tibor et al., The Transforming Growth Factor-β Superfamily Member Growth-Differentiation Factor-15 Protects the Heart From Ischemia/Reperfusion Injury, Circulation Research, 2006, pp. 351-360, vol. 98.

Kiefer, Michael C. et al., The cDNA and derived amino acid sequence for human osteopontin, Nucleic Acids Research, 1989, p. 3306, vol. 17.

Kubo, Toru et al., Combined Measurements of Cardiac Troponin I and Brain Natriuretic Peptide Are Useful for Predicting Adverse Outcomes in Hypertrophic Cardiomyopathy, Circulation Journal, 2011, pp. 919-926, vol. 75.

Lang, Roberto M. et al., Recommendations for Chamber Quantification: A Report from the American Society of Echocardiography's Guidelines and Standards Committee and the Chamber Quantification Writing Group, Developed in Conjunction with . . . , Journal of the American Society of Echocardiography, 2005, pp. 1440-1463, vol. 18, No. 12.

Lawton, Lee N. et al., Identification of a novel member of the TGF-beta superfamily highly expressed in human placenta, Gene, 1997, pp. 17-26, vol. 203.

Levey, Andrew S. et al., A More Accurate Method to Estimate Glomerular Filtration Rate from Serum Creatinine: A New Prediction Equation, Annals of Internal Medicine, 1999, pp. 461-470, vol. 130, No. 6.

Maisel, Alan S. et al., Rapid Measurement of B-Type Natriuretic Peptide in the Emergency Diagnosis of Heart Failure, The New England Journal of Medicine, 2002, pp. 161-167, vol. 347, No. 3.

Mancia, Giuseppe et al., 2007 Guidelines for the management of arterial hypertension, European Heart Journal, 2007, pp. 1462-1536, vol. 28.

(56) References Cited

OTHER PUBLICATIONS

Masson, Serge et al., An Update on Cardiac Troponins as Circulating Biomarkers in Heart Failure, Current Heart Failure Reports, 2010, pp. 15-21, vol. 7.
Maurer, Mathew S. et al., Diastolic Dysfunction Can It Be Diagnosed by Doppler Echocardiography?, Journal of the American College of Cardiology, 2004, pp. 1543-1549, vol. 44, No. 8.
McMurray, John J. V. et al., ESC Guidelines for the diagnosis and treatment of acute and chronic heart failure 2012, European Heart Journal, 2012, pp. 1787-1847, vol. 33.
Morrish, D. W. et al., Identification by Subtractive Hybridization of a Spectrum of Novel and Unexpected Genes Associated with In Vitro Differentiation of Human Cytotrophoblast Cells, Placenta, 1996, pp. 431-441, vol. 17.
Moses, Marsha A. et al., Troponin I is present in human cartilage and inhibits angiogenesis, Proceedings of the National Academy of Sciences USA, 1999, pp. 2645-2650, vol. 96.
Motiwala, Shweta et al., Serial Measurement of Insulin-Like Growth Factor Binding Protein 7 Predicts Chronic Heart Failure Outcomes and Ventricular Remodeling: Results from the ProBNP Outpatient Tailored Chronic Heart Failure Therapy (PROTECT) Study, Journal of the American College of Cardiology, 2013, p. E565, vol. 16, No. 10.
Motiwala, Shweta R. et al., Measurement of Novel Biomarkers to Predict Chronic Heart Failure Outcomes and Left Ventricular Remodeling, Journal of Cardiovascular Translational Research, 2014, pp. 250-261, vol. 7.
Mueller, Thomas et al., Long-term stability of endogenous B-type natriuretic peptide (BNP) and amino terminal proBNP (NT-proBNP) in frozen plasma samples, Clinical Chemistry & Laboratory Medicine, 2004, pp. 942-944, vol. 42, No. 8.
Nagueh, Sherif F. et al., Recommendations for the Evaluation of Left Ventricular Diastolic Function by Echocardiography, Journal of the American Society of Echocardiography, 2009, pp. 107-133, vol. 22, No. 2.
Nishimura, Rick A. and Tajik, A. Jamil, Evaluation of Diastolic Filling of Left Ventricle in Health and Disease: Doppler Echocardiography Is the Clinician's Rosetta Stone, JACC, 1997, pp. 8-18, vol. 30, No. 1.
Nolan, John P. and Sklar, Larry A., Suspension array technology: evolution of the flat-array paradigm, TRENDS in Biotechnology, 2002, pp. 9-12, vol. 20, No. 1.
O'Meara, Eileen et al., Circulating Biomarkers in Patients with Heart Failure and Preserved Ejection Fraction, Current Heart Failure Reports, 2013, pp. 350-358, vol. 10.
O'Reilly, Michael S. et al., Endostatin: An Endogenous Inhibitor of Angiogenesis and Tumor Growth, Cell, 197, pp. 277-285, vol. 88.
Oh, Youngman et al., Synthesis and Characterization of Insulin-like Growth Factor-binding Protein (IGFBP)-7, The Journal of Biological Chemistry, 1996, pp. 30322-30325, vol. 271, No. 48.
Oldberg, Ake et al., Cloning and sequence analysis of rat bone sialoprotein (osteopontin) cDNA reveals an Arg-Gly-Asp cell-binding sequence, Proceedings of the National Academy of Sciences USA, 1986, pp. 8819-8823, vol. 83.
Oldberg, Ake et al., Identification of a Bone Sialoprotein Receptor in Osteosarcoma Cells, The Journal of Biological Chemistry, 1988, pp. 19433-19436, vol. 263, No. 38.
Ono, Yasuhiro et al., Expression of prostacyclin-stimulating factor, a novel protein, in tissues of Wistar rats and in cultured cells, Biochemical and Biophysical Research Communications, 1994, pp. 1490-1496, vol. 202, No. 3.
Ortega, Nathalie and Werb, Zena, New functional roles for non-collagenous domains of basement membrane collagens, Journal of Cell Science, 2002, pp. 4201-4214, vol. 115.
Ouzounian, Maral et al., Diastolic heart failure: mechanisms and controversies, Nature Clinical Practice Cardiovascular Medicine, 2008, pp. 375-386, vol. 5, No. 7.
Paralkar, Vishwas M. et al., Cloning and Characterization of a Novel Member of the Transforming Growth Factor-β/Bone Morphogenetic Protein Family, The Journal of Biological Chemistry, 1998, pp. 13760-13767, vol. 273, No. 22.
Paulus, Walter J. et al., How to diagnose diastolic heart failure: a consensus statement on the diagnosis of heart failure with normal left ventricular ejection fraction by the Heart Failure and Echocardiography Associations of the European Society of Cardiology, European Heart Journal, 2007, pp. 2539-2550, vol. 28.
Pfisterer, Matthias et al., BNP-Guided vs Sympton-Guided Heart Failure Therapy the Trial of Intensified vs Standard Medical Therapy in Elderly Patients With Congestive Heart Failure (TIME-CHF) Randomized Trial, JAMA, 2009, pp. 383-392, vol. 301, No. 4.
Praetorius, E. and Poulsen, H., Enzymatic Determination of Uric Acid with Detailed Directions, Scandinavian Journal of Clinical and Laboratory Investigation, 1953, pp. 273-280, vol. 5, No. 3.
Qi, Yong Fen et al., Effects of different peptide fragments derived from proadrenomedullin on gene expression of adrenomedullin gene, Peptides, 2002, pp. 1141-1147, vol. 23.
Richter, Mark M., Electrochemiluminescence (ECL), Chemical Reviews, 2004, pp. 3003-3036, vol. 104.
Schaefer, H. H. and Dieterle, T., Diagnosis and therapy of heart failure with normal ejection fraction, Therapeutische Umschau, 2011, pp. 81-87, vol. 68, No. 2, English Abstract.
Shuai, Xin-Xin et al., Diagnosis of heart failure with preserved ejection fraction: which parameters and diagnostic strategies are more valuable?, European Journal of Heart Failure, 2011, pp. 737-745, vol. 13.
Smith, M. W. et al., Delayed metabolism of human brain natriuretic peptide reflects resistance to neutral endopeptidase, Journal of Endocrinology, 2000, pp. 239-246, vol. 167.
Spencer, Kirk T. et al., Focused Cardiac Ultrasound: Recommendations from the American Society of Echocardiography, Journal of the American Society of Echocardiography, 2013, pp. 567-581, vol. 26.
Sprenger, Cynthia C. et al., Insulin-like Growth Factor Binding Protein-related Protein 1 (IGFBP-rP1) Is a Potential Tumor Suppressor Protein for Prostate Cancer, Cancer Research, 1999, pp. 2370-2375, vol. 50.
St. Croix, Brad et al., Genes Expressed in Human Tumor Endothelium, Science, 2000, pp. 1197-1202, vol. 289.
Swamy, Rajiv S. and Long, Roberto M., Echocardiographic Quantification of Left Ventricular Mass: Prognostic Implications, Current Cardiology Reports, 2010, pp. 277-282, vol. 12.
Tan, Mingjia et al., PTGF-β, a type β transforming growth factor (TGF-β) superfamily member, is a p53 target gene that inhibits tumor cell growth via TGF-β signaling pathway, Proceedings of the National Academy of Sciences, 2000, pp. 109-114, vol. 97, No. 1.
Tasheva, Elena S. et al., Mimecan/osteoglycin-deficient mice have collagen fibril abnormalities, Molecular Vision, 2002, pp. 407-415, vol. 8.
Town, Michael-Harold et al., A Sensitive Colorimetric Method for the Enzymatic Determination of Uric Acid, Journal of Clinical Chemistry & Clinical Biochemistry, 1985, p. 591, vol. 23, No. 9.
Tschöpe, Carsten et al., The role of NT-proBNP in the diagnostics of isolated diastolic dysfunction: correlation with echocardiographic and invasive measurements, European Heart Journal, 2005, pp. 2277-2284, vol. 26.
Ueland, Thor et al., Abstract 18269: Prognostic Value of Unsulin-Like Growth Factor Binding Protein 7 (IGFBP7) in Patients With Heart Failure: Data From Corona, Circulation, 2013, p. 18269, vol. 128, No. 22.
Van Breevoort, Dorothee et al., Proteomic Screen Identifies IGFBP7 as a Novel Component of Endothelial Cell-Specific Weibel-Palade Bodies, Journal of Proteome Research, 2012, pp. 2925-2936, vol. 11.
Wan, Siu-Hin et al., Pre-Clinical Diastolic Dysfunction, Journal of the American College of Cardiology, 2014, pp. 407-416, vol. 63, No. 5.
Watanabe, Shin et al., Insulin-like growth factor axis (insulin-like growth factor-I/insulin-like growth factor-binding protein-3) as a prognostic predictor of heart failure: association with adiponectin, European Journal of Heart Failure, 2010, pp. 1214-1222, vol. 12.

(56) References Cited

OTHER PUBLICATIONS

Weiner, Rory B. et al., Improvement in structural and functional echocardiographic parameters during chronic heart failure therapy guided by natriuretic peptides: mechanistic insights from the ProBNP Outpatent Tailored Chronic Heart Failure (PROTECT) Study, European Journal of Heart Failure, 2013, pp. 342-351, vol. 15.

Wu, Alan H. B. et al., Analytical and Clinical Evaluation of the Bayer ADVIA Centaur Automated B-Type Natriuretic Peptide Assay in Patients with Heart Failure: A Multisite Study, Clinical Chemistry, 2004, pp. 867-873, vol. 50, No. 5.

Yancy, Clyde W. et al., 2013 ACCF/AHA Guideline for the Management of Heart Failure a Report of the American College of Cardiology Foundation/American Heart Association Task Force on Practice Guidelines, Circulation, 2013, pp. e240-e319, vol. 128.

Yokoyama-Kobayashi, Midori et al., Human cDNA Encoding a Novel TGF-β Super-Family Protein Highly Expressed in Placenta, Journal of Biochemistry, 1997, pp. 622-626, vol. 122, No. 3.

Yu, C. M. et al., Diastolic dysfunction and natriuretic peptides in systolic heart failure Higher ANP and BNP levels are associated with the restrictive filling pattern, European Heart Journal, 1996, pp. 1694-1702, vol. 17.

Zile, Michael R. and Brutsaert, Dirk L., New Concepts in Diastolic Dysfunction and Diastolic Heart Failure: Part II Casual Mechanisms and Treatment, Circulation, 2002, pp. 1503-1508, vol. 105.

Ziouein, Fouad et al., Heart Failure with Preserved Ejection Fraction: Emerging Drug Strategies, Journal of Cardiovascular Pharmacology, 2013, pp. 13-21, vol. 62, No. 1.

Zweig, Mark H. and Campbell, Gregory, Receiver-Operating Characteristic (ROC) Plots: A Fundamental Evaluation Tool in Clinical Medicine, Clinical Chemistry, 1993, pp. 561-577, vol. 39, No. 4.

\* cited by examiner

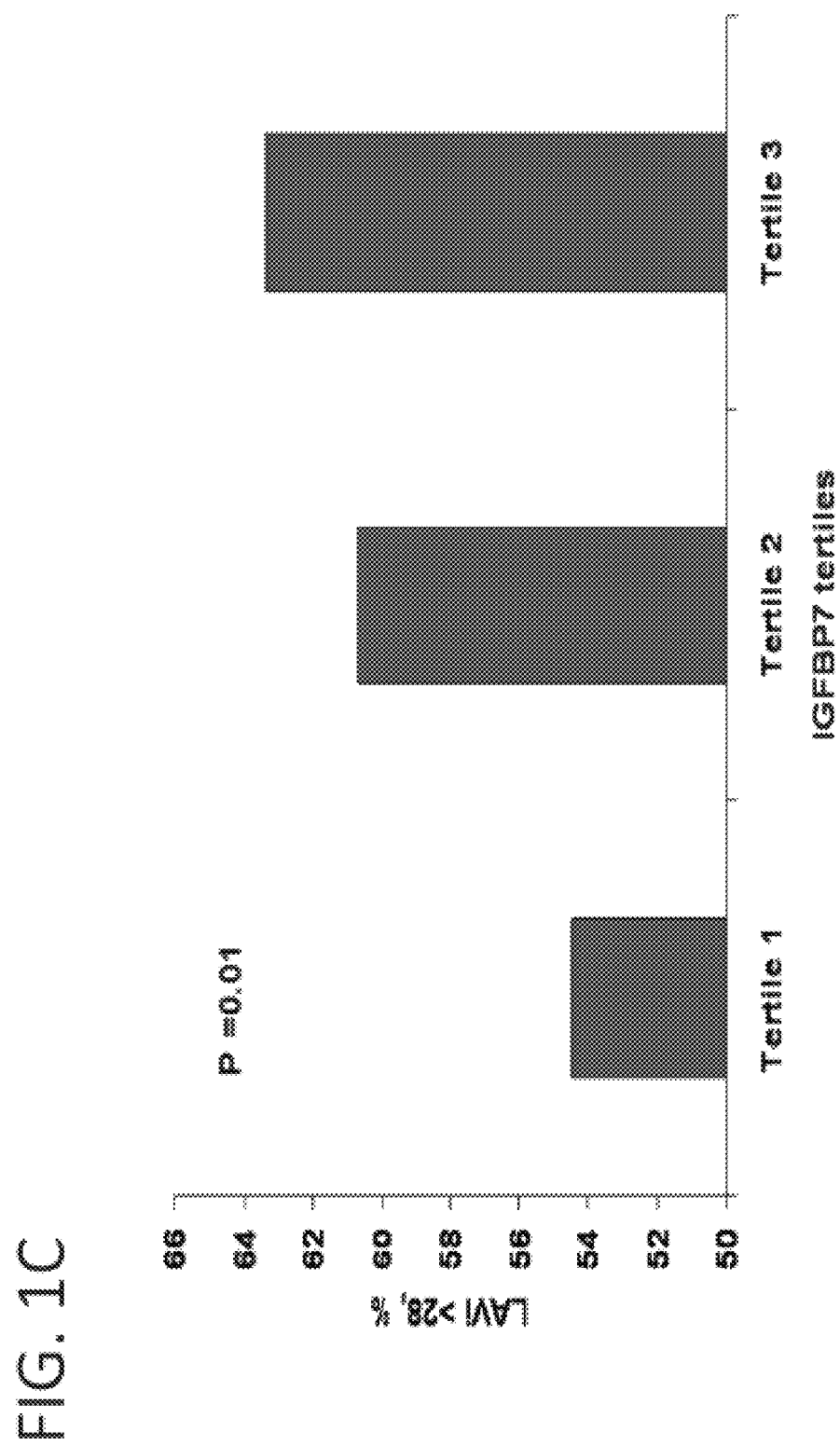

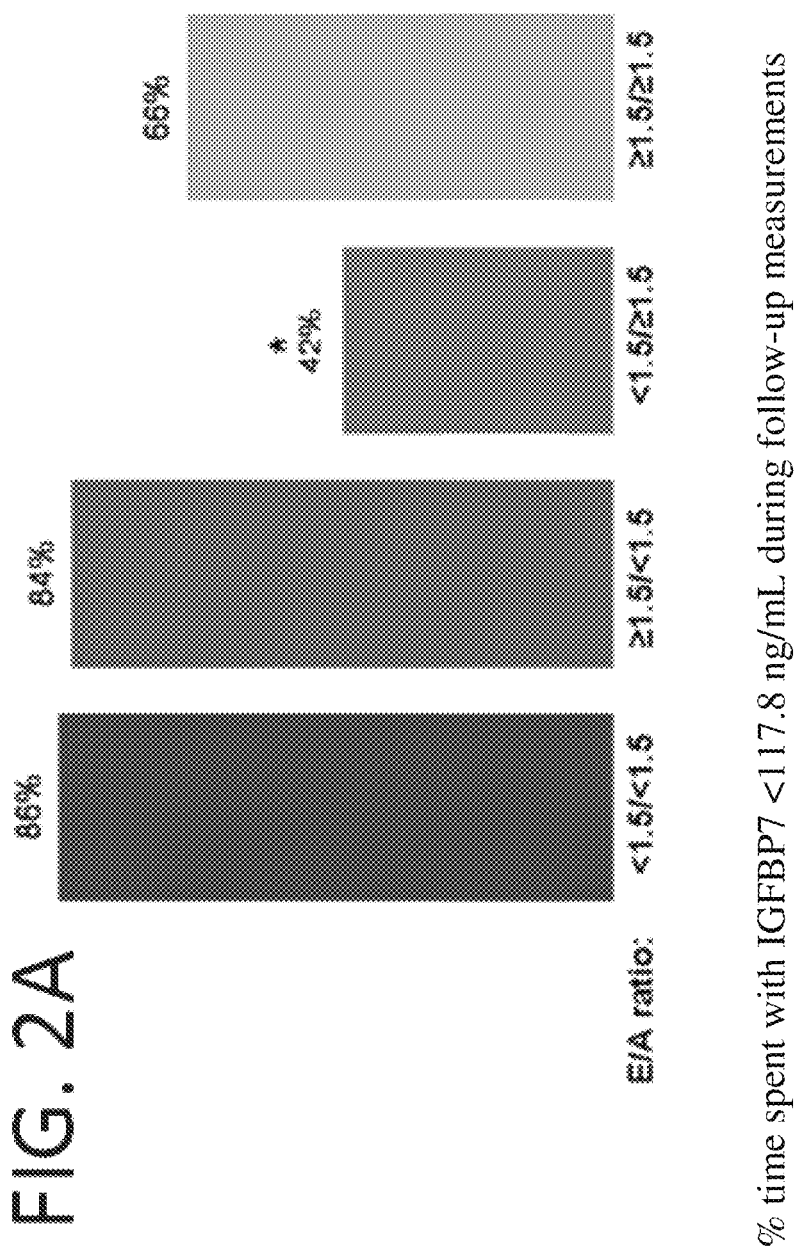

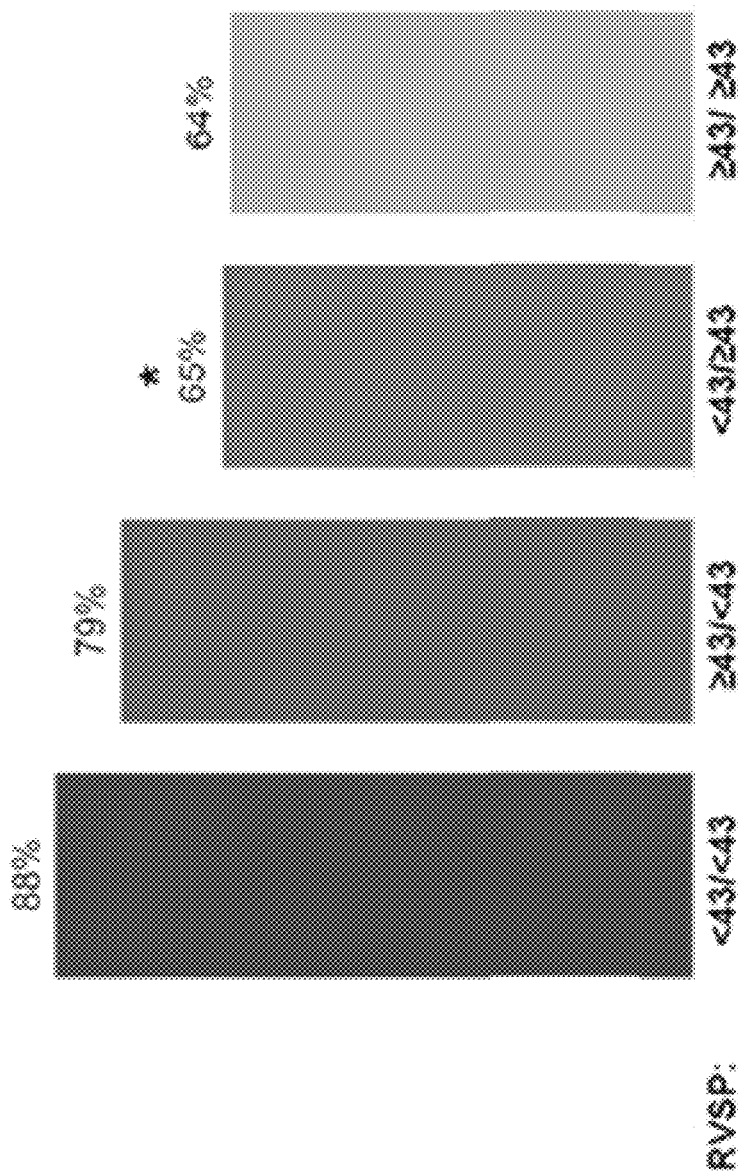

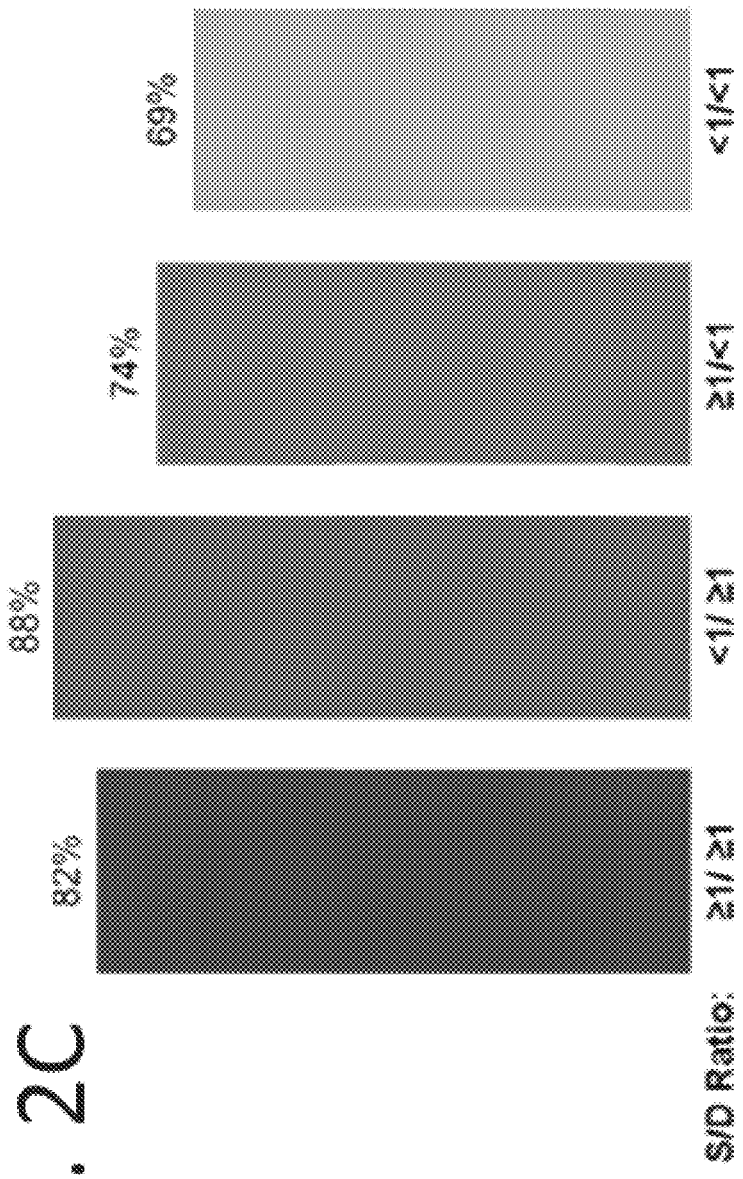

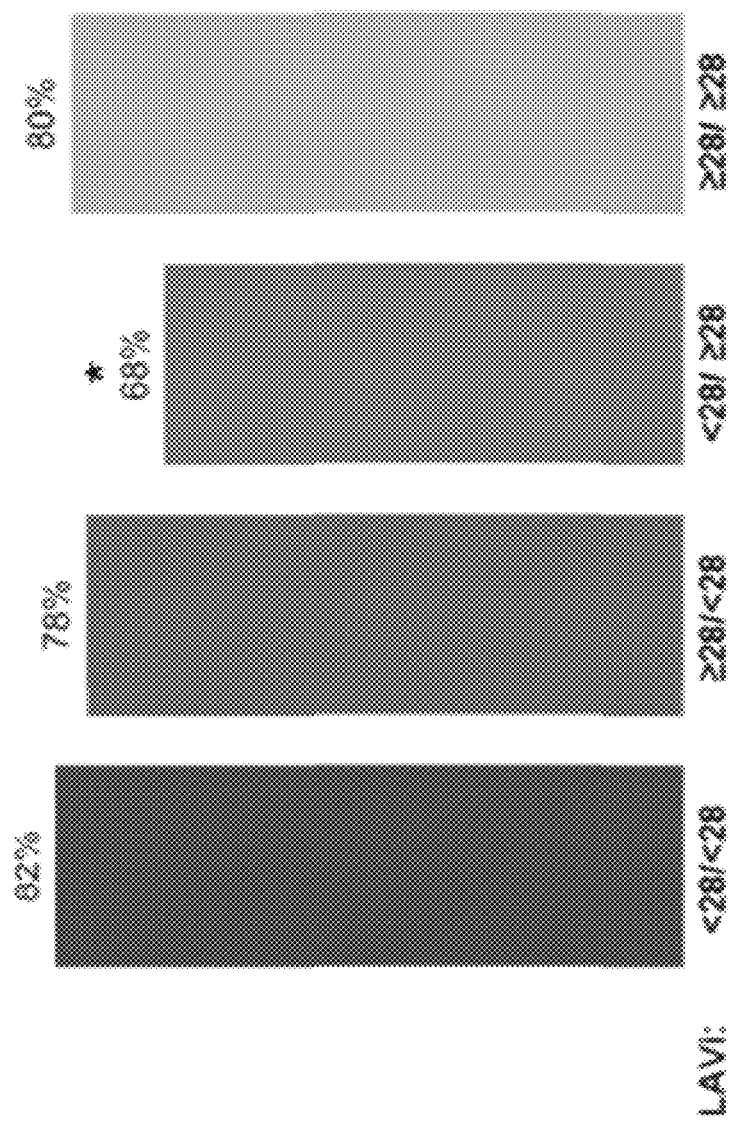

IGFBP7 FOR DIAGNOSING DIASTOLIC DYSFUNCTION

CROSS-REFERENCE TO RELATED APPLICATIONS

This application is a divisional of U.S. application Ser. No. 15/274,533 filed Sep. 23, 2016, which is a continuation of International Patent Application No. PCT/EP2015/056418 filed Mar. 25, 2015, which claims priority to European Patent Application No. 14161732.4 filed Mar. 26, 2014, the disclosures of which are hereby incorporated by reference in their entirety.

BACKGROUND OF THE DISCLOSURE

The use of biomarkers for the care of patients with heart failure (HF) has expanded significantly. The natriuretic peptides (NPs), including B-type natriuretic peptide (BNP) and its amino-terminal cleavage equivalent (NT-proBNP) are now widely used for diagnosis, prognosis, and management of affected patients (Yancy et al., 2013 ACCF/AHA Guideline for the Management of Heart Failure: A report of the American College of Cardiology Foundation/American Heart Association Task Force on Practice Guidelines, Circulation, 2013; 128:e240-319). Following BNP and NT-proBNP, a wide range of novel biomarkers are being examined, each with potential promise for additive evaluation of patients suffering from the complex pathophysiology of HF. In this regard, there has been considerable effort to better understand the mechanistic link(s) between concentrations of cardiac biomarkers and the underlying cardiovascular pathophysiological processes from which they are released.

The natriuretic peptides have been found to be associated with a wide array of abnormalities of cardiovascular structure and function, including both systolic and diastolic function of the left ventricle (LV) (Tschope et al., The role of NT-proBNP in the diagnostics of isolated diastolic dysfunction: Correlation with echocardiographic and invasive measurements, Eur Heart J. 2005; 26:2277-2284, Weiner et al., Improvement in structural and functional echocardiographic parameters during chronic heart failure therapy guided by natriuretic peptides: Mechanistic insights from the proBNP outpatient tailored chronic heart failure (protect) study, Eur J Heart Fail. 2013; 15:342-351, Yu et al., Diastolic dysfunction and natriuretic peptides in systolic heart failure. Higher ANP and BNP levels are associated with the restrictive filling pattern, Eur Heart J. 1996; 17:1694-1702). Relative to the latter, identifying and grading severity of abnormal diastolic function is complex, with several echocardiographic parameters assessed in this exercise (Nagueh et al., Recommendations for the evaluation of left ventricular diastolic function by echocardiography, J Am Soc Echocardiogr. 2009; 22:107-133). While the natriuretic peptides are elevated in HF due to diastolic dysfunction, they are entirely non-specific in this association (Daniels et al., Natriuretic peptides, J Am Coll Cardiol. 2007; 50:2357-2368) thus limiting their applicability. Therefore, biomarker(s) predominantly useful to assist in the diagnosis and grading of abnormal diastolic function would be exceptionally valuable in clinical practice.

The insulin-like growth factor axis has previously been found to be a predictor of outcomes in HF (Watanabe et al., Insulin-like growth factor axis (insulin-like growth factor-i/insulin-like growth factor-binding protein-3) as a prognostic predictor of heart failure: Association with adiponectin, Eur J Heart Fail. 2010; 12:1214-1222). Insulin-like growth factor-binding protein 7 (IGFBP7) in particular was identified recently as a potential novel HF marker through proteomic and informatic searches of animal models of cardiac hypertrophy and human tissues of heart failure (Chugh et al., Pilot study identifying myosin heavy chain 7, desmin, insulin-like growth factor 7, and annexin a2 as circulating biomarkers of human heart failure, Proteomics, 2013; 13:2324-2334). IGFBP7 was principally associated with cardiac hypertrophy and was expressed at high levels in HF, but not in normal serum. IGFBP7 also appears to be expressed in the vasculature, potentially regulating angiogenesis (van Breevoort et al., Proteomic screen identifies IGFBP7 as a novel component of endothelial cell-specific weibel-palade bodies, J Proteome Res. 2012; 11:2925-2936).

Myocardial diastolic dysfunction is a different type of heart failure versus myocardial systolic dysfunction. Heart failure (HF) patients need to be stratified separately and specifically for therapy of diastolic dysfunction. Several new drugs are in development for the treatment of diastolic dysfunction: LCZ696 (Novartis PhII), Sildenafil, Spironolactone, Anakinra, HISDN.

Diagnosis of diastolic dysfunction is time and cost consuming. A functional and structural classification is needed with imaging means.

Growth-differentiation factor-15 (GDF-15) is a member of the transforming growth factor-β cytokine superfamily. GDF-15 has been described as a strong predictor of cardiovascular events and an indicator for cardiovascular complications (Brown, D. A. et al., 2002 The Lancet, 359: 2159-2163; US2003/0232385; Kempf 2006, Circ Res 98: 351-360). Kempf et al. showed that circulating levels of GDF-15 are related to severity of CHF and predict the risk of death in patients with chronic heart failure (Clinical Chemistry 53:2; 284-291 (2007); Am Coll Cardiol, 2007; 50:1054-1060).

BRIEF SUMMARY OF THE DISCLOSURE

The present invention relates to a method for diagnosing and/or grading diastolic dysfunction or at least one structural or functional abnormality associated with diastolic dysfunction. The method comprises measuring the level of IGFBP7 (Insulin like growth factor binding protein 7) and, optionally, the level of at least one further marker in a patient suffering from heart failure, and comparing the level to a reference level. Further envisaged is a method of monitoring diastolic function in a patient suffering from heart failure. Also encompassed by the present invention are kits and devices adapted to carry out the method of the present invention.

As set forth above, assessment of diastolic dysfunction requires expensive instrumentation, specialized imaging techniques, and expert image recording and interpreting skills. Widespread application of echocardiographic screening for diastolic dysfunction has been limited by cost-tobenefit consideration. Therefore, biomarkers that could be used for reliably assessing diastolic dysfunction are highly required.

The technical problem underlying the present invention can be seen as the provision of means and methods for complying with the aforementioned needs.

The technical problem is solved by the embodiments characterized in the claims and herein below.

BRIEF DESCRIPTION OF THE FIGURES

The Figures show:

FIG. 1C: Diastolic parameters shown in tertiles of IGFBP7 for Left Atrial Volume Index >28 mL/m$^2$.

All but E'<8 cm/sec showed substantial association between IGFBP7 concentrations and more severe parameters.

FIG. 2A: Changes in diastolic parameter E/A ratio over a mean follow up of 10 months as a function of time duration spent with an IGFBP7 concentration <117.8 ng/mL.

FIG. 2B: Changes in diastolic parameter RSVP over a mean follow up of 10 months as a function of time duration spent with an IGFBP7 concentration <117.8 ng/mL.

FIG. 2C: Changes in diastolic parameter S/D ratio over a mean follow up of 10 months as a function of time duration spent with an IGFBP7 concentration <117.8 ng/mL.

FIG. 2D: Changes in diastolic parameter LAVI over a mean follow up of 10 months as a function of time duration spent with an IGFBP7 concentration <117.8 ng/mL.

The amount of time spent below 117.8 ng/mL was lowest in those developing worsened E/A ratio, RSVP, and LAVi (P<0.05 for all).

Figure 3A:
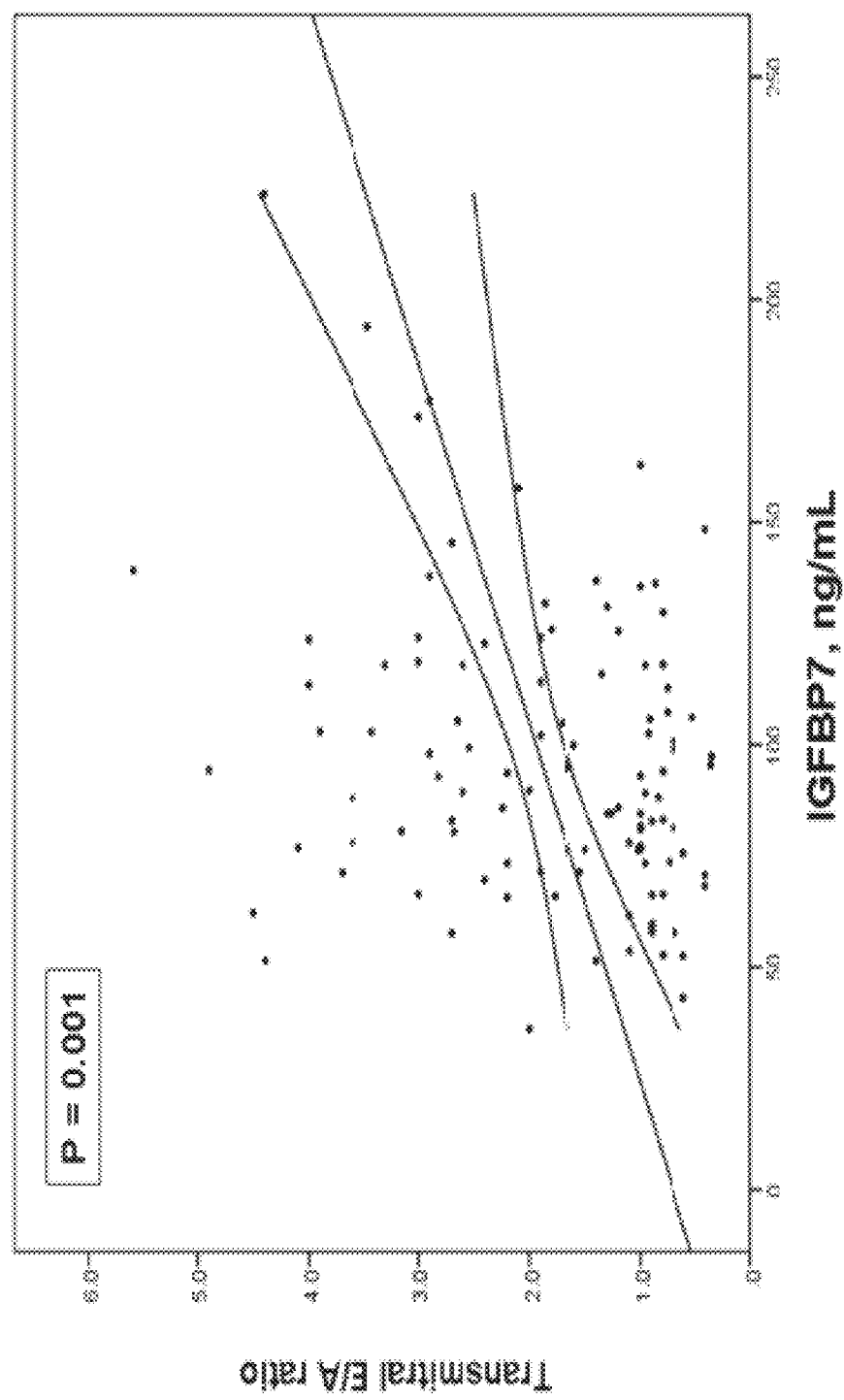

FIG. 3A: Correlation between IGFBP7 and diastolic parameter transmitral Doppler inflow shown as scatter plot with the line of fit and 95th percent confidence intervals detailed.

Figure 3B:
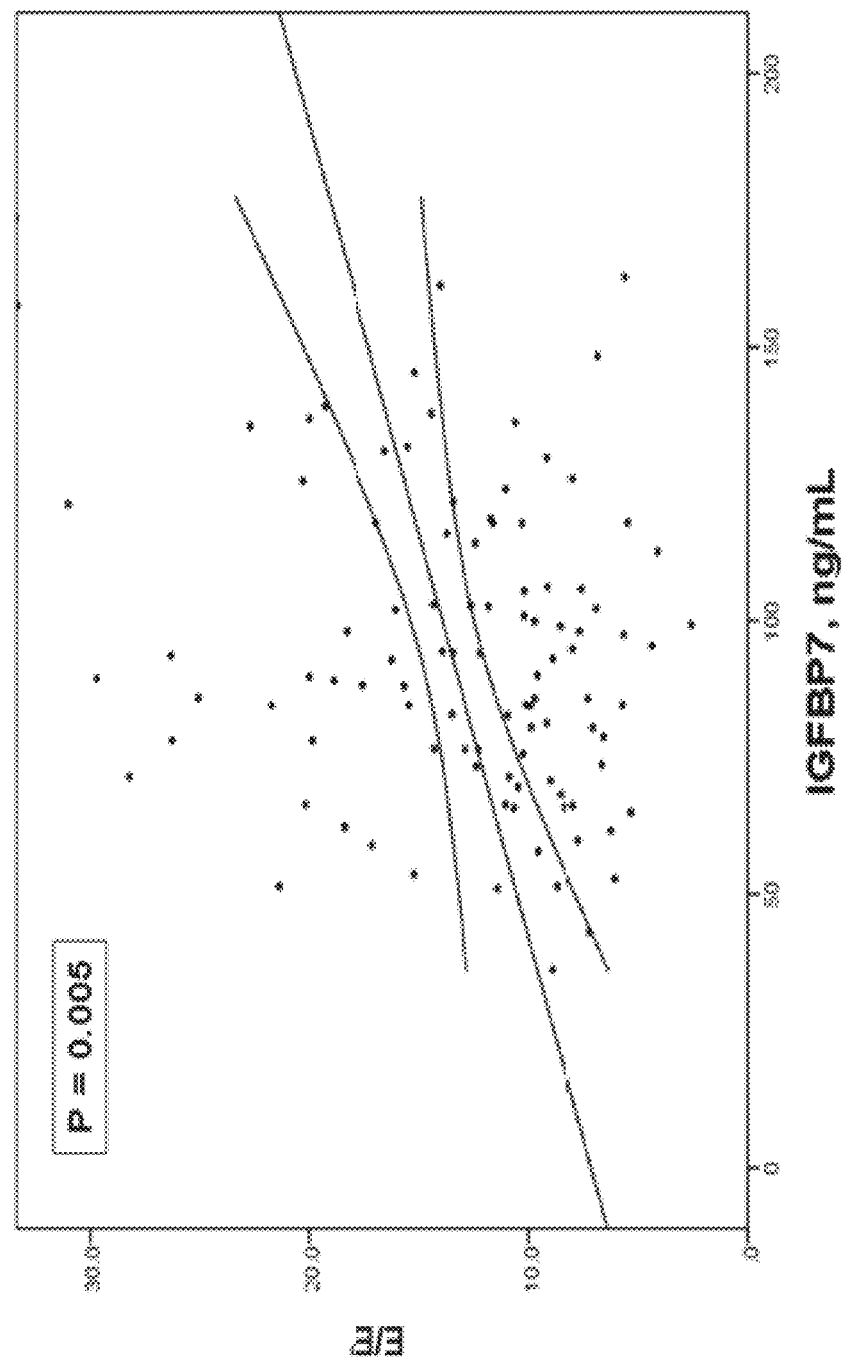

FIG. 3B: Correlation between IGFBP7 and diastolic parameter E/E' shown as scatter plot with the line of fit and 95th percent confidence intervals detailed.

Figure 3C:
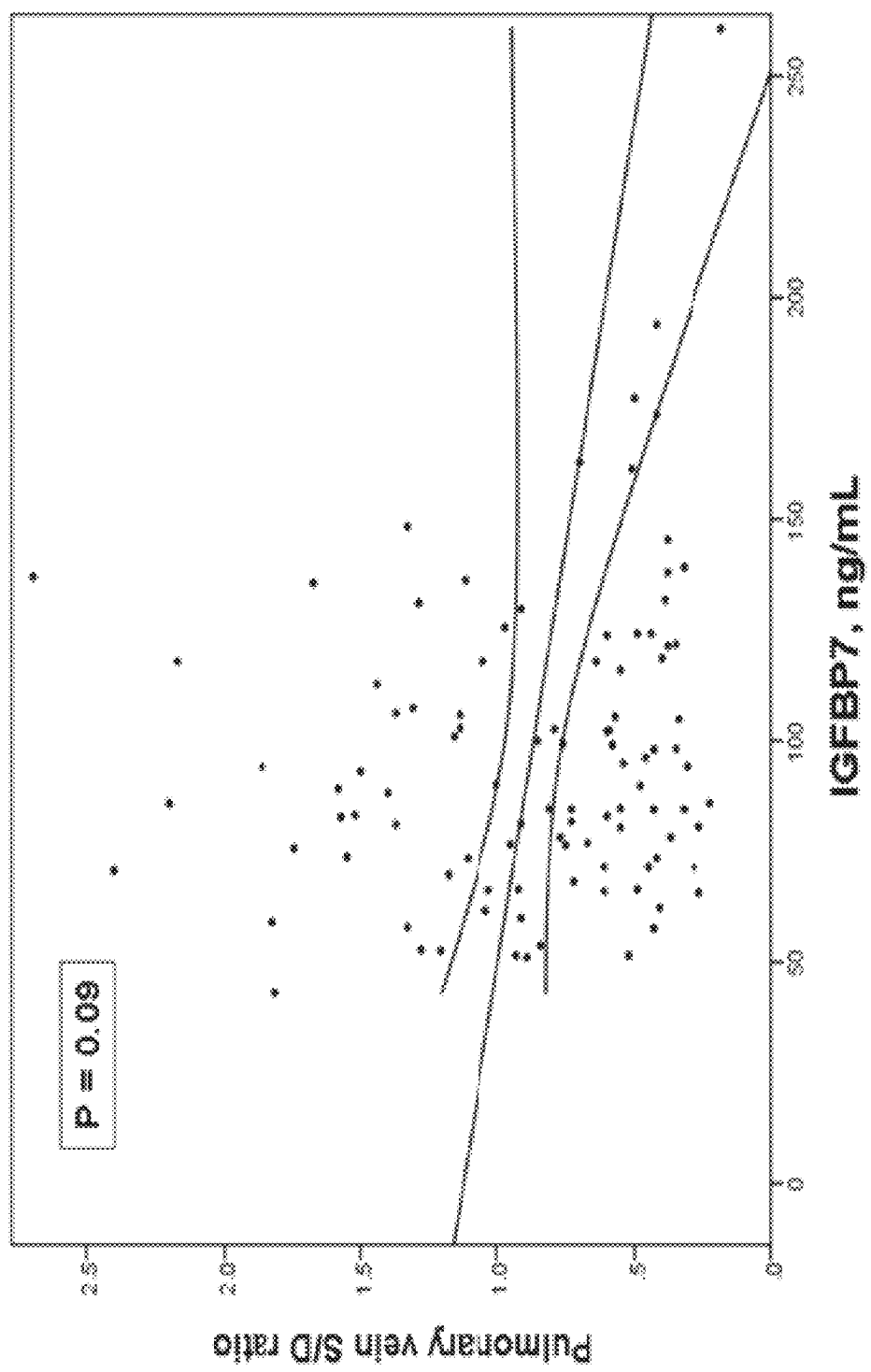

FIG. 3C: Correlation between IGFBP7 and diastolic parameter pulmonary vein S/D ratio shown as scatter plot with the line of fit and 95th percent confidence intervals detailed.

Figure 3D:
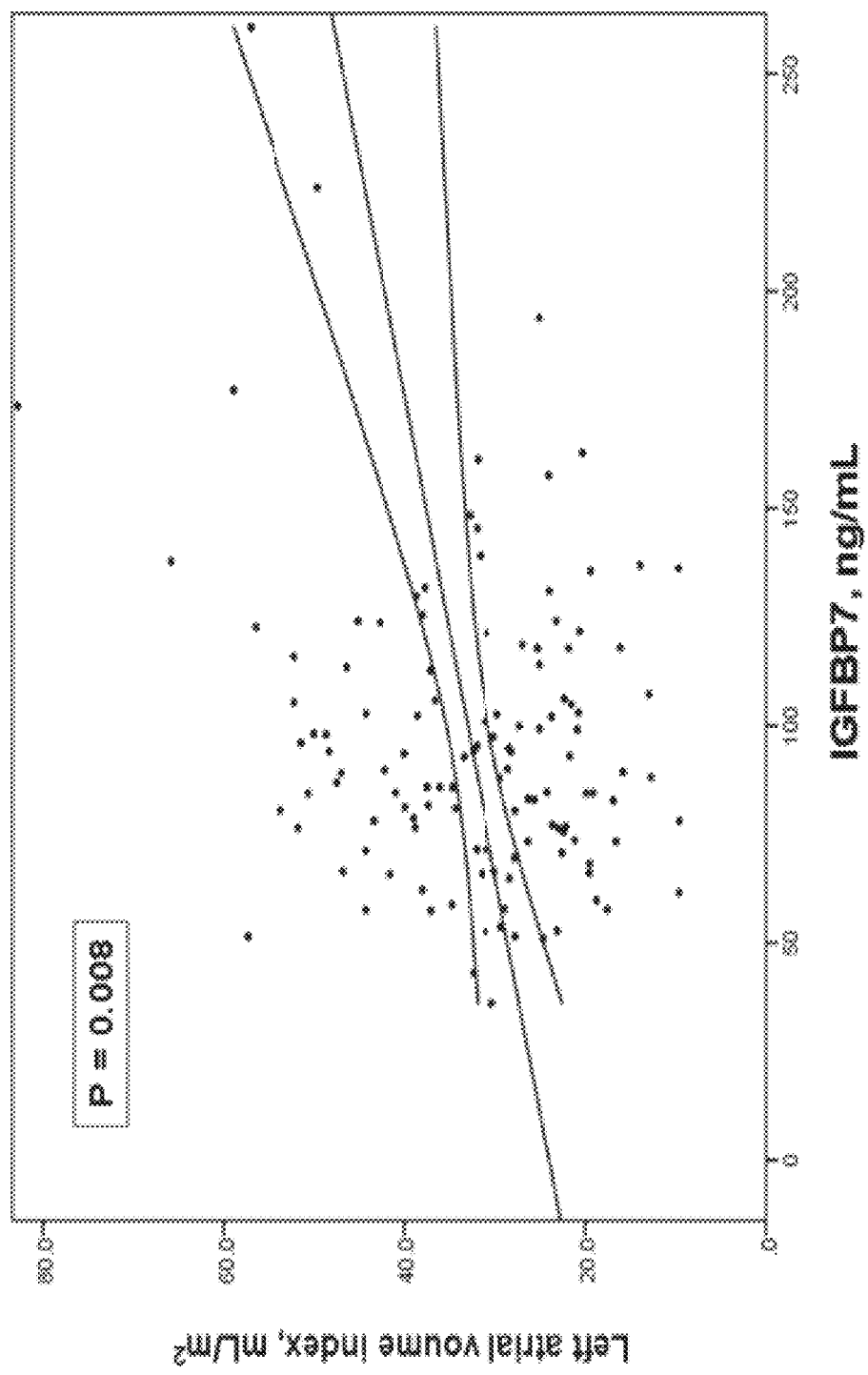

FIG. 3D: Correlation between IGFBP7 and diastolic parameter left atrial volume index (LAVi) shown as scatter plot with the line of fit and 95th percent confidence intervals detailed.

Figure 3E:
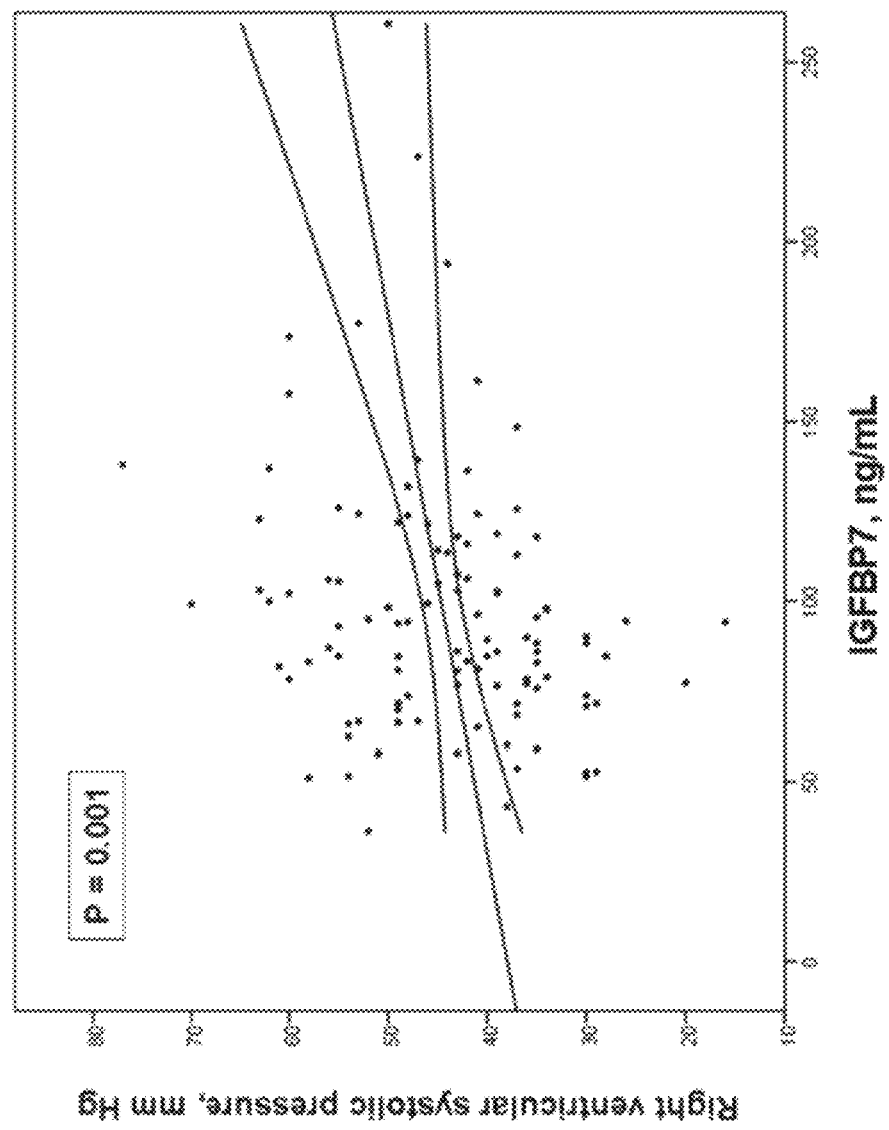

FIG. 3E: Correlation between IGFBP7 and diastolic parameter right ventricular systolic pressure (RSVP) shown as scatter plot with the line of fit and 95th percent confidence intervals detailed.

DETAILED DESCRIPTION

In the context of the studies underlying the present invention it has been found that IGFBP7 is a reliable biomarker for the assessment of diagnostic dysfunction.

Accordingly, the present invention relates to a method for diagnosing and/or grading diastolic dysfunction and/or at least one structural or functional abnormality associated with diastolic dysfunction in a patient suffering from heart failure, said method comprising the steps of
   a) measuring the level of IGFBP7 (Insulin like growth factor binding protein 7) in a sample from a patient suffering from heart failure, and
   b) comparing the level of IGFBP7 measured in step a) to a reference level.

The method of the present invention, preferably, is an ex vivo or in vitro method. Moreover, it may comprise steps in addition to those explicitly mentioned above. For example, further steps may relate to sample pre-treatments or evaluation of the results obtained by the method. The method may be carried out manually or assisted by automation. Preferably, step (a) and/or (b) may in total or in part be assisted by automation, e.g., by a suitable robotic and sensory equipment for the measurement in step (a) or a computer-implemented comparison and/or assessment based on said comparison in step (b).

Diastolic dysfunction and/or at least one structural or functional abnormality is diagnosed/graded by carrying out the comparison in step b) of the method of the present invention. Accordingly, the method may further comprise step c) of diagnosing and/or grading diastolic dysfunction and/or at least one structural or functional abnormality of the heart based on the results of step b).

Alternatively, the method may further comprise step c) of providing a diagnosis and/or a grading of at least one structural or functional abnormality of the heart associated with diastolic dysfunction based on the results of step b).

In an embodiment of the present invention, the biomarker IGFBP7 (and, optionally, the at least one further biomarker as described below) is measured by contacting the sample with an agent that specifically binds to IGFBP7 (and, optionally, with a further agent, or further agents that specifically bind(s) to said at least one further biomarker), thereby forming a complex between the agent and IGFBP7 (and optionally a complex between the further agent and the at least one further biomarker), detecting the amount of complex (complexes) formed, thereby measuring the level of IGFBP7 (and optionally the level of the at least one further biomarker).

In accordance with present invention, diastolic dysfunction and/or at least one structural or functional abnormality of the heart associated with diastolic dysfunction shall be graded and/or diagnosed.

The term "diastolic dysfunction" is well known in the art. Preferably, the term refers to a reduced pump function of the heart due to impaired ventricular filling. Thus, the term, preferably, refers to a decline in performance of one or both ventricles of the heart during the time phase of diastole. How to diagnose diastolic dysfunction with conventional measures is well known in the art (see Examples section, or e.g. Shuai et al., Eur J Heart Fail, 2011; 13: 737-745; or Schafer and Dieterle, Therapeutische Umschau 2011; 68 (2): 81-87, or Paulus et al., Eur Heart J (2007) 28 (20): 2539-2550 all of which are herewith incorporated by reference with respect to their entire disclosure content).

According to the diastolic filling pattern, diastolic dysfunction can be graded as follows (see also Nishimura et al. Journal of the American College of Cardiology, 1997; 30:8-18,):
   Grade 1=impaired relaxation pattern with normal filling pressure
   1a=impaired relaxation pattern with increased filling pressure
   Grade 2=pseudonormalized pattern
   Grade 3=reversible restrictive pattern
   Grade 4=irreversible restrictive pattern As used herein, the term "diastolic dysfunction" encompasses diastolic dysfunction grade 1, 1a, 2, 3 and 4, in particular the term encompasses diastolic dysfunction grade 3 and/or 4 (in particular as defined in Nishimura which is herewith incorporated by reference with respect to its entire disclosure content). Preferably, the pattern is irreversible.

The phrase "structural or functional abnormality associated with diastolic dysfunction" is well known by the skilled person. It is to be understood that said abnormality is an abnormality of the heart associated with diastolic dysfunction. Preferably, the abnormality is an increased parameter (in some cases a decreased parameter) that was increased (or in some cases decreased) in patients with elevated IGFBP7 levels in the Examples section (see in particular Example 1, Example 2, or table 2 in Example 1). More preferably, the at least one structural or functional abnormality of the heart associated with diastolic dysfunction is an increased (or in some cases a decreased) parameter as listed in table 2 of the examples section (see first column), in particular in part C of said table ("Diastolic function and estimates of filling pressure"), or in table 4. Even more preferably, the abnormality is an increased (or decreased) parameter for which the p-value is table 2 is lower than 0.01, in particular lower than 0.005. Most preferably, the structural or functional abnormality associated with diastolic dysfunction is at least one abnormality selected from the group consisting of increased left atrial size (preferably, an increased left atrial superior-inferior diameter), increased left atrial volume index, increased E peak velocity (i.e. transmitral Doppler E wave velocity), decreased A peak velocity (i.e. lower transmitral Doppler A wave velocity), increased transmitral E/A ratio, increased mitral inflow E velocity to tissue Doppler E' velocity ratio (i.e. increased E/E' ratio), an increased E'/A' ratio, decreased pulmonary vein systolic peak velocity, increased pulmonary vein diastolic peak velocity, decreased pulmonary vein systolic/diastolic ratio, increased right ventricular area, increased right ventricular systolic pressure (RVSP), increased right ventricular dilation, increased right atrium size (preferably an increased right atrial superior-inferior diameter), a more than mild mitral regurgitation, and a more than mild tricuspid regurgitation. For an explanation of the parameters as well s for the determination thereof, see also Examples section (Echocardiography protocol). Further preferred abnormalies are disclosed in McMurray et al. (European Heart Journal (2012) 33, 1787-1847) or Spencer et al. (J Am Soc Echocardiogr 2013; 26:567-81.) which are both incorporated by reference with respect to their entire disclosure content).

The parameters "left atrial size", and "left atrial volume index" are parameters for the left atrial (LA) size and volume, respectively.

Preferably, left atrial size, in particular the left atrial diameter, is increased, if the LA size is larger than about 58 mm, in particular larger than about 60 or about 62 mm. In Example 2, the left atrial size is referred to as LA diameter.

Preferably, left atrial volume index (LAVi) is increased, if the LAVi is larger than about 28 ml/m$^2$, in particular larger than about 32 ml/m$^2$ or larger than about 36 ml/ml$^2$. In Example 2, the LAVi is also referred to as LA square.

The parameters "E peak velocity", "A peak velocity", "transmitral E/A ratio", "E/E' ratio", "E'/A' ratio", "pulmonary vein systolic peak velocity", "pulmonary vein diastolic peak velocity", "pulmonary vein systolic/diastolic ratio" are parameters for diastolic function and estimates of filling pressure. The E'/A' ratio is preferably the early/late diastolic filling velocity ratio.

Preferably, E peak velocity is increased, if it is larger than about 79 msec, in particular larger than about 98 or about 120 msec.

Preferably, A peak velocity is decreased, if it is lower than about 54 msec, in particular lower than about 44 or about 36 msec.

Preferably, the transmitral E/A ratio is increased, if it is larger than about 1.8, in particular larger than about 2.25 or about 3.2. In Example 2, the transmitral E/A ratio is referred to as E/A.

Preferably, the E/E' ratio is increased, if it is larger than about 10.8, in particular larger than about 15 or about 20.2.

Preferably, the E'/A' ratio is increased, if it is larger than about 1.3, in particular larger than about 1.45 or about 2.54.

Preferably, pulmonary vein systolic peak velocity is decreased, if it is lower than about 36 msec, in particular lower than about 32 or about 26 msec.

Preferably, pulmonary vein diastolic peak velocity is increased, if it is larger than about 54 msec, in particular larger than about 60 or about 76 msec.

Preferably, the pulmonary vein systolic/diastolic ratio is decreased, if it is lower than about 1, in particular lower than about 0.49 or about 0.38.

Preferably, RVSP is increased, if it is larger than about 43 mm Hg, in particular larger than about 53 or about 60 mm Hg.

The parameter "right atrium size" is a right atrial parameter. The parameter is increased, if it is larger than about 48 mm, in particular larger than about 54 or about 60 mm.

The abnormalities/parameters are well known in the art and can be assessed by the skilled person without further ado. The abnormalities/parameters, e.g., can be determined as described in the Examples section. "Diastolic dysfunction" as well as the abnormalities/parameters referred to above are reviewed by Wan et al. JACC Vol. 63, No. 5, 2014: 407-16 which is herewith incorporated by reference with respect to its entire disclosure content as well. Further, diastolic dysfunction as well as abnormalities as referred to a herein are described by McMurray et al. and Spencer et al. (see citations above).

The term "at least one" as used herein means one or more than one, e.g. 2, 3, 4 etc. Thus, it is envisaged to diagnose/grade one or more than abnormalities. In an embodiment, the term "at least one" means "a".

The term "diagnosing" as used herein means assessing whether a patient as referred to herein suffers from diastolic dysfunction and/or at least one structural or functional abnormality associated with diastolic dysfunction, or not. The term is used to indicate that the method according to the present invention will classify a patient as having diastolic dysfunction and/or at least one structural or functional abnormality associated with diastolic dysfunction or in the alternative as not having said dysfunction or abnormality. A level of IGFBP7 (and optionally of the at least one further biomarker) above the reference level is used for providing a diagnosis of diastolic dysfunction and/or at least one structural or functional abnormality associated with diastolic dysfunction.

The term "grading diastolic dysfunction" and/or a "grading at least one structural or functional abnormality associated with diastolic dysfunction" as used herein, preferably, relates to assessing the severity of said dysfunction and/or abnormality. In an embodiment, it is differentiated between a mild and a severe form of said dysfunction and/or abnormality.

As will be understood by those skilled in the art, the assessments described above, i.e. the grading or the diagnosis, are usually not intended to be correct for all (i.e. 100%) of the patients to be diagnosed/graded. The term, however, requires that a statistically significant portion of patients can be identified (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the patients of a population can be properly diagnosed/graded by the method of the present invention.

The phrase "indicates that the patient suffers from" a disease and/or an abnormality as referred to herein, or from a mild or severe form of said disease and/or abnormality is used to illustrate that a level of the biomarker is very valuable but is not diagnostic without error. As the skilled artisan will appreciate, in many diseases, no biochemical marker has 100% specificity and at the same time 100% sensitivity. In such case assessment e.g., with regard to the level of IGFBP7 (and optionally of the at least one further biomarker) in the disease/abnormality is performed with a certain likelihood, e.g. at a given level of specificity or at a given level of sensitivity. The skilled artisan is fully familiar with the mathematical/statistical methods used to calculate specificity, sensitivity, positive predictive value, negative predictive value, reference value or total error.

The phrase "providing a diagnosis/assessment/grading/monitoring" as used herein refers to using the information or data generated relating to the level of IGFBP7 (and optionally of at least one further marker as described below) in a sample of a patient to diagnose/assess/grade/monitor diastolic dysfunction and/or at least one structural or functional abnormality associated with diastolic dysfunction in a patient as referred to herein. The information or data may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of IGFBP7 (and optionally of at least one further marker as described below) to a reference level. In some embodiments, the information or data includes an indication that the patient is diagnosed/assessed/graded with a disease/abnormality as referred to herein.

The "subject" or "patient" as referred to herein is, preferably, a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Preferably, the patient is a human patient. The terms "subject", "patient" and "individual" may be used interchangeably herein.

In accordance with the present invention, the patient to be tested shall suffer from heart failure. The term "heart failure" is well known in the art. As used, herein the term, preferably, relates to an impaired function of the heart being accompanied by symptoms of heart failure as known to the person skilled in the art. Accordingly, the patient preferably suffers from symptomatic heart failure. Accordingly, the patient shall suffer from advanced heart failure. It is particularly contemplated that the term "heart failure" as used herein refers to stage C and/or D of the ACC/AHA classification, or class III and/or IV of the NYHA classification. In these stages, the patient shows typical symptoms of heart failure, i.e. the patient is not apparently healthy. The patient having heart failure and being classified into stage C or D has undergone permanent, non reversible structural and/or functional changes to his myocardium, and as a consequence of these changes, full health restoration is not possible.

The ACC/AHA classification is a classification for heart failure developed by the American College of Cardiology and the American Heart Association (see J. Am. Coll. Cardiol. 2001; 38; 2101-2113, updated in 2005, see J. Am. Coll. Cardiol. 2005; 46; e1-e82). 4 stages A, B, C and D are defined. Stages A and B are not HF (heart failure) but are considered to help identify patients early before developing "truly" HF. Stages A and B patients are best defined as those with risk factors for the development of HF. For example, patients with coronary artery disease, hypertension, or diabetes mellitus who do not yet demonstrate impaired left ventricular (LV) function, hypertrophy, or geometric chamber distortion would be considered stage A, whereas patients who are asymptomatic but demonstrate LV hypertrophy (LVH, a phenomenon in which the walls of the ventricles thicken) and/or impaired LV function would be designated as stage B. Stage C then denotes patients with current or past symptoms of HF associated with underlying structural heart disease (the bulk of patients with HF), and stage D designates patients with truly refractory HF.

As set forth above, the patient to be tested shall, preferably, suffer from heart failure stage C or D according to the ACC/AHA classification (see citation above), and/or from heart failure NYHA class III or IV according to the NYHA classification. Thus, the patient shall suffer from a more advanced form of heart failure. Also preferably, the patient to be tested in accordance with the present invention has a serum or plasma level of NT-proBNP of larger than about 800 pg/ml, more preferably of larger than about 1000 pg/ml, and most preferably, of larger than about 1200 pg/ml.

Heart failure as referred to herein may be heart failure of any cause. In an embodiment, the heart failure is due to left ventricular systolic dysfunction (in particular is caused by left ventricular systolic dysfunction). Accordingly, the patient who suffers from heart failure also suffers from systolic dysfunction, in particular left ventricular systolic dysfunction. The term "systolic dysfunction" is well known in the art. As used herein, the term preferably refers to a reduced pump function of the heart due to a decreased contractility of the ventricle.

The patient suffering from heart failure as referred to herein, in particular, shall have a reduced left ventricular ejection fraction (LVEF). The term "left ventricular ejection fraction" is well known in the art. A patient who has reduced LVEF, preferably, has a LVEF of less than 50%, more preferably, of less than 45% and most preferably, of less than 40%. Further, it is envisaged that the patient has a LVEF of less than 30%.

In an embodiment of the present invention, however, the patient may have a preserved LVEF (e.g. larger than 50%). If the patient has a preserved LVEF, the patient preferably from heart failure stage A, B, or C according to the ACC/AHA classification, and/or from heart failure NYHA class I, II or III according to the NYHA classification. A patient who has a preserved LVEF, preferably, has a LVEF of larger than 50%, more preferably of larger than 55% or most preferably of larger than 60%. If the patient has a preserved LVEF, it is e.g. envisaged that a parameter as set forth in Example 2 is diagnosed or graded.

How to assess the LVEF is well known in the art. In an embodiment, the LVEF may be determined as described in the Guidelines, see citation above (McMurray, see e.g. page 1800 and following).

In an embodiment, the patient has an implanted cardioverter-defibrillator.

If diastolic dysfunction is graded, or if at least one structural or functional abnormality associated with diastolic dysfunction is graded, the patient to be tested shall suffer from said diastolic dysfunction or from said at least one structural or functional abnormality associated with diastolic dysfunction.

Preferably, the patient in accordance with the methods, uses, kits and devices of the present invention shall have (i.e. suffer from) left ventricular hypertrophy. Thus, the patient shall have an elevated left ventricular mass.

The term "left ventricular hypertrophy" is well known in the art. A detailed overview on left ventricular hypertrophy can be, e.g. found in standard text books (see Swamy Curr Cardiol Rep (2010) 12:277-282). LVH can be detected by electrocardiography, echocardiography, or cardiac magnetic resonance imaging (MRI). Preferably, LVH is detected by echocardiography. Moreover, criteria for the diagnosis of LVH are well known in the art (Mancia et al., European Heart J. 2007, 28: 1462, Die Innere Medizin: Referenzwerk für den Facharzt—Wolfgang Gerok—2007, page 293., Swamy Curr Cardiol Rep (2010) 12:277-282).

The diagnosis of LVH, preferably, includes measurements of the septum diameter, left ventricular posterial wall thickness and end diastolic diameter, with calculation of left ventricular mass according to formulae known in the art. Particularly preferred criteria for diagnosing LVH and for the determination of the left ventricular mass index are e.g. disclosed in the guidelines (Mancia et al., European Heart J. 2007, 28: 1462).

Preferably, the Cornell voltage criteria, the Cornell product criteria, the Sokolow-Lyon voltage criteria or the Romhilt-Estes point score system is/are used (Mancia et al., European Heart J. 2007, 28: 1462).

The term "left ventricular hypertrophy" (abbreviated "LVH") as used herein, preferably, relates to a thickening of the walls of the ventricles. LVH is, preferably, a response to a chronically increased workload on the heart. LVH is found in patients suffering from arterial hypertension is a disease requiring treatment.

Preferably, a male patient suffers from LVH, if the ratio of the left ventricular mass to body surface is larger than 112 $g/m^2$, or more preferably, if the ratio is larger than 125 $g/m^2$. Preferably, a female patient suffers from LVH if the ratio of the left ventricular mass to body surface is larger than 89 $g/m^2$, or more preferably, if the ratio is larger than 110 $g/m^2$. (see, e.g. Drazner M H, Dries D L, Peshock R M, Cooper R S, Klassen C, Kazi F, Willett D, Victor R G. Left ventricular hypertrophy is more prevalent in blacks than whites in the general population: The Dallas Heart Study. Hypertension. 2005; 46:124-129).

In an embodiment of the present invention, the patient who suffers from LVH has a left ventricular mass index of larger than 126 $g/m^2$. In another embodiment of the present invention, the patient has a left ventricular mass index of larger than 150 $g/m^2$.

In an embodiment, the patient in the context of the present invention does not have impaired renal function. Preferably, the patient shall not suffer from renal failure, in particular the patient shall not suffer from acute, chronic and/or end stage renal failure. Further, the patient, preferably, shall not suffer from renal hypertension. How to assess whether a patient exhibits impaired renal function is well known in the art. Renal disorders can be diagnosed by any means known and deemed appropriate. Particularly, renal function can be assessed by means of the glomerular filtration rate (GFR). For example, the GFR may be calculated by the Cockgroft-Gault or the MDRD formula (Levey 1999, Annals of Internal Medicine, 461-470). GFR is the volume of fluid filtered from the renal glomerular capillaries into the Bowman's capsule per unit time. Clinically, this is often used to determine renal function. The GFR was originally estimated (the GFR can never be determined, all calculations derived from formulas such as the Cockgroft Gault formula of the MDRD formula deliver only estimates and not the "real" GFR) by injecting inulin into the plasma. Since inulin is not reabsorbed by the kidney after glomerular filtration, its rate of excretion is directly proportional to the rate of filtration of water and solutes across the glomerular filter. In clinical practice however, creatinine clearance is used to measure GFR. Creatinine is an endogenous molecule, synthesized in the body, which is freely filtered by the glomerulus (but also secreted by the renal tubules in very small amounts). Creatinine clearance (CrCl) is therefore a close approximation of the GFR. The GFR is typically recorded in milliliters per minute (mL/min). The normal range of GFR for males is 97 to 137 mL/min, the normal range of GFR for females is 88 to 128 ml/min. Thus, it is particularly contemplated that the GFR of a patient who does not exhibit impaired renal function is within this range. Moreover, said patient preferably, has a blood creatinine level (in particular a serum creatinine level) of lower than 0.9 mg/dl, more preferably of lower than 1.1 mg/dl and most preferably of lower than 1.3 mg/dl.

The term "sample" refers to a sample of a body fluid, to a sample of separated cells or to a sample from a tissue or an organ. Samples of body fluids can be obtained by well-known techniques and include, samples of blood, plasma, serum, urine, lymphatic fluid, sputum, ascites, or any other bodily secretion or derivative thereof. Tissue or organ samples may be obtained from any tissue or organ by, e.g., biopsy. Separated cells may be obtained from the body fluids or the tissues or organs by separating techniques such as centrifugation or cell sorting. E.g., cell-, tissueor organ samples may be obtained from those cells, tissues or organs which express or produce the biomarker. The sample may be frozen, fresh, fixed (e.g. formalin fixed), centrifuged, and/or embedded (e.g. paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the level of the marker in the sample. Likewise, biopsies may also be subjected to post-collection preparative and storage techniques, e.g., fixation.

In a preferred embodiment, the sample is a blood, plasma or a serum sample.

The biomarker Insulin like growth factor binding protein 7 (IGFBP7) is well known in the art. The biomarker belongs to the Insulin like growth factor binding protein (IGFBP) system which plays an important role in cell growth and differentiation. The system comprises two ligands, IGF-I and IGF-II, two receptors, type 1 and type 2 IGF receptors, and as of 1995 six IGF-binding proteins (IGFBPs), IGFBP-1 to -6 (Jones, J. I., et al., Endocr. Rev. 16 (1995) 3-34). Recently the IGFBP family has been expanded to include the IGFBP-related proteins (IGFBP-rPs), which have significant structural similarities with the IGFBPs (Hwa, V., et al., Endocr. Rev 20 (1999) 761-787). Thus, the IGFBP superfamily includes the six conventional IGFBPs, which have high affinity for IGFs, and at least 10 IGFBP-rPs, which not only share the conserved amino-terminal domain of the IGFBPs but also show some degree of affinity for IGFs and insulin. The IGFBP-rPs are a group of cysteine-rich proteins that control diverse cellular functions, such as cellular growth, cell adhesion and migration, and synthesis of the extracellular matrix. In addition, these proteins might be involved in biological processes like tissue proliferation and differentiation, reproduction, angiogenesis, wound repair, inflammation, fibrosis, and tumorigenesis (Hwa, V., et al., Endocr. Rev 20 (1999)761-787).

IGF binding protein 7 (=IGFBP7) is a 30-kDa modular glycoprotein known to be secreted by endothelial cells, vascular smooth muscle cells, fibroblasts, and epithelial cells (Ono, Y., et al., Biochem Biophys Res Comm 202 (1994) 1490-1496). In the literature this molecule has also been denominated as FSTL2; IBP 7; IGF binding protein related protein I; IGFBP 7; IGFBP 7v; IGFBP rPl; IGFBP7; IGFB-PRP1; insulin like growth factor binding protein 7; insulin like growth factor binding protein 7 precursor; MAC25; MAC25 protein; PGI2 stimulating factor; and PSF or Prostacyclin stimulating factor. Northern blot studies revealed a wide expression of this gene in human tissues, including heart, brain, placenta, liver, skeletal muscle, and pancreas (Oh, Y., et al., J. Biol. Chem. 271 (1996) 30322-30325).

IGFBP7 was initially identified as a gene differentially expressed in normal leptomeningeal and mammary epithelial cells, compared with their counterpart tumor cells, and named meningiomaassociated cDNA (MAC25) (Burger, A. M., et al., Oncogene 16 (1998) 2459-2467). The expressed protein was independently purified as a tumor derived adhesion factor (later renamed angiomodulin) (Sprenger, C. C., et al., Cancer Res 59 (1999) 2370-2375) and as a prostacyclin stimulating factor (Akaogi, K., et al., Proc Natl Acad Sci USA 93 (1996) 8384-8389). It has additionally been reported as T1A12, a gene down-regulated in breast carcinomas (StCroix, B., et al., Science 289 (2000) 1197-1202).

Preferably, the term "IGFBP7" refers to human IGFBP7. The sequence of the protein is well known in the art and is e.g. accessible via GenBank (NP_001240764.1). IGFBP7 as used herein, preferably, encompasses also variants of the specific IGFBP7 polypeptides.

The term "measuring" the level of the biomarkers, in particular a polypeptide, as referred to herein refers to the quantification of the biomarker, e.g. to determining the level of the biomarker in the sample, employing appropriate methods of detection described elsewhere herein. The terms "measuring" and "determining" may be used interchangeably herein. The same applies to the terms "level" and "amount".

In an embodiment, the level of the biomarker is measured by contacting the sample with a detection agent that specifically binds to the respective marker, thereby forming a complex between the agent and said marker, detecting the level of complex formed, and thereby measuring the level of said marker.

The biomarkers as referred to herein can be detected using methods generally known in the art. Methods of detection generally encompass methods to quantify the level of a biomarker in the sample (quantitative method). Preferably, the biomarker is a polypeptide. It is generally known to the skilled artisan which of the following methods are suitable for qualitative and/or for quantitative detection of a biomarker. Samples can be conveniently assayed for, e.g., proteins using Westerns and immunoassays, like ELISAs, RIAs, fluorescence-based immunoassays, which are commercially available. Further suitable methods to detect biomarker include measuring a physical or chemical property specific for the peptide or polypeptide such as its precise molecular mass or NMR spectrum. Said methods comprise, e.g., biosensors, optical devices coupled to immunoassays, biochips, analytical devices such as mass-spectrometers, NMR-analyzers, or chromatography devices. Further, methods include microplate ELISA-based methods, fullyautomated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

For the detection of biomarker proteins as referred to herein a wide range of immunoassay techniques using such an assay format are available, see, e.g., U.S. Pat. Nos. 4,016,043, 4,424,279, and 4,018,653. These include both single-site and two-site or "sandwich" assays of the noncompetitive types, as well as in the traditional competitive binding assays. These assays also include direct binding of a labeled antibody to a target biomarker.

Sandwich assays are among the most useful and commonly used immunoassays.

Methods for measuring electrochemiluminescent phenomena are well-known. Such methods make use of the ability of special metal complexes to achieve, by means of oxidation, an excited state from which they decay to ground state, emitting electrochemiluminescence. For review see Richter, M. M., Chem. Rev. 104 (2004) 3003-3036.

Biomarkers can also be detected by generally known methods including magnetic resonance spectroscopy (NMR spectroscopy), Gas chromatography-mass spectrometry (GC-MS), Liquid chromatography-mass spectrometry (LC-MS), High and ultra-HPLC HPLC such as reverse phase HPLC, for example, ion-pairing HPLC with dual UV-wavelength detection, capillary electrophoresis with laser-induced fluorescence detection, anion exchange chromatography and fluorescent detection, thin layer chromatography.

Preferably, measuring the level of a biomarker as referred to herein comprises the steps of (a) contacting a cell capable of eliciting a cellular response the intensity of which is indicative of the level of the peptide or polypeptide with the said peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the level of the peptide or polypeptide.

Also preferably, measuring the level of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Measuring the level of a peptide or polypeptide may, preferably, comprises the steps of (a) contacting the peptide with a specific binding agent, (b) (optionally) removing non-bound binding agent, (c) measuring the level of bound binding agent, i.e. the complex of the binding agent formed in step (a). According to a preferred embodiment, said steps of contacting, removing and measuring may be performed by an analyzer unit of the system disclosed herein. According to some embodiments, said steps may be performed by a single analyzer unit of said system or by more than one analyzer unit in operable communication with each other. For example, according to a specific embodiment, said system disclosed herein may include a first analyzer unit for performing said steps of contacting and removing and a second analyzer unit, operably connected to said first analyzer unit by a transport unit (for example, a robotic arm), which performs said step of measuring.

The bound binding agent, i.e. the binding agent or the binding agent/peptide complex, will generate an intensity signal. Binding according to the present invention includes both covalent and non-covalent binding. A binding agent according to the present invention can be any compound, e.g., a peptide, polypeptide, nucleic acid, or small molecule, binding to the peptide or polypeptide described herein. Preferred binding agents include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such binding agents are well-known in the art. For example, identification and production of suitable antibodies or aptamers is also offered by commercial suppliers. The person skilled in the art is familiar with methods to develop derivatives of such binding agents with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the binding agent or agent binds specifically to the peptide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the binding agent can be measured by any method known in the art. Preferably, said method is semi-quantitative or quantitative. Further suitable techniques for the determination of a polypeptide or peptide are described in the following.

Binding of a binding agent may be measured directly, e.g. by NMR or surface plasmon resonance. Measurement of the binding of a binding agent, according to preferred embodiments, is performed by an analyzer unit of a system disclosed herein. Thereafter, a level of the measured binding may be calculated by a computing device of a system disclosed herein. If the binding agent also serves as a substrate of an enzymatic activity of the peptide or polypeptide of interest, an enzymatic reaction product may be measured (e.g. the level of a protease can be measured by measuring the level of cleaved substrate, e.g. on a Western Blot). Alternatively, the binding agent may exhibit enzymatic properties itself and the "binding agent/peptide or polypeptide" complex or the binding agent which was bound by the peptide or polypeptide, respectively, may be contacted with a suitable substrate allowing detection by the generation of an intensity signal. For measurement of enzymatic reaction products, preferably the level of substrate is saturating. The substrate may also be labeled with a detectable label prior to the reaction. Preferably, the sample is contacted with the substrate for an adequate period of time. An adequate period of time refers to the time necessary for a detectable, preferably measurable, level of product to be produced. Instead of measuring the level of product, the time necessary for appearance of a given (e.g. detectable) level of product can be measured. Third, the binding agent may be coupled covalently or non-covalently to a label allowing detection and measurement of the binding agent. Labeling may be done by direct or indirect methods. Direct labeling involves coupling of the label directly (covalently or non-covalently) to the binding agent. Indirect labeling involves binding (covalently or non-covalently) of a secondary binding agent to the first binding agent. The secondary binding agent should specifically bind to the first binding agent. Said secondary binding agent may be coupled with a suitable label and/or be the target (receptor) of tertiary binding agent binding to the secondary binding agent. The use of secondary, tertiary or even higher order binding agents is often used to increase the signal. Suitable secondary and higher order binding agents may include antibodies, secondary antibodies, and the well-known streptavidin-biotin system (Vector Laboratories, Inc.). The binding agent or substrate may also be "tagged" with one or more tags as known in the art. Such tags may then be targets for higher order binding agents. Suitable tags include biotin, digoxygenin, His-Tag, Gluta-thion-S-Transferase, FLAG, GFP, myctag, influenza A virus hae-magglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as readymade stock solution from Roche Diagnostics), CDP-Star™ (Amersham Bio-sciences), ECF™ (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. A radioactive label can be detected by any method known and appropriate, e.g. a light-sensitive film or a phosphor imager.

The level of a peptide or polypeptide may be, also preferably, determined as follows: (a) contacting a solid support comprising a binding agent for the peptide or polypeptide as specified above with a sample comprising the peptide or polypeptide and (b) measuring the level peptide or polypeptide which is bound to the support. The binding agent, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The binding agent or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said binding agent are well known and include, but are not limited to ionic, hydrophobic, covalent interactions and the like. It is also contemplated to use "suspension arrays" as arrays according to the present invention (No-lan 2002, Trends Biotechnol. 20(1):9-12). In such suspension arrays, the carrier, e.g. a microbead or microsphere, is present in suspension. The array consists of different microbeads or microspheres, possibly labeled, carrying different binding agents. Methods of producing such arrays, for example based on solid-phase chemistry and photo-labile protective groups, are generally known (U.S. Pat. No. 5,744,305).

In an embodiment of the present invention, the levels of the biomarkers as referred to herein are measured by using the assays described in the Examples section.

In another embodiment of the method of the present invention, the measurement in step a) and b) may be carried out by an analyzer unit, in particular by an analyzer unit as defined elsewhere herein.

The term "binding agent" or "detection agent" refers to a molecule that comprises a binding moiety which specifically binds the corresponding to the respective biomarker. Examples of "binding agent" or "detection agent" are a aptamer, antibody, antibody fragment, peptide, peptide nucleic acid (PNA) or chemical compound.

The term "specific binding" or "specifically bind" refers to a binding reaction wherein binding pair molecules exhibit a binding to each other under conditions where they do not significantly bind to other molecules.

The term "specific binding" or "specifically binds", when referring to a protein or peptide as a binding agent, refers to a binding reaction wherein a binding agent binds to the corresponding target molecule with an affinity of at least $10^{-7}$ M. The term "specific binding" or "specifically binds" preferably refers to an affinity of at least $10^{-8}$ M or even more preferred of at least $10^{-9}$ M for its target molecule. The term "specific" or "specifically" is used to indicate that other molecules present in the sample do not significantly bind to the binding agent specific for the target molecule. Preferably, the level of binding to a molecule other than the target molecule results in a binding affinity which is only 10% or less, more preferably only 5% or less of the affinity to the target molecule.

The term "specific binding" or "specifically binds", when referring to a nucleic acid as a binding agent, refers to a hybridization reaction wherein a binding agent or a probe contains a hybridizing region exactly or substantially complementary to the target sequence of interest. A hybridization assay carried out using the binding agent or probe under sufficiently stringent hybridization conditions enables the selective detection of the specific target sequence. The hybridizing region is preferably from about 10 to about 35 nucleotides in length, more preferably from about 15 to about 35 nucleotides in length. The use of modified bases or base analogues which affect the hybridization stability, which are well known in the art, may enable the use of shorter or longer probes with comparable stability. A binding agent or a probe can either consist entirely of the hybridizing region or can contain additional features which allow for the detection or immobilization of the probe, but which do not significantly alter the hybridization characteristics of the hybridizing region.

The term "specific binding" or "specifically binds", when referring to a nucleic acid aptamer as a binding agent, refers to a binding reaction wherein a nucleic acid aptamer binds to the corresponding target molecule with an affinity in the low nM to pM range.

Examples of "binding agents", "detection agents" or "agents" are a nucleic acid probe, nucleic acid primer, DNA molecule, RNA molecule, aptamer, antibody, antibody fragment, peptide, peptide nucleic acid (PNA) or chemical compound. A preferred agent is an antibody which specifically binds to the biomarker to be measured. The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. Preferably, the antibody is a polyclonal antibody. More preferably, the antibody is a monoclonal antibody.

Another binding agent that can be applied, in an aspect, may be an aptamere which specifically binds to the at least one marker in the sample. The term "specific binding" or "specifically binds", when referring to a nucleic acid aptamer as a binding agent, refers to a binding reaction wherein a nucleic acid aptamer binds to the corresponding target molecule with an affinity in the low nM to pM range.

In yet an aspect the, sample is removed from the complex formed between the binding agent and the at least one marker prior to the measurement of the level of formed complex. Accordingly, in an aspect, the binding agent may be immobilized on a solid support. In yet an aspect, the sample can be removed from the formed complex on the solid support by applying a washing solution. The formed complex shall be proportional to the level of the at least one marker present in the sample. It will be understood that the specificity and/or sensitivity of the binding agent to be applied defines the degree of proportion of at least one marker comprised in the sample which is capable of being specifically bound. Further details on how the determination can be carried out are also found elsewhere herein. The level of formed complex shall be transformed into a level of at least one marker reflecting the level indeed present in the sample. Such a level, in an aspect, may be essentially the level present in the sample or may be, in another aspect, an level which is a certain proportion thereof due to the relationship between the formed complex and the level present in the original sample.

The term "level" as used herein encompasses the absolute amount of a biomarker as referred to herein, the relative amount or concentration of the biomarkers as referred to herein as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response levels measured from biological read out systems in response to the peptides or intensity signals obtained from specifically bound ligands. It is to be understood that values correlating to the aforementioned levels or parameters can also be obtained by all standard mathematical operations.

The term "comparing" as used herein refers to comparing the level of the biomarker(s) in the sample from the individual or patient with the reference level of the biomarker(s) specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer assisted. Thus, the comparison may be carried out by a computing device (e.g., of a system disclosed herein). The value of the measured or detected level of the biomarker in the sample from the individual or patient and the reference level can be, e.g., compared to each other and the said comparison can be automatically carried out by a computer program executing an algorithm for the comparison. The computer program carrying out the said evaluation will provide the desired assessment in a suitable output format. For a computer assisted comparison, the value of the measured amount may be compared to values corresponding to suitable references which are stored in a database by a computer program. The computer program may further evaluate the result of the comparison, i.e. automatically provide the desired assessment in a suitable output format. For a computer assisted comparison, the value of the measured amount may be compared to values corresponding to suitable references which are stored in a database by a computer program. The computer program may further evaluate the result of the comparison, i.e. automatically provides the desired assessment in a suitable output format.

The level of the biomarker(s) as referred to herein shall be compared to a reference level (or to reference levels). The reference level as used herein, preferably, shall allow for diagnosing or grading a dysfunction or abnormality as referred to herein (i.e. diastolic dysfunction and/or structural or a functional abnormality associated with diastolic dysfunction), and thus for differentiating whether a patient suffers from said dysfunction or abnormality, or not (or from a mild or severe form thereof).

The reference amount may be used to define and establish a threshold level. The threshold level, preferably, allows grading/diagnosing a patient as described herein. Said diagnosis or grading may be provided by the computing device of a system disclosed herein based on said comparison of the calculated "level" to a reference or a threshold. For example, a computing device of a system may provide an indicator, in the form of a word, symbol, or numerical value which is indicative of the diagnosis or grading. The reference level applicable for an individual patient may vary depending on various physiological parameters such as age, gender, or subpopulation, as well as on the means used for the determination of the polypeptide or peptide referred to herein. A suitable reference level may be determined from a reference sample to be analyzed together, i.e. simultaneously or subsequently, with the test sample.

Reference levels can, in principle, be calculated for a cohort of patients suffering from a dysfunction or at least one abnormality (as referred to herein), or not suffering from said dysfunction or at least one abnormality as specified above based on the average or mean values for a given biomarker by applying standard statistically methods. In particular, accuracy of a test such as a method aiming to diagnose an event, or not, is best described by its receiver-operating characteristics (ROC) (see especially Zweig 1993, Clin. Chem. 39:561-577). The ROC graph is a plot of all of the sensitivity/specificity pairs resulting from continuously varying the decision threshold over the entire range of data observed. The clinical performance of a diagnostic method depends on its accuracy, i.e. its ability to correctly allocate patients to a certain assessment, prognosis or diagnosis. The ROC plot indicates the overlap between the two distributions by plotting the sensitivity versus 1-specificity for the complete range of thresholds suitable for making a distinction. On the y-axis is sensitivity, or the true-positive fraction, which is defined as the ratio of number of true-positive test results to the product of number of true-positive and number of falsenegative test results. This has also been referred to as positivity in the presence of a disease or condition. It is calculated solely from the affected subgroup. On the x-axis is the false-positive fraction, or 1-specificity, which is defined as the ratio of number of false-positive results to the product of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. Dependent on a desired confidence interval, a threshold can be derived from the ROC curve allowing for the diagnosis or prediction for a given event with a proper balance of sensitivity and specificity, respectively. Accordingly, the reference to be used for the aforementioned method of the present invention can be, preferably, a threshold or cut off amount and can be generated, preferably, by establishing a ROC for said cohort as described above and deriving a threshold amount therefrom. Dependent on a desired sensitivity and specificity for a diagnostic method, the ROC plot allows deriving suitable thresholds.

Reference levels are well known in the art and can be determined by the skilled person without further ado. In an embodiment, the term "reference level" herein refers to a predetermined value. As the skilled artisan will appreciate the reference level is predetermined and set to meet routine requirements in terms of e.g. specificity and/or sensitivity. These requirements can vary, e.g. from regulatory body to regulatory body. It may for example be that assay sensitivity or specificity, respectively, has to be set to certain limits, e.g. 80%, 90%, 95% or 98%, respectively. These requirements may also be defined in terms of positive or negative predictive values. Nonetheless, based on the teaching given in the present invention it will always be possible for a skilled artisan to arrive at the reference level meeting those requirements. Preferably, the reference level is derived patients suffering from a disease or abnormality as referred to herein (i.e. diastolic dysfunction and/or structural or a functional abnormality associated with diastolic dysfunction), or from a severe or mild form therefrom (in case the grading is done). Also preferably, the reference level is derived patients not suffering from a disease or abnormality as referred to herein (i.e. diastolic dysfunction and/or at least one structural or a functional abnormality associated with diastolic dysfunction), or from a severe or mild form thereof (in case the grading is done).

The reference level in one embodiment has been predetermined in reference samples from the disease entity to which the patient belongs. In certain embodiments the reference level can e.g. be set to any percentage between 25% and 75% of the overall distribution of the values in a disease entity investigated. In other embodiments the reference level can e.g. be set to the median, tertiles or quartiles as determined from the overall distribution of the values in reference samples from a disease entity investigated. In one embodiment the reference level is set to the median value as determined from the overall distribution of the values in a disease entity investigated. The reference level may vary depending on various physiological parameters such as age, gender or subpopulation, as well as on the means used for the determination of the IGFBP7 referred to herein. In one embodiment, the reference sample is from essentially the same type of cells, tissue, organ or body fluid source as the sample from the individual or patient subjected to the method of the invention, e.g. if according to the invention blood is used as a sample to determine the level of IGFBP7 in the individual, the reference level is also determined in blood or a part thereof.

It is to be understood that the reference level to be applied in connection with a diagnosis as referred to herein may be different from the reference level to be applied for a grading. E.g., the reference level for the diagnosis may be lower than for the grading. However, this will be taken into account by the skilled person. Thus, for diagnosing a diastolic dysfunction or at least one abnormality as referred to herein a reference level is applied which allows for diagnosing said diastolic dysfunction or said at least one abnormality, whereas for grading a diastolic dysfunction or at least one abnormality as a reference level is applied which allows for grading said diastolic dysfunction or said at least one abnormality.

Preferred reference levels for the IGFBP7 to be applied in accordance with the present invention are within a range of about 100 to 140 ng/ml, in particular about 110 to about 130 ng/ml, or about 115 to about 120 ng/ml. Depending on the applied assay for the determination of IGFBP7, the reference levels may differ. This will be taken into account by the skilled person.

Preferably, the term "about" as used herein encompasses a range of + and −20%, more preferably a range of + and −10%, even more preferably a range of + and −5%, and most preferably a range of + and −2%, relative to the specific amount, e.g., indication of an amount of "about 100" is meant to encompass an amount within a range from 80 to 120. Also, the term "about" refers to the exact amount. Preferably, the levels are measured as described in the Examples.

The following applies as diagnostic algorithm, in case a diagnosis is done. Preferably,
  a) a level of IGFBP7 above the reference level indicates that the patient suffers from diastolic dysfunction and/or said at least one structural or a functional abnormality associated with diastolic dysfunction, and/or
  b) a level of IGFBP7 below the reference level indicates that the patient does not suffer from diastolic dysfunction and/or said at least one structural or a functional abnormality associated with diastolic dysfunction.

The following applies as diagnostic algorithm, in case a grading is done. Preferably,
  a) a level of IGFBP7 above the reference level indicates that the patient suffers from a severe form diastolic dysfunction and/or a severe form of said at least one structural or functional abnormality associated with diastolic dysfunction, and/or
  b) a level of IGFBP7 below the reference level indicates that the patient suffers from a mild form of diastolic dysfunction and/or a mild form of said at least one structural or functional abnormality associated with diastolic dysfunction.

In certain embodiments, the term "above the reference level" refers to a level of the biomarker in the sample from the individual or patient above the reference level or to an overall increase of 5%, 10%, 20%, 25%, 30%, 40%, 50%, 60%, 70%, 80%, 85%, 90%, 95%, 100% or greater, determined by the methods described herein, as compared to the reference level. In certain embodiments, the term increase refers to the increase in biomarker level in the sample from the individual or patient wherein, the increase is at least about 1.5-, 1.75-, 2-, 3-, 4-, 5-, 6-, 7-, 8-, 9-, 10-, 15-, 20-, 25-, 30-, 40-, 50-, 60-, 70-, 75-, 80-, 90-, or 100-fold higher as compared to the reference level, e.g. predetermined from a reference sample.

In certain embodiments, the term "decrease" or "below" herein refers to a level of the biomarker in the sample from the individual or patient below the reference level or to an overall reduction of 5%, 10%, 20%, 25%, 30%, 40%, 50%, 60%, 70%, 80%, 85%, 90%, 95%, 96%, 97%, 98%, 99% or greater, determined by the methods described herein, as compared to the reference level. In certain embodiments, the term decrease in biomarker level in the sample from the individual or patient wherein the decreased level is at most about 0.9-, 0.8-, 0.7-, 0.6-, 0.5-, 0.4-, 0.3-, 0.2-, 0.1-, 0.05-, or 0.01-fold of the reference level, e.g. predetermined from a reference sample, or lower.

In an embodiment of the present invention, the level of at least one further biomarker is measured in a/the sample from the patient and compared to a (suitable) reference level (for said at least one further biomarker). In an embodiment, the at least one further marker is selected from the group consisting of Osteopontin, a cardiac Troponin, a BNP-type peptide, in particular NT-proBNP, Endostatin, Mimecan, uric acid, and GDF15 (Growth differentiation factor 15). The determination of at least one further biomarker allows for a more reliable assessment of diastolic dysfunction and/or at least one structural or functional abnormalities associated with diastolic dysfunction.

Accordingly, the present invention relates to a method for diagnosing and/or grading diastolic dysfunction and/or at least one structural or functional abnormality associated with diastolic dysfunction in a patient suffering from heart failure, said method comprising the steps of a) measuring the level of IGFBP7 (Insulin like growth factor binding protein 7), and the level(s) of at least one further marker selected from the group consisting of Osteopontin, a cardiac Troponin, a BNP-type peptide, in particular NT-proBNP, Endostatin, Mimecan, uric acid, and GDF15 in a sample from a patient suffering from heart failure, and b) comparing the level of IGFBP7 and the level(s) of at least one further biomarker measured in a) to a reference level.

Uric acid is the final product of purine metabolism in a subject organism. The IUPAC name is 7,9-dihydro-3H-purine-2,6,8-trione. The compound is frequently also referred to as urate, Lithic acid, 2,6,8-trioxypurine, 2,6,8-trihydroxypurine, 2,6,8-Trioxopurine, 1H-Purine-2,6,8-triol (compound formula $C_5H_4N_4O_3$, PubChem CID 1175, CAS number 69-93-2).

Uric acid measurements are used in the diagnosis and treatment of numerous renal and metabolic disorders, including renal failure, gout, leukemia, psoriasis, starvation or other wasting conditions, and of patients receiving cytotoxic drugs. The oxidation of uric acid provides the basis for two approaches to the quantitative determination of this purine metabolite. One approach is the reduction of phosphotungstic acid in an alkaline solution to tungsten blue, which is measured photometrically. A second approach, described by Praetorius and Poulson, utilizes the enzyme uricase to oxidize uric acid; this method eliminates the interferences intrinsic to chemical oxidation (Praetorius E, Poulsen H. Enzymatic Determination of Uric Acid with Detailed Directions. Scandinav J Clin Lab Investigation 1953; 3:273-280). Uricase can be employed in methods that involve the UV measurement of the consumption of uric acid or in combination with other enzymes to provide a colorimetric assay. Another method is the colorimetric method developed by Town et al. (Town M H, Gehm S, Hammer B, Ziegenhorn J. J Clin Chem Clin Biochem 1985; 23:591) The sample is initially incubated with a reagent mixture containing ascorbate oxidase and a clearing system. In this test system it is important that any ascorbic acid present in the sample is eliminated in the preliminary reaction; this precludes any ascorbic acid interference with the subsequent POD indicator reaction. Upon addition of the starter reagent, oxidation of uric acid by uricase begins. If the marker uric acid is measured, the detection agent that allows for measuring the marker may be an enzyme as set forth above. In this case the sample is contacted with said enzyme.

In the context of the present invention, uric acid can be determined by any method deemed appropriate. Preferably, the biomarker is determined by the aforementioned methods. More preferably, uric acid is determined by applying a slight modification of the colorimetric method described above. In this reaction, the peroxide reacts in the presence of peroxidase (POD), N-ethylN-(2-hydroxy-3-sulfopropyl)-3-methylaniline (TOOS), and 4-aminophenazone to form a quinone-diimine dye. The intensity of the red color formed is proportional to the uric acid concentration and is determined photometrically.

The term "cardiac Troponin" encompasses also variants of the aforementioned specific Troponins, i.e., preferably, of Troponin I, and more preferably, of Troponin T. Such variants have at least the same essential biological and immunological properties as the specific cardiac Troponins. In particular, they share the same essential biological and immunological properties if they are detectable by the same specific assays referred to in this specification, e.g., by ELISA Assays using polyclonal or monoclonal antibodies specifically recognizing the said cardiac Troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least about 50%, at least about 60%, at least about 70%, at least about 80%, at least about 85%, at least about 90%, at least about 92%, at least about 95%, at least about 97%, at least about 98%, or at least about 99% identical with the amino acid sequence of the specific Troponin. Variants may be allelic variants or any other species specific homologs, paralogs, or orthologs. Moreover, the variants referred to herein include fragments of the specific cardiac Troponins or the aforementioned types of variants as long as these fragments have the essential immunological and biological properties as referred to above. Preferably, the cardiac troponin variants have immunological properties (i.e. epitope composition) comparable to those of human troponin T or troponin I. Thus, the variants shall be recognizable by the aforementioned means or ligands used for determination of the concentration of the cardiac troponins. Thus, the variants shall be recognizable by the aforementioned means or ligands used for determination of the concentration of the cardiac troponins. Such fragments may be, e.g., degradation products of the Troponins. Further included are variants which differ due to posttranslational modifications such as phosphorylation or myristylation. Preferably the biological property of troponin I and its variant is the ability to inhibit actomyosin ATPase or to inhibit angiogenesis in vivo and in vitro, which may e.g. be detected based on the assay described by Moses et al. 1999 PNAS USA 96 (6): 2645-2650). Preferably the biological property of troponin T and its variant is the ability to form a complex with troponin C and I, to bind calcium ions or to bind to tropomyosin, preferably if present as a complex of troponin C, I and T or a complex formed by troponin C, troponin I and a variant of troponin T. It is known that low concentrations of circulating cardiac troponin may be detected in patients at various conditions, but further studies are required to understand their respective role and rate (Masson et al., Curr Heart Fail Rep (2010) 7:15-21).

The marker Endostatin is well known in the art. Endostatin was originally isolated from murine hemangioendothelioma as a 20 kDA proteolytic fragment of type XVIII collagen (O'Reilly, M. S. et al., Cell 88 (1997) 277-285). Collagens represent a family of extracellular matrix proteins with a characteristic triple-helical conformation forming supra-molecular aggregates that play a dominant role in maintaining tissue structural integrity. Excessive collagen deposition leads to fibrosis disrupting the normal functioning of surrounding tissues. Collagen XVIII is a member of the Multiplexin family of collagens with multiple interruptions in the central triple-helical domain and a unique non-triple-helical domain at the C-terminus mainly in basement membranes. The sequence of the short isoform of human type alpha 1-chain of collagen XVIII (SwissProt: P39060) is e.g. disclosed in WO2010/124821 which herewith is incorporated by reference with respect to its entire disclosure content.

Endostatin is released from the alpha 1 chain of collagen XVIII by action of various proteolytic enzymes (for details see Ortega, N. and Werb, Z., Journal of Cell Science 115 (2002) 4201-4214—the full disclosure of this paper is herewith incorporated by reference). Endostatin as used herein is represented by the collagen XVIII fragment spanning from amino acid position 1337 to amino acid position 1519 of collagen XVIII as disclosed in WO2010/124821. The hinge region at the C-terminus of the alpha chain of collagen XVIII contains several protease sensitive sites and a number of enzymes, including neutrophil elastase, cathepsins and matrix metalloproteinases are known to generate endostatin by cleaving the collagen chain in this region. These proteases do not exclusively release endostatin but also may release other, larger fragments that contain the endostatin sequence. As obvious to the skilled artisan such larger fragments will also be measured by an immunoassay for endostatin.

Endostatin is a potent inhibitor of angiogenesis and blood vessel growth. The relationship between endostatin and cytokine networks is undetermined, but it is known that endostatin is able to alter expression of a wide range of genes (Abdollahi, A. et al., Mol. Cell 13 (2004) 649-663).

Endostatin as used herein, preferably, encompasses also variants of the specific endostatin polypeptides. For an explanation of the term "variants", please see above.

Mimecan is a small proteoglycan with leucin-rich repeats and a precursor comprising 298 amino acids. Other names of mimecan are OGN, osteoglycin, OG, OIF, SLRR3A.

Mimecan is a member of the secreted small leucine rich proteoglycans (SLRP) family with structurally related core proteins. The common feature shared by all SLRPs is the tandem leucine-rich repeat (LRR) units in the C-terminal half of the core protein. In the N-terminal region, however, each class of SLRP has a unique domain containing a cysteine cluster with conserved spacing called the LRR N-domain. Class III SLRPs contain six carboxyl LRRs and include mimecan, epiphycan and opticin.

Functional studies from mouse knockouts for class I and II members, such as decorin, biglycan, lumecan and fibromodulin, showed that the SLRP-deficient mice displayed a wide array of defects attributable to abnormal collagen fibrillogenesis suggesting that these SLRPs play important roles in establishing and maintaining the collagen matrix (Ameye, L. and Young, M. F., Glycobiology 12 (2002) 107R-116R). Deficiency of class III mimecan also caused collagen fibril abnormalities (Tasheva, E. S. et al., Mol. Vis. 8 (2002) 407-415).

Mimecan is a multifunctional component of the extracellular matrix. It binds to a variety of other proteins (IGF2, IKBKG, IFNB1, INSR, CHUK, IKBKB, NFKBIA, IL1 5, Cd3, retinoic acid, APP, TNF, lipopolysaccharide, c-abl oncogene 1, receptor tyrosine kinase, v-src sarcoma viral oncogene). These diverse binding activities may account for the ability of mimecan to exert diverse functions in many tissues.

Mimecan has been found in cornea, bone, skin and further tissues. Its expression pattern is altered in different pathological conditions. Despite the increasing amount of data on the biological role of mimecan its function is still not clear. Mimecan has been shown to be involved in regulating collagen fibrillogenesis, a process essential in development, tissue repair, and metastasis (Tasheva et al., Mol. Vis. 8 (2002) 407-415). It plays a role in bone formation in conjunction with TGF-beta-1 or TGF-beta-2.

The sequence of the human mimecan polypeptide is well known in the art and may be assessed, e.g., via GenBank accession number NP_054776.1 GI:7661704. Further, the sequence is disclosed in WO2011/012268. Mimecan as used herein, preferably, encompasses also variants of the specific mimecan polypeptides. For an explanation of the term "variants", please see above. In context of the present invention, mimecan is preferably determined as described in WO2011/012268.

Osteopontin (herein also referred to as "OPN"), also known as bone sialoprotein I (BSP-1 or BNSP), early T-lymphocyte activation (ETA-1), secreted phosphoprotein 1 (SPP1), 2ar and *Rickettsia* resistance (Ric), is a polypeptide which is a highly negatively charged, extracellular matrix protein that lacks an extensive secondary structure. It is composed of about 300 amino acids (297 in mouse; 314 in human) and is expressed as a 33-kDa nascent protein; there are also functionally important cleavage sites. OPN can go through posttranslational modifications which increase its apparent molecular weight to about 44 kDa. The sequence of osteopontin is well known in the art (human osteopontin: UniProt P10451, GenBank NP_000573.1) Osteopontin is found in normal plasma, urine, milk and bile (U.S. Pat. Nos. 6,414,219; 5,695,761; Denhardt, D. T. and Guo, X., FASEB J. 7 (1993) 1475-1482; Oldberg, A., et al., PNAS 83 (1986) 8819-8823; Oldberg, A., et al., J. Biol. Chem. 263 (1988) 19433-19436; Giachelli, C M., et al., Trends Cardiovasc. Med. 5 (1995) 88-95). The human OPN protein and cDNA have been isolated and sequenced (Kiefer M. C, et al., Nucl. Acids Res. 17 (1989) 3306). OPN functions in cell adhesion, chemotaxis, macrophage-directed interleukin-10. OPN is known to interact with a number of integrin receptors. Increased OPN expression has been reported in a number of human cancers, and its cognate receptors (av-b3, av-b5, and av-bl integrins and CD44) have been identified. In vitro studies by Irby, R. B., et al., Clin. Exp. Metastasis 21 (2004) 515-523 indicate that both endogenous OPN expression (via stable transfection) as well as exogenous OPN (added to culture medium) enhanced the motility and invasive capacity of human colon cancer cells in vitro.

The term "Growth-Differentiation Factor-15" or "GDF-15" relates to a polypeptide being a member of the transforming growth factor (TGF) cytokine superfamily. The terms polypeptide, peptide and protein are used interchangeable throughout this specification. GDF-15 was originally cloned as macrophage-inhibitory cytokine 1 and later also identified as placental transforming growth factor-15, placental bone morphogenetic protein, non-steroidal anti-inflammatory drugactivated gene 1, and prostate-derived factor (Bootcov loc cit; Hromas, 1997 Biochim Biophys Acta 1354:40-44; Lawton 1997, Gene 203:17-26; Yokoyama-Kobayashi 1997, J Biochem (Tokyo), 122:622-626; Paralkar 1998, J Biol Chem 273:13760-13767). Similar to other TGF-related cytokines, GDF-15 is synthesized as an inactive precursor protein, which undergoes disulfidelinked homodimerization. Upon proteolytic cleavage of the N terminal pro-peptide, GDF-15 is secreted as a ~28 kDa dimeric protein (Bauskin 2000, Embo J 19:2212-2220). Amino acid sequences for GDF-15 are disclosed in WO99/06445, WO00/70051, WO2005/113585, Bottner 1999, Gene 237: 105-111, Bootcov loc. cit, Tan loc. cit., Baek 2001, Mol Pharmacol 59: 901-908, Hromas loc cit, Paralkar loc cit, Morrish 1996, Placenta 17:431-441 or Yokoyama-Kobayashi loc cit. GDF-15 as used herein encompasses also variants of the aforementioned specific GDF-15 polypeptides.

As used herein, the term "BNP-type peptides" comprise pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP). Preferably, BNP-type peptides according to the present invention are NT-proBNP, BNP, and variants thereof. BNP is the active hormone and has a shorter half-life than the respective inactive counterpart NT-proBNP. BNP is metabolized in the blood, whereas NT-proBNP circulates in the blood as an intact molecule and as such is eliminated renally. The in-vivo half-life of NT-proBNP is 120 min longer than that of BNP, which is 20 min (Smith 2000, J Endocrinol. 167: 239-46.). Preanalytics are more robust with NT-proBNP allowing easy transportation of the sample to a central laboratory (Mueller 2004, Clin Chem Lab Med 42: 942-4.). Blood samples can be stored at room temperature for several days or may be mailed or shipped without recovery loss. In contrast, storage of BNP for 48 hours at room temperature or at 40 Celsius leads to a concentration loss of at least 20% (Mueller loc.cit.; Wu 2004, Clin Chem 50: 867-73.). Therefore, depending on the time-course or properties of interest, either measurement of the active or the inactive forms of the natriuretic peptide can be advantageous. The most preferred natriuretic peptides according to the present invention are NT-proBNP or variants thereof. As briefly discussed above, the human NT-proBNP, as referred to in accordance with the present invention, is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913 or Bonow loc. cit. Preferably, human NT-proBNP as used herein is human NT-proBNP as disclosed in EP 0 648 228 B 1. These prior art documents are herewith incorporated by reference with respect to the specific sequences of NT-proBNP and variants thereof disclosed therein. The NT-proBNP referred to in accordance with the present invention further encompasses allelic and other variants of said specific sequence for human NT-proBNP discussed above. Specifically, envisaged are variant polypeptides which are on the amino acid level preferably, at least 50%, 60%, 70%, 80%, 85%, 90%, 92%, 95%, 97%, 98%, or 99% identical to human NT-proBNP, preferably over the entire length of human NT-proBNP. The degree of identity between two amino acid sequences can be determined as described above.

Preferred combinations of two biomarkers (i.e. of IGFBP7 and a further biomarker) are disclosed in Example 2 below.

Further, the following combinations are useful:
IGFBP7+a cardiac Troponin
IGFBP7+a BNP-type peptide
IGFBP-7+Mimecan or Osteopontin
IGFBP7+Endostatin As shown in Example 2, the aforementioned markers showed a particular strong correlation to E/E' but also to other parameters.

A combination of IGFBP-7 and a cardiac Troponin (such as Troponin T) and/or GDF15 and/or uric acid may be used for grading/diagnosing diastolic dysfunction and several abnormalities as referred to herein.

Further, it is advantageous to combine IGFBP7 and uric acid for the abnormalities increased LA size, increased LAVi and/or increased transmitral E/A ratio.

Further, it is advantageous to combine IGFBP7 and GDF15 for the abnormalities increased LA size and/or increased E peak velocity.

Further preferred combinations of markers with IGFBP7, in particular for certain abnormalities (for patients with reduced and preserved LVEF, are disclosed in Example 2 (see 2.1 and 2.2).

The following applies as diagnostic algorithm, in case a diagnosis is done. Preferably,
a) a level of IGFBP7 above the reference level and a level (or levels) of the at least one further biomarker above the reference level(s) for said at least one biomarker indicate(s) that the patient suffers from diastolic dysfunction and/or said at least one structural or a functional abnormality associated with diastolic dysfunction, and/or
b) a level of IGFBP7 below the reference level and a level (or levels) of the at least one further biomarker below the reference level(s) for said at least one biomarker indicate(s) that the patient does not suffer from diastolic dysfunction and/or said at least one structural or a functional abnormality associated with diastolic dysfunction.

The following applies as diagnostic algorithm, in case a grading is done. Preferably,
a) a level of IGFBP7 above the reference level and a level (or levels) of the at least one further biomarker above the reference level(s) for said at least one biomarker indicate(s) that the patient suffers from a severe form diastolic dysfunction and/or a severe form of said at least one structural or functional abnormality associated with diastolic dysfunction, and/or
b) a level of IGFBP7 below the reference level and a level (or levels) of the at least one further biomarker below the reference level(s) for said at least one biomarker indicate(s) that the patient suffers from a mild form of diastolic dysfunction and/or a mild form of said at least one structural or functional abnormality associated with diastolic dysfunction.

Suitable reference levels for the further biomarkers can be determined as described herein above (for IGFBP7).

The following table A provides preferred ranges for reference levels (third column) for the various markers as well as preferred specific reference levels (fourth column). The person skilled in the art can determine further reference levels without further ado.

TABLE A

| Marker/Parameter | Unit | reference level within the range of from | reference level |
| --- | --- | --- | --- |
| Uric Acid | mg/dL | about 9 to 10 | about 9.1 |
| GFD-15 | pg/mL | about 2500 to 5000 | about 3210 |
| Endostatin | ng/mL | about 230 to 277 | about 243 |
| Mimecan | ng/mL | about 39 to 50 | about 45.2 |
| Osteopontin | ng/mL | about 110 to 120 | about 113.5 |

In a preferred embodiment of the methods of the present invention, said methods further comprise the step of recommending, selecting, continuing and/or initiating a suitable therapy, if according to the method of the present invention the patient suffers from diastolic dysfunction and/or at least one structural or functional abnormality associated with diastolic dysfunction (or from a severe form thereof).

The phrase "recommending a therapy" as used herein refers to using the information or data generated relating to the levels of the biomarkers as referred in accordance with the present invention in a sample of a patient for recommending a suitable therapy. The suitable therapy may be any therapy that allows for treating a diastolic dysfunction and/or at least one structural or functional abnormality associated with diastolic dysfunction (or a severe form thereof). Such therapies are e.g. described by Zouein et al. J Cardiovasc Pharmacol. Volume 62, Number 1, July 2013, page 13 to 16. In an embodiment, the therapy is administration of at least one Spironolactone. In another embodiment, the therapy is administration of Sildenafil or of Anakinra.

If the patient is diagnosed to suffer from diastolic dysfunction and/or at least one structural or functional abnormality associated with diastolic dysfunction (or is graded as to suffer from a severe form thereof), the patient is eligible to said therapy. In this case said therapy is selected, initiated, recommended, and/or continued.

Thus, the present invention relates to a method of treating a patient suffering from heart failure, comprising
 a) measuring the level of IGFBP7, and optionally the level(s) of at least one further marker selected from the group consisting of Osteopontin, a cardiac Troponin, a BNP-type peptide, in particular NT-proBNP, Endostatin, Mimecan, uric acid, and GDF15 in a sample from patient suffering from heart failure (as defined herein above),
 b) comparing the level(s) as measured in step a) to a suitable reference level (or to suitable reference levels), and
 c) identifying or selecting a patient as being eligible to a therapy that allows for treating diastolic dysfunction and/or at least one structural or functional abnormality associated with diastolic dysfunction (or a severe form thereof), in particular based on the results of the comparison step b), and
 d) selecting, initiating, recommending and/or continuing said therapy.

The phrase "selecting a patient" or "identifying a patient" as used herein refers to using the information or data generated relating to the level of IGFBP7 (and optionally of the further marker) in a sample of a patient to identify or selecting the patient as more likely to benefit or less likely to benefit from a therapy that allows for the treatment of diastolic dysfunction and/or at least one structural or functional abnormality associated with diastolic dysfunction. The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of IGFBP7 (and optionally of a further biomarker) to a reference level.

The phrase "selecting a therapy" as used herein refers to using the information or data generated relating to the level of IGFBP7 (and optionally of the further marker) in a sample of a patient to identify or selecting a therapy as set forth above for a patient. In some embodiments the phrase "identifying/selecting a therapy" includes the identification of a patient who requires adaptation of an effective amount of drug being administered.

All definitions and explanations given herein above and in the claims apply mutatis mutandis to the following methods, uses, kits and devices (except if stated otherwise).

Further, the present invention relates to a method, in particular an in vitro method, for monitoring i) diastolic function and/or ii) at least one parameter of diastolic function or iii) heart failure therapy in a patient suffering from heart failure, said method comprising the steps of
 a) measuring the level of the biomarker IGFBP7 (Insulin like growth factor binding protein 7) and, optionally, at least one further biomarker selected from the group consisting of Osteopontin, a cardiac Troponin, a BNP-type peptide, in particular NT-proBNP, Endostatin, Mimecan, uric acid, and GDF15 (Growth differentiation factor 15) in first and in a second sample from a patient suffering from heart failure, in particular in a patient with reduced left ventricular ejection fraction (LVEF), and
 b) comparing the level of the biomarker IGFBP7, and optionally the level of said at least one further biomarker measured the second sample to the level in the first sample.

In an embodiment, the method further comprises step c) of monitoring or providing a monitoring of i) diastolic function and/or ii) at least one parameter of diastolic function or iii) heart failure therapy, in particular based on the results of the comparison step b).

The term "heart failure" has been defined herein above. The definition applies accordingly.

In an embodiment of the aforementioned method, the heart failure patient shall suffer from diastolic dysfunction and/or at least one functional or structural abnormality of the heart associated with diastolic dysfunction. In an embodiment, the parameter underlying said abnormality is monitored. Further, as outlined above, the patient preferably has a reduced LVEF.

The term "monitoring diastolic function" or "monitoring at least one parameter of diastolic function" refers to keeping track of diastolic function or of at least one parameter of diastolic function. In particular, the term refers to assessing whether diastolic function of a parameter thereof improves or deteriorates. The term "monitoring heart failure therapy" as used herein refers to assessing whether a patient who receives heart failure therapy responds to said therapy, or not. A patient who responds to said therapy is a patient whose condition improves as a consequence of said therapy, whereas a patient who does not respond to said therapy is a patient whose condition does not improve as a consequence of said therapy. If the patient responds to said therapy, the therapy can be continued, whereas the therapy shall be discontinued or adapted if the patient does not respond to said therapy.

As will be understood by those skilled in the art, such assessments are usually not intended to be correct for 100% of the patients to be monitored. The term, however, requires that the assessment is correct for a statistically significant portion of the patients (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

The term "diastolic function" is well known in the art. In an embodiment, the term refers to the ability of the heart to fill during diastole. Preferred parameters of diastolic function are the parameters determined in the Examples section (see e.g. Example 1 and/or table 2 of the Examples section, in particular in section C, but also in section B, D, and E. Of the parameters shown in table 2, those parameters with a low p-value are particularly preferred.

Preferably, the parameter of diastolic function is selected from the group consisting of left atrial size (preferably, left atrial superior-inferior diameter), left atrial volume index, E peak velocity (i.e. transmitral Doppler E wave velocity), A peak velocity (i.e. lower transmitral Doppler A wave velocity), transmitral E/A ratio, mitral inflow E velocity to tissue Doppler E' velocity ratio (i.e. increased E/E' ratio), E'/A' ratio, pulmonary vein systolic peak velocity, pulmonary vein diastolic peak velocity, pulmonary vein systolic/diastolic ratio, increased right ventricular area, right ventricular systolic pressure (RVSP), right ventricular dilation, and right atrium size (preferably the right atrial superior-inferior diameter). Also preferably, the parameter is mitral regurgitation or tricuspid regurgitation.

The heart failure therapy to be monitored may be any therapy that allows for the treatment of heart failure. In particular, said therapy may be any therapy that allows for treating a diastolic dysfunction and/or at least one structural or functional abnormality associated with diastolic dysfunction as outlined in connection with the method of treatment elsewhere herein. The heart failure patient to be monitored preferably suffers from diastolic dysfunction.

Alternatively, the heart failure therapy may be a therapy that is tested as therapy for heart failure (in particular a therapy for diastolic dysfunction). Accordingly, the biomarker IGFBP7 (and optionally the at least one further biomarker as described herein) may be used in a heart failure patient (in particular a patient with diastolic dysfunction) in order to identify a compound capable of treating heart failure and/or diastolic dysfunction. A reduction of the IGFBP7 level (an optionally of the level of the at least one further biomarker) in a sample from the patient treated with said compound is indicative of a compound being capable of treating heart failure and/or diastolic dysfunction.

The "first sample" can obtained at any time from the patient who suffers from heart failure. If heart failure treatment is monitored, the first sample can be obtained before initiation of heart failure treatment (such as within one week before initiation of heart failure treatment), or during heart failure treatment.

The "second sample" is, preferably, understood as a sample which is obtained in order to reflect a change of the level of the respective marker as compared to the level of the respective marker in the first sample. The second sample shall be obtained after the first sample. Preferably, the second sample is obtained within about one month to about twelve months, more preferably within about two months to eight months, and most preferably within about three months to six months after said first sample. Also preferably, the second sample is obtained at least three months, or at least six months after said first sample.

Preferably, at least one further sample (i.e. a third sample, a fourth sample etc.) is obtained in order to further monitor the change of the level of a biomarker referred to herein. Such a further sample may be obtained, preferably, within about one month to about twelve months, more preferably within about two months to eight months, and most preferably within about three months to six months after the previous sample (e.g. the second sample).

An increase of the level of IGFBP7 (and of the at least one further biomarker, if measured) in the second sample (or in further samples) from the patient as compared to the first sample is indicative of deterioration of diastolic function and/or of deterioration of said at least one parameter of diastolic function.

Also preferably, an increase of the level of IGFBP7 (and of the at least one further biomarker, if measured) in the second sample (or in further samples) from the patient as compared to the first sample is indicative for a patient who does not respond to heart failure therapy.

A decrease of the level of IGFBP7 (and of the at least one further biomarker, if measured) in the second sample (or in further samples) from the patient as compared to the first sample is indicative of improvement of diastolic function and/or of said at least one parameter of diastolic function.

Also preferably, a decrease of the level of IGFBP7 (and of the at least one further biomarker, if measured) in the second sample (or in further samples) from the patient as compared to the first sample is indicative for a patient who does respond to heart failure therapy.

Particularly, a significant increase (or decrease) is an increase (or decrease) of a size which is considered to be significant for monitoring, particularly statistically significant. The terms "significant" and "statistically significant" are known to the person skilled in the art. Whether an increase (or a decrease) is statistically significant can be determined without further ado by the person skilled in the art using various well known statistic evaluation tools including those referred to herein.

Preferred increases of the level of IGFBP7 (and of the at least one further biomarker) which have been found in the course of the invention to be indicative of i) deterioration of diastolic function and/or of at least one parameter of diastolic function, or of ii) a patient who does not respond to heart failure therapy are listed herein below.

Preferably, an increase of the level of IGFBP7 (and of the at least one further biomarker, if measured) in the second sample compared to the level in the first sample, preferably, of at least 3%, more preferably of at least 5%, and even more preferably, of at least 7%, and most preferably of at least 10%, or even 20% is considered to be significant and, thus, indicative of i) deterioration of diastolic function and/or of at least one parameter of diastolic function, or of ii) a patient who does not respond to heart failure therapy.

With respect to the absolute level, the following may apply: Preferably, an increase of the level of IGFBP7 in the second sample compared to the level in the first sample, preferably, of at least 4 ng/ml, more preferably of at least 7 ng/ml, and even, more preferably, of at least 10 ng/ml or, most preferably of at least 15 ng/ml is, considered to be significant and, thus, indicative of i) deterioration of diastolic function and/or of at least one parameter of diastolic function, or of ii) a patient who does not respond to heart failure therapy.

Preferred decreases of the level of IGFBP7 (and of the at least one further biomarker) which have been found in the course of the invention to be indicative of i) improvement of diastolic function and/or of at least one parameter of diastolic function, or of ii) a patient responds to heart failure therapy are listed herein below.

Preferably, a decrease of the level of IGFBP7 (and of the at least one further biomarker, if measured) in the second sample compared to the level in the first sample, preferably, of at least 3%; or more preferably of at least 5%; more preferably of at least 10% is considered, or most preferably at least 20% to be significant and, thus, indicative of i) improvement of diastolic function and/or of at least one parameter of diastolic function, or of ii) a patient who responds to heart failure therapy.

With respect to the absolute level the following may apply: Preferably, a decrease of the level of IGFBP7 in the second sample compared to the level in the first sample, preferably, of at least 4 ng/ml, more preferably of at least 5 ng/ml, and even, more preferably, of at least 10 ng/ml most preferably of at least 15 ng/ml is, considered to be significant and, thus, indicative of i) improvement of diastolic function and/or of at least one parameter of diastolic function, or of ii) a patient who responds to heart failure therapy.

In an embodiment of the aforementioned method, the level of the biomarker IGFBP7 (and optionally of the at least one further biomarker) is measured in a series of samples obtained in intervals from the patient. In this case, the level of the measured biomarker(s) is compared to a reference level (reference levels) in a step b). Further, the percentage of time spent above the reference level is calculated for the biomarker(s).

Accordingly, the present invention relates to a method, in particular an in vitro method, for monitoring i) diastolic function and/or ii) at least one parameter of diastolic function or iii) heart failure therapy in a patient suffering from heart failure, said method comprising the steps of
a) measuring the level of the biomarker IGFBP7 (Insulin like growth factor binding protein 7) and, optionally at least one further biomarker selected from the group consisting of Osteopontin, a cardiac Troponin, a BNP-type peptide, in particular NT-proBNP, Endostatin, Mimecan, uric acid, and GDF15 (Growth differentiation factor 15) in a series of samples obtained in intervals from a patient suffering from heart failure, in particular in a patient with reduced left ventricular ejection fraction (LVEF),
b) comparing the level of the biomarker IGFBP7, and optionally the level of said at least one further biomarker measured in said samples to a reference level, and
c) calculating the percentage of time spent above the reference level for the biomarker IGFBP7, and optionally for said at least one further biomarker, based on the results of step b).

The term "patient" has been defined elsewhere herein. As set forth above, the patient shall suffer from heart failure, Preferably, the patient has a reduced LVEF. However, it is further envisaged that the patient has a preserved LVEF (see elsewhere herein).

In accordance with the aforementioned method, the level of the biomarker IGFBP7 shall be determined in a series of samples, preferably in a series of the same type of samples such as in a series of blood, a series of serum, or a series of plasma samples. A series of samples, preferably, comprises at least four samples to at least 20 samples, or even more. More preferably, the series of samples comprises at least four, even more preferably at least six, or most preferably, at least eight samples.

The samples comprised by the series shall be obtained in intervals from said patient. Preferably, said samples are not obtained too early after each other. Accordingly, the intervals are, preferably, intervals of about at least one month, more preferably, of about at least two months, or most preferably, of about at least three months. Also preferably, said intervals range from about one month to about six months, more preferably said intervals range from about one month to about months, most preferably said intervals range from about two months to four months. In an embodiment, the intervals are intervals of about three months (e.g. +/−three weeks).

Preferably, the following applies as diagnostic algorithm. Preferably,
an elevated percentage of time spent above the reference level (for the measured biomarker(s)) is indicative for i) deterioration of diastolic function and/or for ii) deterioration of said at least one parameter of diastolic function, or for iii) a patient who does not respond to the therapy and/or
a decreased percentage of time spent above the reference level (for the measured biomarker(s)) is indicative for i) improvement of diastolic function and/or for ii) improvement of said at least one parameter of diastolic function, or for iii) a patient who does respond to the therapy.

The percentage of time spent above the reference is the percentage time spent above the reference with respect to the (entire) time from the first measurement to the last measurement of the biomarker(s).

The percentage is considered to be elevated/increased if it is a percentage of, preferably, more than 60%, more preferably, more than 70%, or most preferably, more than 80% (in particular of the entire test period). The percentage is considered to be decreased if it is a percentage of, preferably, less than 55%, more preferably, less than 50%, or most preferably, less than 40% (in particular of the entire test period).

The explanations given herein above apply mutatis mutandis to the following subject matter according to the present invention.

Moreover, the present invention relates to a method, in particular, an in vivo method predicting the risk of mortality and/or of a cardiovascular event in a patient suffering from heart failure, said method comprising the steps of
a) measuring the level of IGFBP7 (Insulin like growth factor binding protein 7) in a series of samples obtained in intervals from a patient suffering from heart failure, in particular wherein said patient has reduced left ventricular ejection fraction (LVEF),
b) comparing the level of IGFBP7 measured in said samples to a reference level, and
c) calculating the percentage of time spent above the reference level based on the results of step b).

The aforementioned method may comprise the further step d) of predicting or providing a prediction whether the patient is at risk of mortality and/or of a cardiovascular event.

The term "predicting" used herein refer patients to assessing the probability according to which a patient will die (e.g. mortality caused by the heart failure) and/or develop a cardiovascular event, preferably an acute cardiovascular event such as an acute coronary syndrome (ACS) within a defined time window (predictive window) in the future. The predictive window is an interval in which the patient will develop a cardiovascular event or will die according to the predicted probability. The predictive window may be the entire remaining lifespan of the patient upon analysis by the method of the present invention. Preferably, however, the predictive window is an interval of one, two, three, four, five, ten, fifteen or 20 years after the method of the present invention has been carried out (more preferably and precisely, after the sample to be analyzed by the method of the present invention has been obtained). Most preferably, said predictive window is an interval of one year or five years. The predictive window may be one year for patients with reduced LVEF and five years for patients with preserved LVEF. As will be understood by those skilled in the art, such an assessment is usually not intended to be correct for 100% of the patients to be analyzed. The term, however, requires that the assessment will be valid for a statistically significant portion of the patients to be analyzed. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the prediction will be correct for at least 60%, at least 70%, at least 80%, or at least 90% of the patients of a given cohort.

The term "mortality" as used herein, preferably, relates to mortality from any cause, and, more preferably, from a cardiovascular event. The term "cardiovascular event" as used herein refers to any disorder of the cardiovascular system including preferably any acute cardiovascular event. Acute cardiovascular events are, preferably, stable angina pectoris (SAP) or acute coronary syndrome (ACS). ACS patients can show unstable angina pectoris (UAP) or myocardial infarction (MI). MI can be an ST-elevation MI (STEMI) or a non-ST-elevation MI (NSTEMI). NSTE-ACS as used herein encompasses UAP and NSTEMI. The occurring of an MI can be followed by a left ventricular dysfunction (LVD), development of heart failure or even mortality. Further preferred cardiovascular events encompass cardiac brady- or tachyarrhythmias including sudden cardiac death and stroke (cerebrovascular events or accidents). Also, mortality can also refer to the death rate or the ratio of number of deaths to a given population of patients.

The expression "predicting the risk of mortality and/or of a cardiovascular event" as used herein means that the patient to be analyzed by the method of the present invention is allocated either into the group of patients of a population having an elevated risk, or into a group having a reduced risk. An elevated risk as referred to in accordance with the present invention, preferably, means that the risk of developing a cardiovascular event or the risk of mortality within a predetermined predictive window is elevated significantly (i.e. increased significantly) for a patient with respect to the average risk for a cardiovascular event or cardiac mortality in a population of patients. A reduced risk as referred to in accordance with the present invention, preferably, means that the risk of developing a cardiovascular event or the risk of mortality within a predetermined predictive window is reduced significantly for a patient with respect to the average risk for a cardiovascular event or cardiac mortality in a population of patients. Particularly, a significant increase or reduction of a risk is an increase or reduction or a risk of a size which is considered to be significant for prognosis, particularly said increase or reduction is considered statistically significant. The terms "significant" and "statistically significant" are known by the person skilled in the art. Thus, whether an increase or reduction of a risk is significant or statistically significant can be determined without further ado by the person skilled in the art using various well known statistic evaluation tools.

Preferably, for a predictive window of five years, an elevated risk of mortality (or of a cardiovascular event) is within the range of 8.0% and 19.0%, more preferably within the range of 12.0% to 17.0%, most preferably, within the range of 8.0% to 16.0%. An elevated, and, thus increased risk of mortality as used herein, preferably, relates to a risk of more than 8.0%, preferably, more than 12.0%, more preferably, more than 17%, even more preferably, more than 20%, preferably, with respect to a predictive window of one or five years. A reduced risk of mortality (or of a cardiovascular event) as used herein, preferably, relates to a risk of less than 8.0%, preferably, less than 6%, even more preferably, less than 4%, and is, most preferably within the range of 3.0% and 8.0%, preferably with respect to a predictive window of one or five years.

Preferably, the following applies as diagnostic algorithm. Preferably,
 i) an elevated percentage of time spent above the reference level is indicative for a patient being at elevated risk of mortality and/or of a cardiovascular event and/or
 ii) a decreased percentage of time spent above the reference level is indicative for a patient being at reduced risk of mortality and/or of a cardiovascular event.

The definitions and explanations given above apply also to the following uses, kits and devices.

The present invention also relates to the use of
 i) the biomarker IGFBP7, or
 ii) an agent which allows for measuring the level of IGFBP7, in particular an agent which specifically binds to IGFBP7 (such as an antibody), and optionally
 iii) at least one further biomarker selected from the group consisting of Osteopontin, a cardiac Troponin, a BNP-type peptide, in particular NT-proBNP, Endostatin, Mimecan, uric acid, and GDF15 (Growth differentiation factor 15), or
 iv) at least one agent which allows for measuring the level of said at least one further biomarker, in particular an agent which specifically binds to said at least one further biomarker,
in a sample from a patient suffering from heart failure for diagnosing and/or grading diastolic dysfunction and/or at least one structural or functional abnormality associated with diastolic dysfunction, or
in a first and a second sample, or in a series of samples obtained in intervals, from a patient suffering from heart failure for monitoring i) diastolic function, and/or ii) at least one parameter of diastolic function, or iii) heart failure therapy.

The present invention also relates to the use of
 i) the biomarker IGFBP7, and/or
 ii) an agent which allows for measuring the level of IGFBP7, in particular an agent which specifically binds to IGFBP7 (such as an antibody), and optionally
 iii) at least one further biomarker selected from the group consisting of Osteopontin, a cardiac Troponin, a BNP-type peptide, in particular NT-proBNP, Endostatin, Mimecan, uric acid, and GDF15 (Growth differentiation factor 15), or
 iv) at least one agent which allows for measuring the level of said at least one further biomarker, in particular an agent which specifically binds to said at least one further biomarker,
for the manufacture of a diagnostic composition for diagnosing and/or grading diastolic dysfunction and/or at least one structural or functional abnormality associated with diastolic dysfunction, or
for the manufacture of a diagnostic composition for monitoring i) diastolic function, and/or ii) at least one parameter of diastolic function, or iii) heart failure therapy in a patient suffering from heart failure.

As set forth elsewhere herein, the patient may have a reduced LVEF.

Preferably, the agent is an antibody which specifically binds said marker. More preferably, said antibody is a polyclonal antibody, or in particular a monoclonal antibody. However, other agents may be applied as well (see e.g. the marker definitions).

According to a preferred embodiment of the present invention, a device adapted for carrying out a method of the invention is provided, said device comprising
  a. an analyzer unit comprising an agent which specifically binds to the biomarker IGFBP7, and optionally an agent (agents) which allow(s) for measuring the level of at least one further biomarker selected from the group consisting of Osteopontin, a cardiac Troponin, a BNP-type peptide, in particular NT-proBNP, Endostatin, Mimecan, uric acid, and GDF15, in particular an agent which specifically binds to said at least one further biomarker, said unit being adapted for measuring the level(s) of the biomarker(s) in a sample from a patient who suffers from heart failure; and
  b. an analyzer unit (or evaluation unit) for comparing the measured level(s) with reference level(s), whereby diastolic dysfunction and/or at least one structural or functional abnormality associated with diastolic dysfunction is diagnosed or graded, said unit comprising a database with reference level(s), and an algorithm for carrying out the comparison.

According to another preferred embodiment of the present invention, a device adapted for carrying out a method of the invention is provided comprising
  a. an analyzer unit comprising an agent which specifically binds to the biomarker IGFBP7, and optionally an agent which allows for measuring the level of at least one further biomarker selected from the group consisting of Osteopontin, a cardiac Troponin, a BNP-type peptide, in particular NT-proBNP, Endostatin, Mimecan, uric acid, and GDF15, in particular an agent which specifically binds to said at least one further biomarker, said unit being adapted for measuring the level(s) of the biomarker(s) in a first and second sample from a patient who suffers from heart failure; and
  b. an analyzer unit (or evaluation unit) for comparing the measured level(s) in the second sample to the level(s) in the first sample, whereby i) diastolic function and/or ii) at least one parameter of diastolic function or iii) heart failure therapy in a patient suffering from heart failure is monitored, said unit comprising an algorithm for carrying out the comparison.

According to another preferred embodiment of the present invention, a device adapted for carrying out a method of the invention is provided comprising
  a. an analyzer unit comprising an agent which specifically binds to the biomarker IGFBP7, and optionally an agent which allows for measuring the level of at least one further biomarker selected from the group consisting of Osteopontin, a cardiac Troponin, a BNP-type peptide, in particular NT-proBNP, Endostatin, Mimecan, uric acid, and GDF15, in particular an agent which specifically binds to said at least one further biomarker, said unit being adapted for measuring the level(s) of the biomarker(s) in a series of samples obtained in intervals from a patient who suffers from heart failure; and
  b. an analyzer unit (or evaluation unit) for comparing the levels measured in the series of samples to a reference level (or to reference levels) and for calculating the percentage of time spent above the reference level(s), whereby i) diastolic function and/or ii) at least one parameter of diastolic function or iii) heart failure therapy in a patient suffering from heart failure is monitored, said unit comprising a database with reference level(s), and an algorithm for carrying out the comparison and/or calculation.

Preferably, the algorithm of the aforementioned devices is the diagnostic algorithm as set forth elsewhere herein (in connection with the respective methods). Preferably, the algorithm is a computer-implemented algorithm. Preferably, the analyzer unite comprises a computer comprising tangibly embedded a computer program code for carrying out the comparison Preferred reference levels are disclosed elsewhere herein. In an embodiment, the reference level(s) is (are) stored in a database comprised by the analyzer unit or evaluation unit.

In an embodiment, the agent is an agent that specifically binds to the respective biomarker such as an antibody.

The term "device" as used herein relates to a system comprising at least the aforementioned means operatively linked to each other as to practice the method of the present disclosure. Suitable means for determining the amounts of the markers of the disclosed methods, and means for carrying out the comparison are disclosed above in connection with the disclosed methods. How to link the means in an operating manner will depend on the type of means included in the device. For example, where an analysis unit for automatically measuring the level of the biomarker of the present disclosure is applied, the data obtained by said automatically operating analysis unit can be processed by, e.g., a computer as evaluation unit in order to obtain the desired results. In some embodiments, the means are comprised of a single device in such a case.

A preferred embodiment of the instant disclosure includes a system/device for carrying the method of present invention. Examples of systems/devices include clinical chemistry analyzers, coagulation chemistry analyzers, immunochemistry analyzers, urine analyzers, nucleic acid analyzers, used to detect the result of chemical or biological reactions or to monitor the progress of chemical or biological reactions. More specifically, exemplary systems of the instant disclosure may include Roche Elecsys™ Systems and Cobas® e Immunoassay Analyzers, Abbott Architect™ and Axsym™ Analyzers, Siemens Centaur™ and Immulite™ Analyzers, and Beckman Coulter UniCel™ and Acess™ Analyzers, or the like.

Embodiments of the system or device may include one or more analyzer units utilized for practicing the subject disclosure. The analyzer units of the system or device disclosed herein are in operable communication with the computing device disclosed herein through any of a wired connection, Bluetooth, LANS, or wireless signal, as are known. Additionally, according to the instant disclosure, an analyzer unit may comprise a stand-alone apparatus, or module within a larger instrument, which performs one or both of the detection, e.g. qualitative and/or quantitative evaluation of samples for diagnostic purpose. For example, an analyzer unit may perform or assist with the pipetting, dosing, mixing of samples and/or reagents. An analyzer unit may comprise a reagent holding unit for holding reagents to perform the assays. Reagents may be arranged for example in the form of containers or cassettes containing individual reagents or group of reagents, placed in appropriate receptacles or positions within a storage compartment or conveyor. Detection reagents may also be in immobilized form on a solid support which are contacted with the sample. Further, an analyzer unit may include a process and/or detection component which is optimizable for specific analysis.

According to some embodiments, an analyzer unit may be configured for optical detection of an analyte, for example a marker, with a sample. An exemplary analyzer unit configured for optical detection comprises a device configured for converting electro-magnetic energy into an electrical signal, which includes both single and multi-element or array optical detectors. According to the present disclosure, an optical detector is capable of monitoring an optical electro-magnetic signal and providing an electrical outlet signal or response signal relative to a baseline signal indicative of the presence and/or concentration of an analyte in a sample being located in an optical path. Such devices may also include, for example, photodiodes, including avalanche photodiodes, phototransistors, photoconductive detectors, linear sensor arrays, CCD detectors, CMOS detectors, including CMOS array detectors, photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrated circuit. Suitable prepreamplifiers include, for example, integrating, transimpedance, and current gain (current mirror) pre-amplifiers.

Additionally, one or more analyzer unit according to the instant disclosure may comprise a light source for emitting light. For example, a light source of an analyzer unit may consist of at least one light emitting element (such as a light emitting diode, an electric powered radiation source such as an incandescent lamp, an electroluminescent lamp, a gas discharge lamp, a high-intensity discharge lamp, a laser) for measuring analyte concentrations with a sample being tested or for enabling an energy transfer (for example, through florescent resonance energy transfer or catalyzing an enzyme).

Further, an analyzer unit of the system may include one or more incubation units (for example, for maintaining a sample or a reagent at a specified temperature or temperature range). In some embodiments, an analyzer unit may include a thermocycler, include a real-time thermocycler, for subjecting a sample to repeated temperature cycles and monitoring a change in the amount of an amplification product with the sample.

Additionally, an analyzer unit of the system disclosed herein may comprise, or be operationally connected to, a reaction vessel or cuvette feeding unit. Exemplary feeding units include liquid processing units, such as a pipetting unit, to deliver samples and/or reagents to the reaction vessels. The pipetting unit may comprise a reusable washable needle, e.g. a steel needle, or disposable pipette tips. The analyzer unit may further comprise one or more mixing units, for example a shaker to shake a cuvette comprising a liquid, or a mixing paddle to mix liquids in a cuvette, or reagent container.

It follows from the above that according to some embodiments of the instant disclosure, portions of some steps of methods disclosed and described herein may be performed by a computing device. A computing device may be a general purpose computer or a portable computing device, for example. It should also be understood that multiple computing devices may be used together, such as over a network or other methods of transferring data, for performing one or more steps of the methods disclosed herein. Exemplary computing devices include desktop computers, laptop computers, personal data assistants ("PDA"), such as BLACKBERRY brand devices, cellular devices, tablet computers, servers, and the like. In general, a computing device comprises a processor capable of executing a plurality of instructions (such as a program of software).

A computing device has access to a memory. A memory is a computer readable medium and may comprise a single storage device or multiple storage devices, located either locally with the computing device or accessible to the computing device across a network, for example. Computer-readable media may be any available media that can be accessed by the computing device and includes both volatile and non-volatile media. Further, computer readable-media may be one or both of removable and non-removable media. By way of example, and not limitation, computer-readable media may comprise computer storage media. Exemplary computer storage media includes, but is not limited to, RAM, ROM, EEPROM, flash memory or any other memory technology, CD-ROM, Digital Versatile Disk (DVD) or other optical disk storage, magnetic cassettes, magnetic tape, magnetic disk storage or other magnetic storage devices, or any other medium which can be used for storing a plurality of instructions capable of being accessed by the computing device and executed by the processor of the computing device.

According to embodiments of the instant disclosure, software may include instructions which, when executed by a processor of the computing device, may perform one or more steps of the methods disclosed herein. Some of the instructions may be adapted to produce signals that control operation of other machines and thus may operate through those control signals to transform materials far removed from the computer itself. These descriptions and representations are the means used by those skilled in the art of data processing, for example, to most effectively convey the substance of their work to others skilled in the art.

The plurality of instructions may also comprise an algorithm which is generally conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as values, characters, display data, numbers, or the like as a reference to the physical items or manifestations in which such signals are embodied or expressed. It should be borne in mind, however, that all of these and similar terms are to be associated with the appropriate physical quantities and are merely used here as convenient labels applied to these quantities. According to some embodiments of the instant disclosure, an algorithm for carrying out a comparison between a measured level of one or more markers disclosed herein, and a suitable reference, is embodied and performed by executing the instructions. The results may be given as output of parametric diagnostic raw data or as absolute or relative amounts. According to various embodiments of the system disclosed herein, a "diagnosis", "grading" or "monitoring" may be provided by the device disclosed herein based on said comparison of the calculated "amount" to a reference or a threshold.

The computing device comprised by the device may also have access to an output device. Exemplary output devices include fax machines, displays, printers, and files, for example. According to some embodiments of the present disclosure, a computing device may perform one or more steps of a method disclosed herein, and thereafter provide an output, via an output device, relating to a result, indication, ratio or other factor of the method.

Finally, the invention pertains to a kit preferably adapted for carrying out a method of the present invention comprising an agent which specifically binds to the biomarker IFGBP7, and, optionally, at least one agent which specifically binds a further biomarker selected from the group consisting of Osteopontin, a cardiac Troponin, a BNP-type peptide, in particular NT-proBNP, Endostatin, Mimecan, uric acid, and GDF15. Preferably, the kit further comprises reference standards for the biomarker(s) marker as well as instructions for carrying out the said method.

The term "kit" as used herein refers to a collection of the aforementioned components, preferably, provided in separately or within a single container. The container also comprises instructions for carrying out the method of the present invention. These instructions may be in the form of a manual or may be provided by a computer program code which is capable of carrying out the comparisons referred to in the methods of the present invention and to establish a diagnosis accordingly when implemented on a computer or a data processing device. The computer program code may be provided on a data storage medium or device such as a optical storage medium (e.g., a Compact Disc) or directly on a computer or data processing device. Further, the kit shall comprise at least one standard for a reference as defined herein above, i.e. a solution with a predefined level (levels) biomarker(s) to be measured representing a reference level (or reference levels) as set forth elsewhere herein.

In some embodiments, a kit disclosed herein includes at least one component or a packaged combination of components for practicing a disclosed method. By "packaged combination" it is meant that the kits provide a single package that contains a combination of one or more components, such as probes (for example, an antibody), controls, buffers, reagents (for example, conjugate and/or substrate) instructions, and the like, as disclosed herein. A kit containing a single container is also included within the definition of "packaged combination." In some embodiments, the kits include at least one probe, for example an antibody (having specific affinity for an epitope of a biomarker as disclosed herein. For example, the kits may include an antibody that is labelled with a fluorophore or an antibody that is a member of a fusion protein. In the kit, the probe may be immobilized, and may be immobilised in a specific conformation. For example, an immobilized probe may be provided in a kit to specifically bind target protein, to detect target protein in a sample, and/or to remove target protein from a sample.

According to some embodiments, kits include at least one probe, which may be immobilized, in at least one container. Kits may also include multiple probes, optionally immobilized, in one or more containers. For example, the multiple probes may be present in a single container or in separate containers, for example, wherein each container contains a single probe.

In some embodiments, a kit may include one or more non-immobilized probe and one or more solid support that does or does not include an immobilized probe. Some such embodiments may comprise some or all of the reagents and supplies needed for immobilizing one or more probes to the solid support, or some or all of the reagents and supplies needed for binding of immobilized probes to specific proteins within a sample.

In certain embodiments, a single probe (including multiple copies of the same probe) may be immobilized on a single solid support and provided in a single container. In other embodiments, two or more probes, each specific for a different target protein or a different form of a single target protein (such as a specific epitope), a provided in a single container. In some such embodiments, an immobilized probe may be provided in multiple different containers (e.g., in singleuse form), or multiple immobilized probes may be provided in multiple different containers. In further embodiments, the probes may be immobilized on multiple different type of solid supports. Any combination of immobilized probe(s) and container(s) is contemplated for the kits disclosed herein, and any combination thereof may be selected to achieve a suitable kit for a desired use.

A container of the kits may be any container that is suitable for packaging and/or containing one or more components disclosed herein, including for example probes (for example, an antibody), controls, buffers, and reagents (for example, conjugate and/or substrate). Suitable materials include, but are not limited to, glass, plastic, cardboard or other paper product, wood, metal, and any alloy thereof. In some embodiments, the container may completely encase an immobilized probe(s) or may simply cover the probe to minimize contamination by dust, oils, etc., and expose to light. In some further embodiments, he kits may comprise a single container or multiple containers, and where multiple containers are present, each container may be the same as all other containers, different than others, or different than some but not all other containers.

Finally, the present invention relates to at least one drug selected from a Spironolactone, Sildenafil, and Anakinra for use in treating diastolic dysfunction and/or at least one structural or a functional abnormality associated with diastolic dysfunction in a patient suffering from heart failure having a level, in particular a blood, serum or plasma level of the marker IGFBP7, and optionally of at least one further marker is selected from the group consisting of Osteopontin, a cardiac Troponin, a BNP-type peptide, in particular NT-proBNP, Endostatin, Mimecan, uric acid, and GDF15 above the reference level(s) for said marker(s).

All references referred to above are herewith incorporated by reference with respect to their entire disclosure content as well as their specific disclosure content explicitly referred to in the above description.

EXAMPLES

The invention will now be illustrated by the following Examples which are not intended to restrict or limit the scope of this invention.

Example 1: PROTECT Study Patients

Study Design and Patient Population

The study was approved by the Partners Healthcare Institutional Review Board and informed consent was obtained from all patients. The PROTECT study was a randomized, single-center, prospective proof-of-concept trial that compared standard heart failure care to NT-proBNP-guided care with a goal of reducing natriuretic peptide levels to ≤1000 pg/mL in patients with HF due to LVSD. Patients were followed up for one year with at minimum quarterly visits. The methods and results of the PROTECT study have been published previously (Bhardwaj et al., Design and methods of the pro-b type natriuretic peptide outpatient tailored chronic heart failure therapy (protect) study, *Am Heart J.* 2010; 159:532-538). The primary endpoint for the PROTECT study was a composite endpoint of CV events, including worsening HF, HF hospitalization, significant ventricular arrhythmia, acute coronary syndrome, cerebral ischemia, and cardiac death, as previously defined. Of the 151 patients enrolled in the PROTECT study, 124 had available FIG. 3 samples for serial IGFBP7 measurement and baseline echocardiographic studies. These 124 study subjects were seen during a mean follow up of 10 months, with a total of 882 office visits.

Biomarker Measurements

At each visit, blood was collected into vacuum tubes containing ethylene diaminotetraacetic acid, centrifuged, and serum was aliquotted into tubes and frozen at −80° C. prior to testing. IGFBP7 was measured using a novel sandwich immunoassay that was developed and validated using a microtiter plate prototype ELISA (Roche Diagnostics, Penzberg, Germany).

Echocardiography Protocol

Detailed two-dimensional transthoracic echocardiography (TTE) was performed at baseline and when possible at completion of the study, a mean of 10 months later. Echocardiographic measurements were obtained pertaining to chamber size and function for all 4 chambers (indexed for body surface area), valvular regurgitation severity, right ventricular systolic pressure (RVSP), as well as diastolic indices. These included transmitral Doppler flow (E wave velocity, A wave velocity, E/A ratio), septal mitral annular tissue Doppler velocities (E' velocity and A' velocity), and pulmonary vein flow velocities. For the purposes of this study, transmitral flow was further divided into E/A<1, E/A 1.0-1.5, and E/A>1.5. Filling pressures were considered to be elevated if E/E' was >15, and the pulmonary vein S/D ratio was considered abnormal if <1.0. Left atrial volume index (LAVi) was considered abnormal if >28 mL/m$^2$; (Lang et al., Recommendations for chamber quantification: A report from the American society of echocardiography's guidelines and standards committee and the chamber quantification writing group, developed in conjunction with the European association of echocardiography, a branch of the European society of cardiology, J Am Soc Echocardiogr. 2005; 18:1440-1463) right ventricular systolic pressure (RVSP) was considered elevated if above the median of the group (43 mm Hg). Interpretation of the ultrasounds was done by two readers (RBW and ALB) who were blinded to study assignment and biomarker results.

Statistical Analysis

All continuous variables are considered at mean±standard deviation for normally distributed values; non-normal variables were identified using the Kolmogorov-Smirnov test and expressed as medians and interquartile range (IQR). Comparisons of variables as a function of IGFBP7 concentrations were performed using the Student's T test or Mann Whitney U test, as appropriate. For continuous variables expressed in multiple categories, the Kruskal Wallis test was employed.

In an effort to better understand linear associations between IGFBP7 concentrations and other continuous variables, we first ln-transformed non-normal results, to achieve normality. Following this transformation, Spearman correlations were performed, with the p expressed accompanied by the corresponding P value. In an effort to provide graphical representation of the Spearman analyses, selected scatter plots were generated, demonstrating the line of fit and 95th percent confidence intervals. Following univariate correlations, we then examined the avail-able data for independent predictors of the dependent variable of IGFBP7 concentrations. To be included in the multivariable linear regression model, all candidate variables required a retention P value of 0.10 or less in univariate correlations. Variables included were those from baseline clinical characteristics, laboratory values, as well as echocardiographic results at baseline. Following the construction of the best fit linear model, β coefficients for each predictor of IGFBP7 were expressed.

Consistent with prior work, clinical categorizations were made based on an IGFBP7 level of 117.8 ng/mL (corresponding to the highest tertile of the group). Additionally, exploration of secular trends in IGFBP7 to predict change in diastolic function was based on time spent <117.8 ng/mL integrated over time in study. Lastly, the percent time spent with an IGFBP7<117.8 ng/mL was also used to analyze risk for adverse outcomes, using univariable followed by multivariable Cox Proportional Hazards, modeling the association with incidence of any CV events. The multivariable model adjusted for epidemiologically and clinically relevant risk factors including treatment arm allocation in PROTECT, age, sex, New York Heart Association (NYHA) class, left ventricular ejection fraction (LVEF), E/A, E/E', LAVi, and RVSP, as well as baseline estimated glomerular filtration rate and NT-proBNP.

Statistics were performed with PASW Version 17.0 (Chicago, Ill.) with all P values two-sided and considered significant if <0.05.

Results

Table 1 shows the baseline characteristics of the subjects in this present analysis. The average age was 63.4 years (+14.2 years) and 83.9% were male. Approximately half (50.8%) had an ischemic cause of HF, 58% of patients had implantable cardioverter-defibrillators, and just over half of the patients (54.8%) were either NYHA Class III or IV. The majority of patients were on β blockers or angiotensin converting enzyme (ACE) inhibitors/angiotensin receptor blockers (ARBs), whereas 40.3% were on aldosterone antagonists. The median baseline levels of NT-proBNP and IGFBP7 were 1964 pg/mL and 89.9 ng/mL, respectively, and the threshold of 117.8 ng/mL represented the highest tertile for the group.

TABLE 1

Baseline characteristics of study participants.

| Characteristic | |
|---|---:|
| Biomarker guided arm | 50% |
| Age, years; mean ± standard deviation | 63.4 ± 14.2 |
| NYHA Class III or IV (%) | 54.8% |
| Male gender (%) | 83.9% |
| Ischemic cause of HF (%) | 50.8% |
| Past medical history | |
| Hypertension (%) | 52.4% |
| Coronary artery disease (%) | 55.6% |
| Myocardial infarction (%) | 40.3% |
| Atrial fibrillation (%) | 38.7% |
| Ventricular tachycardia (%) | 28.2% |
| Obstructive airways disease (%) | 21.8% |
| Diabetes mellitus (%) | 34.7% |
| Tobacco use (past or present; %) | 40.1% |
| Implanted devices | |
| Cardioverter-defibrillator (%) | 58.1% |
| Biventricular pacemaker (%) | 32.4% |
| Medications at baseline | |
| ACE inhibitors (%) | 67.7% |
| Angiotensin receptor blocker (%) | 17.7% |
| β-blocker (%) | 96.8% |
| Mineralocorticoid receptor antagonist (%) | 40.3% |
| Loop diuretic (%) | 91.9% |
| Thiazide diuretic (%) | 4.0% |
| Digoxin (%) | 34.0% |
| Hydralazine (%) | 4.9% |

TABLE 1-continued

Baseline characteristics of study participants.

| | |
|---|---|
| Nitrate (%) | 15.3% |
| Statin (%) | 64.5% |
| Aspirin (%) | 86.4% |
| Physical examination | |
| Body-mass index, Kg/M², mean ± standard deviation | 28.6 ± 6.2 |
| Systolic blood pressure, mm Hg, mean ± standard deviation | 110.0 ± 14.9 |
| Diastolic blood pressure, mm Hg, mean ± standard deviation | 65.5 ± 9.2 |
| Jugular venous distension (%) | 34.7% |
| Rales (%) | 12.1% |
| S3 gallop (%) | 32.3% |
| S4 gallop (%) | 8.9% |
| Murmur (%) | 65.3% |
| Hepatojugular reflux (%) | 4.0% |
| Peripheral edema (%) | 29.8% |
| ECG findings | |
| LBBB (%) | 15.0% |
| Paced (%) | 49.0% |
| QRS duration, milliseconds, mean ± standard deviation | 136.5 ± 34.8 |
| Laboratory Values | |
| Blood urea nitrogen, mg/dL, mean ± standard deviation | 30.4 ± 16.2 |
| Creatinine, mg/dL, mean ± standard deviation | 1.48 ± 0.47 |
| Estimated glomerular filtration rate, mL/min/1.73 m², mean ± standard deviation | 61.2 ± 21.7 |
| NT-proBNP, pg/mL, median (IQR) | 1964 (999-3718) |
| IGFBP7, ng/mL, median (IQR) | 89.9 (74.2-117.3) |

NYHA denotes: New York Heart Association; HF denotes: heart failure; ACE denotes: angiotensin converting enzyme; ECG denotes: electrocardiogram; LBBB denotes: left bundle branch block; NT-proBNP denotes: amino-terminal pro-B-type natriuretic peptide; IGFBP7 denotes: insulin-like growth factor-binding protein 7.

IGFBP7 and Echocardiographic Measurements

The following table 2 compares baseline echocardiographic measurements of study participants, divided using the prognostic threshold cut point of 117.8 ng/mL (Cardiac parameters as a function of IGFBP7 concentrations at baseline).

| Parameter | IGFBP7 ≥ 117.8 ng/mL (N = 31) | IGFBP7 < 117.8 ng/mL (N = 93) | P value |
|---|---|---|---|
| A. Left ventricular volumes and function | | | |
| LVEF (%) | 28 [20-35] | 27.0 [20.0-34.5] | 0.67 |
| LVEDVi (mL/m²) | 63.0 [54.0-71.0] | 62.0 [55.0-67.0] | 0.88 |
| LVESVi (mL/m²) | 54.0 [44.0-63.0] | 53.0 [45.5-58.0] | 0.56 |
| LV mass index (g/m²) | 164.3 [123.0-300.0] | 148.5 [98.5-191.0] | 0.21 |
| LVOT velocity (m/sec) | 17.0 [13.0-20.0] | 16.0 [12.0-21.0] | 0.99 |
| B. Left atrial size and volumes | | | |
| LA size, AP, mm | 44.0 [40.0-49.0] | 44.0 [39.0-48.0] | 0.78 |
| LA size, SI, mm | 60.0 [52.0-66.0] | 54.0 [45.6-56.0] | 0.01 |
| LAVi, mL/m² | 32.0 [23.3-48.4] | 25.2 [14.1-36.4] | 0.03 |
| C. Diastolic function and estimates of filling pressure | | | |
| E peak velocity (msec) | 98.5 [79.0-120.8] | 82.0 [61.0-104.0] | 0.005 |
| A peak velocity (msec) | 44.0 [36.0-83.0] | 64.0 [38.5-80.5] | 0.001 |
| Transmitral E/A (msec) | 2.25 [1.1-3.2] | 1.23 [0.86-2.50] | 0.008 |
| E' peak velocity (msec) | 6.6 [4.9-8.4J] | 7.00 [5.1-8.8] | 0.90 |
| E/E' | 15.2 [10.8-20.2] | 10.8 [8.4-15.4] | <0.001 |
| E/E' > 15, % | 51.6% | 23.2% | <0.001 |
| E'/A' | 1.45 [1.0-2.54] | 1.04 [0.67-1.71] | 0.08 |
| PV S peak velocity (msec) | 32.0 [26.0-54.0] | 40.0 [29.8-52.3] | 0.09 |
| PV S deceleration slope | 159.0 [110.0-206.0] | 166.0 [125.0-226.0] | 0.12 |
| PV S deceleration time | 210.0 [183.0-275.0] | 230.0 [190.0-268.8] | 0.08 |
| PV D peak velocity (msec) | 60.0 [47.0-76.0] | 47.5 [39.8-70.2] | 0.03 |
| PV D deceleration slope | 300.0 [217.0-468.0] | 226.0 [147.3-323.0] | 0.009 |
| PV D deceleration time | 210.0 [160.0-260.0] | 220.0 [180.5-271.5] | 0.89 |
| PV S/D ratio | 0.49 [0.38-0.97] | 0.78 [0.51-1.3] | 0.14 |
| D. Right ventricular parameters | | | |
| RVEDD, mm | 41.0 [34.0-44.0] | 38.0 [34.0-43.0] | 0.40 |
| RVESD, mm | 31.0 [26.0-34.0] | 31.0 [26.0-35.0] | 0.99 |
| RVEDV, 4 chamber, mL | 34.5 [25.0-46.8] | 32.0 [26.0-46.5] | 0.84 |
| RVEDA, 4 chamber, mm | 16.5 [14.0-21.0] | 15.5 [13.0-19.75] | 0.78 |
| RVESV, 4 chamber, mL | 18.0 [13.8-30.3] | 18.0 [12.5-25.0] | 0.99 |
| RVESA, 4 chamber, mm | 10.2 [9.0-13.3] | 10.5 [8.0-13.0] | 1.0 |
| RV free wall thickness, mm | 7.0 [5.1-8.0] | 6.0 [5.0-7.0] | 0.82 |
| RV fractional area change (%) | 36.0 [25.5-42.5] | 29.0 [17.0-39.0] | 0.05 |
| RV systolic pressure, mm Hg | 53.0 [44.5-66.5] | 43.5 [36.3-55.0] | 0.006 |
| RV hypokinesis, % | 35.5% | 31.2% | 0.90 |
| RV dilation, % | 45.2% | 24.7% | 0.05 |
| E. Right atrial parameters | | | |
| RA size, inflow, mm | 39.0 [31-44.0] | 38.0 [33.0-44.3] | 0.98 |
| RA size, SI, mm | 54.0 [48.0-60.0] | 46.8 [42.1-54.0] | 0.12 |
| RA size, 4C, mm | 39.0 [23.0-62.0] | 38.2 [33.1-45.0] | 0.94 |

-continued

| Parameter | IGFBP7 ≥ 117.8 ng/mL (N = 31) | IGFBP7 < 117.8 ng/mL (N = 93) | P value |
|---|---|---|---|
| F. Valvular heart disease | | | |
| Aortic regurgitation > mild | 19.4% | 15.1% | 0.56 |
| Mitral regurgitation > mild | 58.1% | 33.3% | 0.001 |
| Tricuspid regurgitation > mild | 35.5% | 12.9% | 0.002 |

LVEF denotes: left ventricular ejection fraction; LVEDVi denotes: left ventricular end diastolic volume index; LVESVi denotes: left ventricular end systolic volume index; LVOT denotes left ventricular outflow tract; LA denotes: left atrium; AP denotes: anterior-posterior; SI denotes: supero-infero; LAVi denotes: left atrial volume index; PV denotes: pulmonary vein; S denotes: systolic; D denotes: diastolic; RVEDD denotes: right ventricular end diastolic diameter; RVESD denotes: right ventricular end systolic diameter; RVEDV denotes: right ventricular end diastolic volume; RVEDA denotes: right ventricular end diastolic area; RVESV denotes: right ventricular end systolic volume; RVESA denotes: right ventricular end systolic area; RA denotes: right atrium; 4C denotes: four chamber.

While no clear associations were present between IGFBP7 concentrations and median values of LV size and function, numerous other significant associations were found, particularly between IGFBP7 concentrations and measures that describe abnormalities of diastolic function. For example, those with higher IGFBP7 concentrations were more likely to have higher LAVi (32.0 [IQR=23.3-48.4] versus 25.2 [14.1-36.4] mL/m$^2$; P=0.03); subjects with higher IGFBP7 concentrations were also more likely to have significant associations between elevated IGFBP7 and higher transmitral Doppler E wave velocity, lower transmitral Doppler A wave velocity, and corresponding direct association with higher E/A ratio. In a similar fashion, using the mitral inflow E velocity to tissue Doppler E' velocity ratio (E/E'), higher values were found in those with elevated IGFBP7 (15.2 [10.8-20.2] versus 10.8 [8.4-15.4]; P<0.001) and more patients with high IGFBP7 had an E/E'>15 (51.6% versus 23.2%; P<0.001). Furthermore, patients with elevated IGFBP7 were significantly more likely to have higher RVSP (53.0 [44.5-66.5] mmHg versus 43.5 [36.3-55.0] mm Hg; P=0.006), along with a more dilated RV. Moreover, a significantly higher percentage of patients in the high IGFBP7 group had more than mild mitral regurgitation (58.1% versus 33.3%; P=0.001) or tricuspid regurgitation (35.5% versus 12.9%; P=0.002).

We then focused on correlations between ln-IGFBP7 and various echocardiographic parameters, detailed in the following table 3.

TABLE 3

Univariate correlation and multivariable linear regression analyses of IGFBP7 concentrations and baseline echocardiographic parameters.

| Characteristic | Univariate | | Multivariable | |
|---|---|---|---|---|
| | ρ | P | β | P |
| LV parameters | | | | |
| LVEF | 0.018 | 0.08 | | |
| LVESVi | 0.087 | 0.59 | | |
| LVEDVi | 0.090 | 0.58 | | |
| LV mass | 0.120 | 0.18 | | |
| IV septal thickness | 0.116 | 0.20 | | |
| Posterior wall thickness | 0.034 | 0.71 | | |
| LVOT velocity | 0.128 | 0.16 | | |
| LA parameters | | | | |
| Left atrial size, AP | 0.265 | 0.003 | | |
| Left atrial size, SI | 0.231 | 0.01 | | |
| Left atrial volume index | 0.237 | 0.008 | 0.386 | 0.01 |

TABLE 3-continued

Univariate correlation and multivariable linear regression analyses of IGFBP7 concentrations and baseline echocardiographic parameters.

| Characteristic | Univariate | | Multivariable | |
|---|---|---|---|---|
| | ρ | P | β | P |
| RV parameters | | | | |
| RVEDD | 0.202 | 0.03 | | |
| RVESD | 0.009 | 0.90 | | |
| RV free wall thickness | 0.222 | 0.02 | | |
| RV fractional area change | 0.240 | 0.009 | | |
| RV systolic pressure | 0.316 | 0.001 | 0.317 | 0.001 |
| RA parameters | | | | |
| Right atrial size, inflow | 0.029 | 0.76 | | |
| Right atrial size, SI | 0.287 | <0.001 | 0.584 | <0.001 |
| LV diastolic indices, transmitral flow | | | | |
| E peak velocity | 0.230 | 0.01 | −0.592 | <0.001 |
| A peak velocity | −0.208 | 0.03 | | |
| E/A | 0.304 | 0.001 | 0.601 | 0.005 |
| LV diastolic indices, pulmonary vein flow | | | | |
| S wave peak velocity | −0.147 | 0.14 | | |
| S wave deceleration slope | −0.120 | 0.24 | | |
| S wave deceleration time | 0.120 | 0.24 | 0.437 | <0.001 |
| D wave peak velocity | 0.411 | <0.001 | | |
| D wave deceleration slope | 0.316 | 0.001 | | |
| D wave deceleration time | −0.048 | 0.64 | | |
| S/D | −0.173 | 0.09 | | |
| LV diastolic indices, tissue Doppler | | | | |
| tD E peak velocity | −0.01 | 0.92 | | |
| tD A peak velocity | 0.287 | 0.003 | | |
| tD E/E' | 0.257 | 0.005 | 0.222 | 0.02 |
| tD E'/A' | −0.364 | 0.005 | −0.759 | <0.001 |

LV denotes: left ventricle; LVEF denotes: left ventricular ejection fraction; LVESVi denotes: left ventricular end systolic volume index; LVEDVi denotes: left ventricular end diastolic volume index; IV denotes: intraventricular; LVOT denotes: left ventricular outflow tract; LA denotes: left atrium; AP denotes: anterior-posterior; SI denotes: supero-infero; RV denotes: right ventricle; RVEDD denotes: right ventricular end diastolic diameter; RVESD denotes: right ventricular end systolic diameter; RA denotes: right atrium; S denotes: systolic; D denotes: diastolic; tD denotes: tissue Doppler.

In univariate analyses, we detected numerous significant correlations between ln-IGFBP7 concentrations and cardiac structure and function, such as atrial size and RV pressures. Furthermore, we discovered extensive significant correlations with diastolic parameters, such as transmitral Doppler E and A waves (as well as their ratio), pulmonary vein Doppler velocity and slope of the D wave (as well as marginal correlation with pulmonary vein S/D ratio), and variables in tissue Doppler imaging, including E/E'. FIG. 3 shows scatter plots of transmitral Doppler E/A, E/E', pulmonary vein S/D ratio, LAVi, and RVSP in relation to IGFBP7 concentrations.

Subsequently, in a multivariable adjusted linear regression that took into account clinical and echocardiographic variables (table 3), we identified several variables that were uniquely predictive of ln-IGFBP7 concentrations. Consistent with our previous findings, this once again recapitulated a phenotype of abnormal diastolic function. Independent predictors included left atrial volume index, right atrial size in supero-infero dimensions, right ventricular systolic pressure, as well as numerous diastolic parameters derived from Doppler imaging, including A wave velocity, E/A ratio, S wave deceleration time, E/E', and E'/A'. Additionally, clinical variables factoring into the multivariable model were age ($\beta$=0.271; P=0.004), ischemic cause of HF ($\beta$=0.270; P=0.003) and the presence of hepatomegaly on examination ($\beta$=0.487; P<0.001), all of which positively correlated with IGFBP7 levels (data not shown). Baseline NT-proBNP values were correlated to IGFBP7 ($\rho$=0.378; P<0.001) but in adjusted analyses, NT-proBNP was only a weak independent predictor of IGFBP7 concentrations ($\beta$=0.107; P=0.07).

Figure 1A:
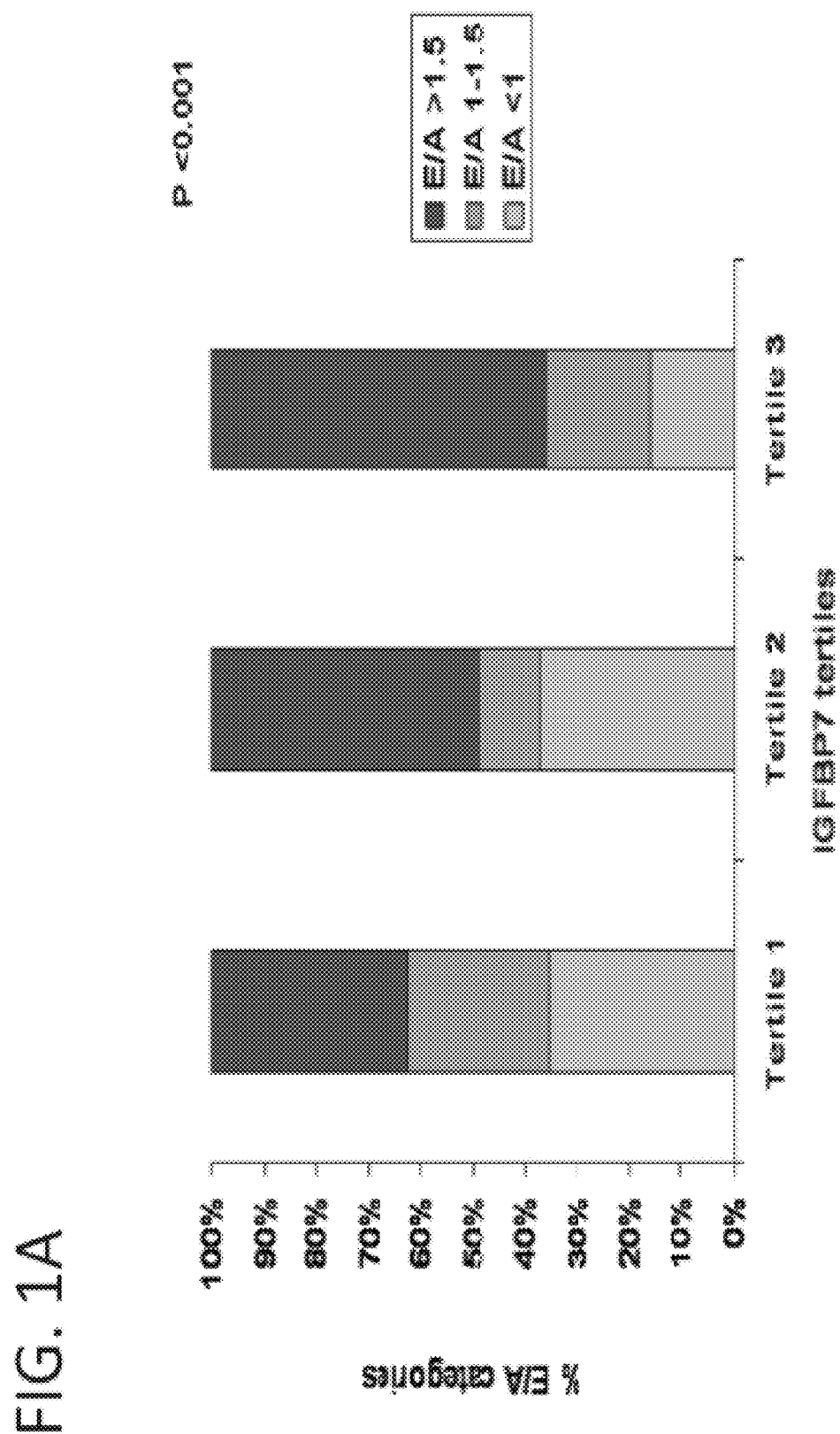
FIG. 1A: Diastolic parameters shown in tertiles of IGFBP7 for Transmitral Doppler flow.
Figure 1B:
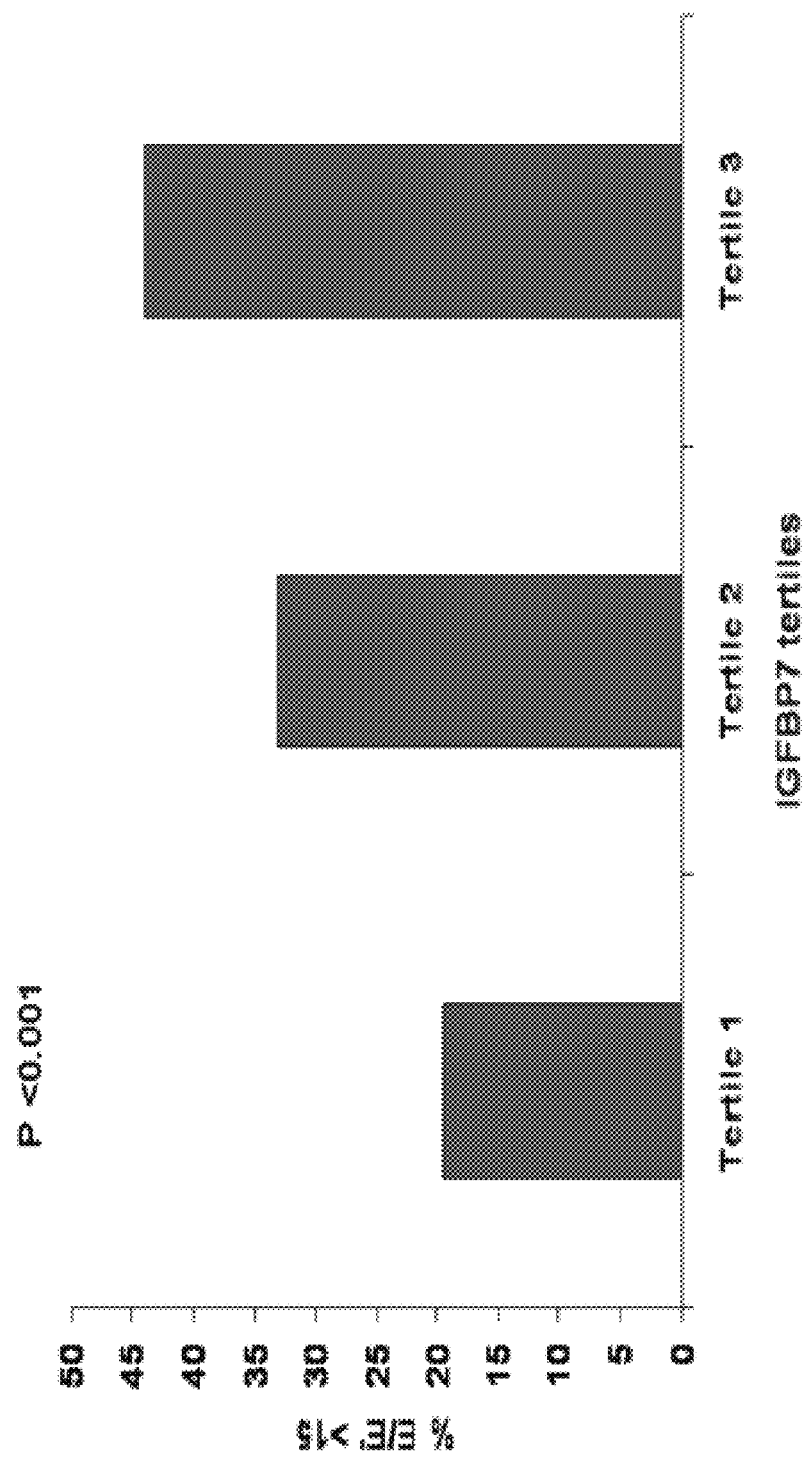
FIG. 1B: Diastolic parameters shown in tertiles of IGFBP7 for E/E'>15.
Figure 1D:
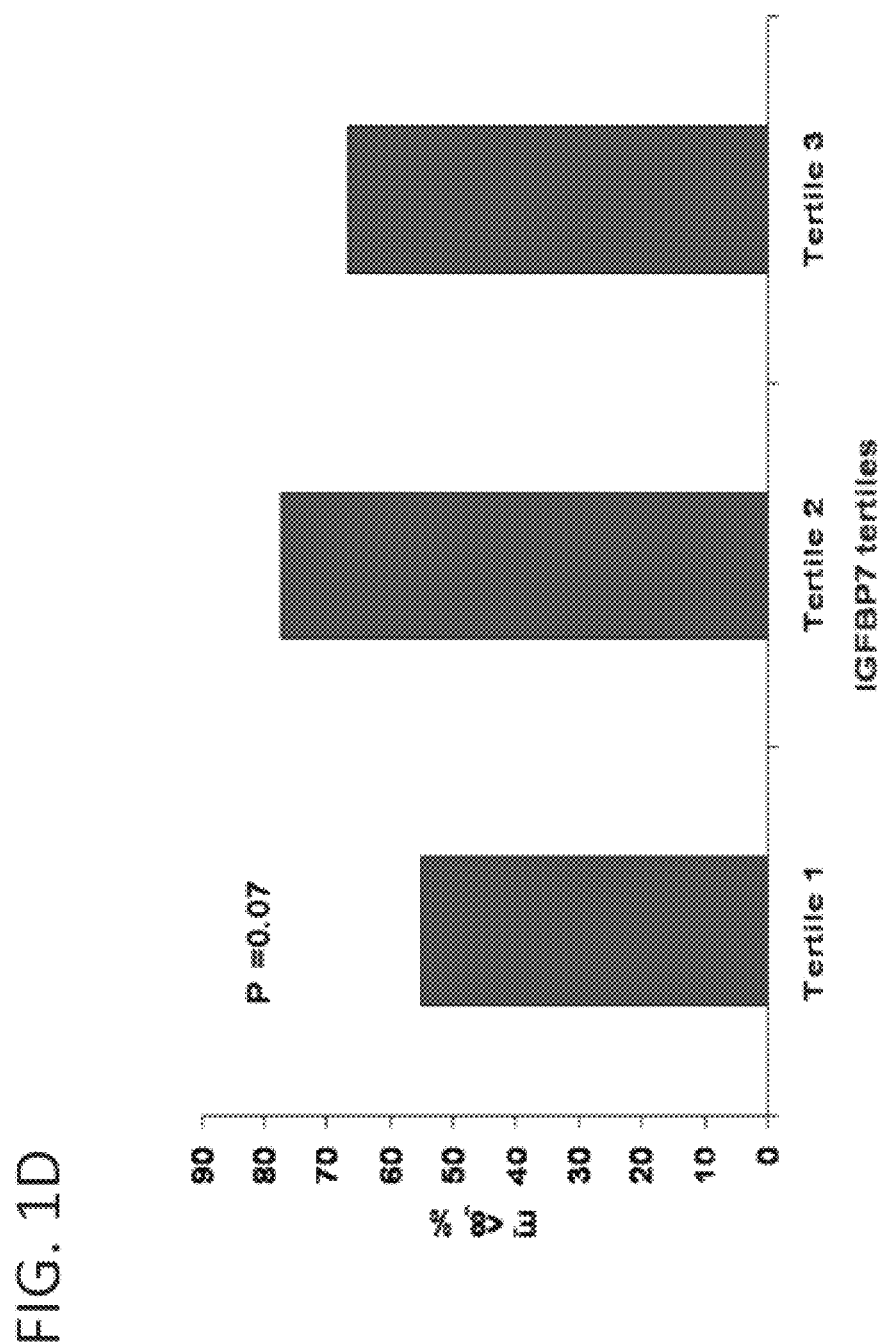
FIG. 1D: Diastolic parameters shown in tertiles of IGFBP7 for, and E'<8 cm/sec.

We next considered subjects in terms of IGFBP7 tertiles, and depicted various diastolic parameters in this manner. As shown in FIG. 1A, the percentage of patients with transmitral Doppler E/A ratios (categorized by groups of <1, 1.0-1.5, or >1.5) was directly associated; furthermore, the highest percentage of patients with E/A>1.5 was present in the highest tertile of IGFBP7 (p<0.001). In a similar manner, FIGS. 1B and 1C detail associations between IGFBP7 tertiles and percentages of patients with E/E'>15 and LAVi>28 mL/m². In contrast to these direct associations, we found the association between E' and IGFBP7 concentrations appeared to be a non-significant trend (FIG. 1D).

Changes in Diastolic Parameters as a Function of IGFBP7 Concentrations Over Time As noted, study participants made a total of more than 880 office visits during the study duration. Of these, 108 had matched baseline and final visit echocardiographic examinations. This provided an ideal opportunity to examine secular trends in IGFBP7 concentrations and changes in diastolic parameters linked to the biomarker in baseline conditions.

On average through the 10 months of follow up, study participants spent 78% of their time with an IGFBP7<117.8 ng/mL. We examined this "time spent in response" as a function of change in diastolic function parameters from baseline to final echocardiogram. These results are shown in FIG. 2. In those with E/A ratios of <1.5 at both baseline and final assessment, a higher percentage of time was spent with IGFBP7 levels below 117.8 ng/mL, when compared to those with an initially normal E/A ratio who rose to >1.5 at follow up (86% vs. 42%, P<0.001). Similar findings were seen with RVSP, the S/D ratio of pulmonary venous flow, and LAVi. In each case, those with worsening diastolic function were more likely to have less time spent with IGFBP7 levels <117.8 ng/mL over serial measurement.

Outcomes

In models adjusted for relevant epidemiologic variables predictive of risk in chronic HF (including echocardiographic parameters of diastolic dysfunction), time spent with an IGFBP7 concentration <117.8 ng/mL was an independent predictor of event free survival (HR=0.83 per 10% time in response increase; 95% CI=0.73-0.95, P=0.006). Notably, with inclusion of IGFBP7 results to the models, measures of diastolic function were not significant in predicting risk.

DISCUSSION

BNP and NT-proBNP have been extensively investigated for the diagnosis, prognosis, and management of HF (Januzzi et al., see above, Januzzi et al., The n-terminal pro-bnp investigation of dyspnea in the emergency department (pride) study, *Am J Cardiol.* 2005; 95:948-954, Januzzi et al., Utility of amino-terminal pro-brain natriuretic peptide testing for prediction of 1-year mortality in patients with dyspnea treated in the emergency department, *Arch Intern Med.* 2006; 166:315-320, Maisel et al., Rapid measurement of b-type natriuretic peptide in the emergency diagnosis of heart failure, *N Engl J Med.* 2002; 347:161-167). It has also been suggested that they may be useful to detect diastolic dysfunction (Tschope et al., see above, Weiner et al., see above, Yu et al., see above). However, concentrations of both natriuretic peptides are affected by many other variables of cardiac structure and function as well as other cardiopulmonary disorders (Daniels et al., see above), which may complicate interpretation of these values. In this study of subjects with ambulatory chronic HF due to LVSD, we present the use of IGFBP7 (previously linked to hypertrophy, angiogenesis and cell survival) as a surrogate marker for diastolic dysfunction and prognosis.

We found study subjects with elevated levels of IGFBP7 were more likely to have broad-based evidence of diastolic dysfunction on echocardiography, with abnormalities in transmitral Doppler flow, tissue Doppler imaging, atrial size, and RV pressures, all of which are commonly used measurements in the complex echocardiographic determination of diastolic dysfunction (Nagueh et al., see above). As borne out in multiple analyses, a trend of increasing severity of diastolic abnormalities was seen with higher IGFBP7 levels. This implies that in addition to the association of IGFBP7 to the presence of diastolic abnormalities, concentrations of IGFBP7 may also give insight into the degree of dysfunction. Lastly, and perhaps most curiously, secular trends in IGFBP7 concentrations were associated with the development of worsened diastolic function over time and replaced echocardiographic measures in survival models. To our knowledge, this is the first published report linking IGFBP7 to the presence and severity of many commonly used measures of diastolic function and raises the intriguing suggestion that this biomarker may be utilized as a surrogate marker for the presence, severity, and risk associated with diastolic dysfunction.

IGFBP7, which is also known as mac25 and IGFBP-related protein 1 (IGFBP-rP1) belongs to the IGFBP family, sharing a common motif at the amino terminus of the protein (Hwa et al., The insulin-like growth factor-binding protein (igfbp) superfamily, *Endocr Rev.* 1999; 20:761-787, Oh et al., Synthesis and characterization of insulin-like growth factor-binding protein (igfbp)-7, Recombinant human mac25 protein specifically binds igf-i and -ii, *J Biol Chem.* 1996; 271:30322-30325). The IGF axis plays important roles in the growth and proliferation of mammalian cells. This pathway is comprised of the insulin-like growth factors and insulin, and their binding to the cognate receptors. IGFBP7 is a secreted protein that competes with IGF-1 and inhibits its binding to the IGF receptor (Hwa et al., see above, Chen et al., Insulin-like growth factor-binding protein-7 functions as a potential tumor suppressor in hepatocellular carcinoma, *Clin Cancer Res.* 2011; 17:6693-6701). This in turn suppresses downstream IGF receptor signaling, including PI3K/Akt and associated cell growth and proliferation (Evdokimova et al., Igfbp7 binds to the igf-1 receptor and blocks its activation by insulin-like growth factors, Sci Signal, 2012; 5:ra92). Thus IGFBP7 has been implicated as a tumor suppressor, and prolonged exposure in tumor cells leads to decreased protein synthesis and cell growth, and enhanced apoptosis (Chen et al., see above, Evdokimova et al., see above). This protein has also been investigated in acute kidney injury where it has been proposed that IGFBP7 leads to increased expression of p53 and p21; cell cycle arrest at phase $G_1$ follows, which may prevent division of renal epithelial cells with damaged DNA from ischemia or sepsis (Kashani et al., Discovery and validation of cell cycle arrest biomarkers in human acute kidney injury, Crit care, 2013; 17:R25).

IGFBP7 is highly expressed in the vasculature. Recent work has localized IGFBP7 to the Weibel-Palade bodies (storage organelles) in the endothelial cells which deliver inflammatory and hemostatic mediators to the vascular lumen through exocytosis (van Breevoort et al., see above). IGFBP7 appears to be able to regulate angiogenesis in conjunction with von Willebrand factor and other factors in the storage organelles van Breevoort et al., see above).

The pathophysiology of diastolic abnormalities in HF involves cellular hypertrophy, with subsequent cell loss through apoptosis, and increased fibrosis and diastolic stiffness (Ouzounian et al., Diastolic heart failure: Mechanisms and controversies, *Nat Clin Pract Cardiovasc Med.* 2008; 5:375-386). Based on these data, it can be hypothesized that elevated concentrations of IGFBP7 may be protective by inhibiting myocyte hypertrophy and fibroblast division, thereby preventing further deposition of collagen, an important contributor to diastolic stiffness of the ventricular myocardium (Zile et al., New concepts in diastolic dysfunction and diastolic heart failure: Part ii: Causal mechanisms and treatment, *Circulation,* 2002; 105:1503-1508). However, excessive IGFBP7 activation may lead to blocked IGF-1 and insulin signaling, leading to accelerated apoptosis and cell death.

Our data linking trends of IGFBP7 over time with the onset of worsening diastolic indices is of noteworthy emphasis. Similarly, inclusion of the time spent <117.8 ng/mL also displaced these variables of diastolic abnormality in models for event free survival. It is enticing to consider that IGFBP7 may represent a mediator of, or response to, factors that result in the worsened ventricular compliance that leads to the elevated filling pressures reflected in the abnormal measures of diastolic function (and the attendant risk that follows). That we have previously shown IGFBP7 to be prognostically additive to NT-proBNP-itself linked with many other meaningful cardiac abnormalities (Tschope et al., see above, Weiner et al., see above) not predictive of IGFBP7—supports this suggestion. While Tschipe et al have shown abnormalities in NT-proBNP to be associated with the presence and severity of diastolic dysfunction in patients with preserved EF (Tschope et al., see above), this link is considerably less robust than that found between IGFBP7 and abnormal diastology in this study, suggesting the combination of NT-proBNP and IGFBP7 provide a broader-based biological depiction of the underlying cardiac structure and function abnormalities present in HF.

While our study is the first published showing the link between IGFBP7 and diastolic dysfunction in detail, there are some limitations. Firstly, the sample size is limited, but our results are internally consistent through numerous analyses. Secondly, our study only included patients with LVSD; as most patients with LVSD have a component of diastolic dysfunction (Yancy et al., see above, Bursi et al., Systolic and diastolic heart failure in the community, *JAMA,* 2006; 296:2209-2216), our results do not necessarily apply to those with HF with preserved EF (HFpEF). However, the severity of diastolic dysfunction in our subjects varies widely and we have shown the association of IGFBP7 across grades of diastolic dysfunction. Thirdly, we are using multiple echocardiographic findings as surrogate measures for diastolic dysfunction. As pointed out by Maurer and colleagues, abnormal diastolic Doppler echocardiographic patterns may not be sufficient to conclude abnormal myocardial diastolic properties are present (Maurer et al., Diastolic dysfunction: Can it be diagnosed by Doppler echocardiography? *J Am Coll Cardiol.* 2004; 44:1543-1549). Nonetheless, in a population of patients with HFrEF, it is generally accepted such measures do reflect a mixture of elevated filling pressures and impaired relaxation properties of the myocardium; the lack of strong correlation to NT-proBNP suggests concentrations of IGFBP7 are not entirely due to volume status.

SUMMARY/CONCLUSION 124 patients with ambulatory HF due to left ventricular systolic dysfunction (LVSD) and baseline detailed two-dimensional echocardiographic examinations were followed for a mean of 10 months. IGFBP7 was measured serially at each office visit. Patients with elevated baseline IGFBP7 concentrations were more likely to have abnormalities of parameters describing diastolic function, such as left atrial volume index (LAVi) 32.0 mL/m2 versus 25.2 mL/m2 (P=0.03), transmitral E/A 2.25 versus 1.23 (P=0.008), E/E' 15.2 versus 10.8 (P<0.001), and right ventricular systolic pressure (RVSP) 53.0 mmHg versus 43.5 mmHg (P=0.006). Additionally, IGFBP7 was correlated with diastolic parameters such as LAVi ($\rho$=0.237, P=0.008), transmitral E/A ($\rho$=0.304, P=0.001), E/E' ($\rho$=0.257, P=0.005), and RVSP ($\rho$=0.316, P=0.001). Furthermore, these parameters were found to be independent predictors of IGFBP7 in adjusted analysis. Among those subjects with baseline and final echocardiograms (108 patients), the more time spent with elevated IGFBP7 values in serial measurement was associated with worsening diastolic function, and increasing LAVi or RVSP. IGFBP7 concentrations were predictive of an increased risk of CV events independent of echocardiographic measures of diastolic dysfunction.

IGFPB7 is a novel biomarker that is strongly associated with diastolic dysfunction and prognosis in patients with HF due to LVSD. Biological mechanisms that explain the link between this unique biomarker and diastolic function remain intriguing and warrant further investigation. Further studies should be conducted to validate the role of IGFBP7 in heart failure with preserved ejection fraction, and to determine if IGFBP7 is a potential contributor to diastolic heart failure progression.

Example 2: TIME CHF Study Patients

Samples were extracted from the TIME CHF Trial of Intensified versus standard Medical therapy in Elderly patients with Chronic Heart Failure. This cohort includes patients in NYHA class ≥II under therapy, having experienced a HF hospitalization within the last year or having had a LVEF of ≤45% or having had elevated NT-proBNP levels (i.e. 400 pg/ml in patients <75 years, NT-proBNP <800 pg/ml in patients aged 75 years or older) and were ≥60 years of age (no upper age limit). (Pfisterer M, Buser P, Rickli H, Gutmann M, Erne P, Rickenbacher P, et al. Bnpguided vs symptom-guided heart failure therapy The trial of intensified vs standard medical therapy in elderly patients with congestive heart failure (time-chf) randomized trial. JAMA: the journal of the American Medical Association 2009, 301: 383).

Available samples of the TIME CHF study were extracted for biomarker analyses of associations to systolic (LVEF) and diastolic parameters (E/A, E/E', LA diameter, LA squared).

All samples had systolic parameters, but only a subset was in addition characterized by diastolic parameters. Conventional cardiac markers on automated Roche analyzers were measured in a larger sample subset, while innovative markers available were tested in a smaller sample subset.

Example 2.1

Example from TIME-CHF study: Conventional markers (NT-proBNP Elecsys, cTNThs Elecsys, GDF15 Elecsys, uric acid Roche Cobas) have been determined in 622, 561, 561 and 512 samples respectively. All samples were derived from patients with Echocardiopraphic data of LVEF (left ventricular ejection fraction). E/E' ratio was available for 228 patients. E/A ratiowas avail-able for 314 patients. Wall thickness was available for 456 patients.

New markers (Mimecan, Endostatin, IGFBP7, Osteopontin) have been determined in 197, 198, 197, 184 samples, respectively. All samples were taken from patients with available LVEF data. E, A and E/A data were available for 106 patients. Tissue Doppler was available for 77 patients. Wall thickness (septum diameter) was available for 142 patients.

$p=0.003$), LA squared (0.14, p:0.003, LA diameter (0.13, p:0.007). As shown in example 1) NT-proBNP is not suited to discriminate diastolic dysfunction versus systolic dysfunction.

IGFBP-7 was found not to correlate either to LVEF (systolic (dys)-function) or to septum diameter. In contrast IGFBP-7 was found to be the new marker candidate with most significant correlations to several parameters of diastolic (dys-) function. Data evaluation (table 4) shows, that the strongest correlations of IGFBP-7 were found with E/A and LA parameters. E/A correlations of IGFBP-7 were stronger than E/A correlations of all conventional markers under investigation including NT-proBNP and cTNThs (taking different sample sizes into account). As shown in example 1) IGFBP7 is very well suited to discriminate multiple parameters of diastolic dysfunction (E/A: 0.2, p:0.04, LA squared: 0.15, p:0.08) versus systolic dysfunction (LVEF: −0.01, p:0.87) and versus wall thickness (septum diameter: 0.07, p:0.43). IGFBP7 shows most specific relations to multiple diastolic parameters versus all new and conventional markers tested. IGFBP7 is well suited to detect diastolic dysfunction alone or in combination with other markers. Preferred are combinations of IGFBP7 with markers that show strong correlations to E/E'(cTNThs, NT-proBNP, Mimecan, Endostatin).

As shown in table 4, a combination of IGFBP-7 with NT-proBNP is found to be useful to assess various complementary parameters of diastolic dysfunction.

TABLE 4

Correlations between IGFB7, cTNThs, NTproBNP, GDF15, uric acid, endostatin, mimecan and osteopontin and systolic and diastolic parameters

|  | Endostatin (n = 198) | Mimecan (n = 197) | IGFBP7 (n = 197) | Osteopontin (n = 184) | NT-proBNP (n = 622) | cTnThs (n = 561) | GDF15 (n = 561) | Uric acid (n = 512) |
|---|---|---|---|---|---|---|---|---|
| LVEF | −0.09 | 0.10 | −0.01 | 0.13 | −0.24** | −0.07 | 0.07 | −0.02 |
|  | P = 0.23 | P = 0.17 | P = 0.87 | P = 0.08 | P < .001 | P = .10 | P = .13 | P = .74 |
| E | 0.13 | 0.12 | 0.19* | 0.14 | 0.10* | 0.07 | 0.15** | 0.13** |
|  | P = 0.10 | P = 0.13 | P = 0.02 | P = 0.08 | P = .02 | P = .19 | P = .001 | P = .008 |
| E/A | 0.03 | 0.03 | 0.20* | −0.03 | 0.17** | 0.01 | 0.10 | 0.13* |
|  | P = 0.76 | P = 0.73 | P = 0.04 | P = 0.80 | P = .003 | P = .86 | P = .10 | P = .046 |
| E' | 0.13 | −0.03 | 0.20 | 0.11 | −.17** | −.24** | .008 | −0.02 |
|  | P = 0.27 | P = 0.79 | P = 0.08 | P = 0.34 | P = .007 | P < .001 | P = .91 | P = .73 |
| E/E' | 0.11 | 0.18 | 0.05 | 0.05 | 0.16* | 0.22** | 0.05 | −0.01 |
|  | P = 0.36 | P = 0.15 | P = 0.70 | P = 0.69 | P = .02 | P = .002 | P = .44 | P = .89 |
| LA diameter | 0.08 | 0.09 | 0.13 | 0.10 | .13** | −0.01 | 0.14** | 0.24** |
|  | P = 0.32 | P = 0.29 | P = 0.12 | P = 0.26 | P = .007 | P = .83 | P = .004 | P < .001 |
| LA squared | 0.05 | 0.05 | 0.15 | 0.11 | 0.14** | −0.04 | .08 | 0.19** |
|  | P = 0.52 | P = 0.54 | P = 0.08 | P = 0.19 | P = .003 | P = .39 | P = .12 | P < .001 |
| Septum diameter | −0.05 | −0.04 | 0.07 | 0.22** | −0.014 | 0.04 | .05 | −0.04 |
|  | P = 0.54 | P = 0.68 | P = 0.43 | P = 0.01 | P = .76 | P = .39 | P = .30 | P = .46 |

*p < 0.05
**p < 0.01

Data evaluation in table 4 showed that NT-proBNP was the only marker found to correlate significantly (p<0.01) with systolic (dys)-function (LVEF,−0.24, p<0.001). NT-proBNP correlates significantly with diastolic parameters (E/A, E/E', LA parameters). NT-proBNP was found to correlate more significantly with systolic versus diastolic parameters. The strongest correlation of NT-proBNP was found for systolic (dys-) function: LVEF (−0.24, p<0.001) versus diastolic parameters: E/E' (0.16, p 0.02), E/A (0.17, Data evaluation showed that cTNThs was found to correlate best with diastolic (dys-) function parameters (E/E': 0.22, p: 0.002) versus systolic (dys-) function parameters (LVEF: −0.07, p:0.1). A highly significant association of cTNThs to E/E' is found. As demonstrated in table 4 complementary clinical parameters of diastolic function are associated to IGFBP-7 and cTNThs. Thus, a combination of IGFBP-7 and cTNThs is well suited to detect diastolic dysfunction.

Data evaluation showed that correlations of Mimecan with diastolic and systolic parameters did not reach significance. The strongest correlation of Mimecan was found with E/E' (0.18, p:0.15). Mimecan may be suited to complement IGFBP7 in the detection of diastolic dysfunction.

samples were derived from patients with preserved ejection fraction.

New markers (Mimecan, Endostatin, IGFBP7, Osteopontin) have been determined in 15-23 patients with preserved ejection fraction.

TABLE 5

Correlations between IGFB7, cTNThs, NTproBNP, GDF15, uric acid, endostatin, Mimecan and osteopontin and systolic and diastolic parameters in HFpEF patients (LVEF >= 50%)

|  | Endostatin | Mimecan | IGFBP7 | Osteopontin | NT-proBNP (n = 112) | cTnThs (n = 99) | GDF15 (n = 100) | Uric acid (n = 95) |
|---|---|---|---|---|---|---|---|---|
| LVEF | 0.06 | −0.10 | −0.07 | 0.14 | −0.23* | −0.04 | 0.11 | −0.05 |
|  | P = 0.80 | P = 0.65 | P = 0.77 | P = 0.53 | P = .02 | P = .69 | P = .29 | P = .65 |
| E | 0.37 | 0.47 | 0.55 | 0.27 | 0.04 | 0.06 | 0.08 | 0.17 |
|  | P = 0.10 | P = 0.03 | P = 0.01 | P = 0.25 | P = .72 | P = .58 | P = .49 | P = .14 |
| E/A | 0.38 | 0.01 | 0.76 | 0.03 | 0.02 | 0.20 | −0.13 | 0.01 |
|  | P = 0.17 | P = 0.96 | P = 0.001 | P = 0.93 | P = .88 | P = .19 | P = .39 | P = .94 |
| E' | 0.08 | −0.007 | 0.52 | −0.15 | −0.04 | −0.35 | 0.14 | 0.09 |
|  | P = 0.78 | P = 0.98 | P = 0.045 | P = 0.60 | P = .79 | P = .01 | P = .35 | P = .52 |
| E/E' | 0.31 | 0.26 | −0.08 | 0.49 | 0.25 | 0.32 | 0.008 | −0.06 |
|  | P = 0.25 | P = 0.36 | P = 0.79 | P = 0.06 | P = .07 | P = .02 | P = .96 | P = .70 |
| LA diameter | 0.29 | 0.23 | 0.17 | 0.17 | 0.16 | 0.02 | 0.18 | 0.31 |
|  | P = 0.20 | P = 0.32 | P = 0.45 | P = 0.47 | P = .14 | P = .84 | P = .11 | P = .007 |
| LA squared | 0.41 | −0.12 | 0.44 | 0.22 | 0.03 | 0.03 | 0.12 | 0.26 |
|  | P = 0.06 | P = 0.60 | P = 0.04 | P = 0.35 | P = .76 | P = .78 | P = .30 | P = .02 |
| Septum diameter | 0.29 | −0.33 | −0.06 | 0.12 | 0.10 | 0.17 | 0.05 | 0.07 |
|  | P = 0.20 | P = 0.14 | P = 0.79 | P = 0.60 | P = .37 | P = .14 | P = 0.69 | P = .58 |

Osteopontin was found to associate to both systolic (LVEF: 0.13, p: 0.08) and diastolic parameters (E:0.14, p:0.08), as well as to wall thickness (septum diameter: 0.22, p:0.01). Combination of IGFBP7 with Osteopontin may be useful to assess complementary information.

Data evaluation showed that correlations of Endostatin with diastolic and systolic parameters did not reach significance. Endostatin correlates to E/E'. IGFBP7 is well suited to detect diastolic dysfunction alone or in combination with other markers. Preferred are combinations of IGFBP7 with markers that show strong correlations to E/E'(cTNThs, NT-proBNP, Mimecan, Endostatin). The combination of IGFBP-7 with Endostatin may be useful to associate to various diastolic parameters.

GDF-15 and uric acid both were found to correlate better with diastolic versus systolic parameters.

Correlations of GDF15 to E and LA diameter reached significance.

Correlations of uric acid to E/A, LA diameter and LA squared reached significance.

A combination of IGFBP-7 and cTNThs and/or GDF15 and/or uric acid was found to be useful to assess multiple parameters of diastolic dysfunction.

Preferred combinations for Example 2.1 (in this order)
PRIO1→IGFBP7+cTNThs
PRIO2→IGFBP7+NT-proBNP
PRIO3→IGFBP7+Mimecan
PRIO4→IGFBP7+uric acid
PRIO5→IGFBP7+GDF15
PRIO6→IGFBP7+endostatin Example 2.2: Example from TIME-CHF Study Only patients with preserved ejection fraction (HFpEP) were selected in this analysis.

Conventional markers (NT-proBNP Elecsys, cTNThs Elecsys, GDF15 Elecsys, uric acid Roche Cobas) have been determined in 112, 99, 100 and 95 samples respectively. All Data evaluation (Table5) showed that NT-proBNP relates equally well with LVEF and with E/E', slightly more significant with systolic function in patients with preserved ejection fraction. Thus NT-proBNP is not suited to discriminate diastolic versus systolic dysfunction. A combination of NT-proBNP with IGFBP7 may be useful to assess multiple parameters of diastolic dysfunction.

cTNThs showed no apparent relation to LVEF (−0.04, p:0.69), but was found to be correlated significant with diastolic function (E/E': 0.32, p:0.02). Thus a combination of cTNThs with IGFBP7 may be useful to assess multiple parameters of diastolic dysfunction.

IGFBP7 was found to have a very strong and highly significant correlation to diastolic parameters (E/A: 0.76, p:0.001; LA squared 0.44, p: 0.04) as shown in table 5. IGFBP7 showed best relation to multiple diastolic parameters versus all new and conventional markers tested and is well suited to detect diastolic dysfunction alone or in combination with other markers. Preferred are combinations of IGFBP7 with markers that show strong correlations to E/E'(Osteopontin, cTNThs, NT-proBNP, Endostatin, Mimecan).

Data evaluation in table 5 showed strong correlations of Osteopontin with E/E' (0.49, p:0.06) in patients with preserved ejection fraction. Thus Osteopontin may be useful to complement IGFBP7 in the assessment of diastolic function. A combination of IGFBP7 with Osteopontin is preferred to detect diastolic dysfunction.

Data evaluation in table 5 showed strongest correlations of Endostatin with E/E' and LA parameters.

Endostatin and uric acid were shown to have significant associations to LA parameters complementary to the associations of IGFBP7 to assess diastolic function. The combination of IGFBP-7 with Endostatin and/or uric acid may be useful to associate to various diastolic parameters.

Mimecan showed significant correlations with E. The combination of Mimecan and IGFBP7 may be useful to assess diastolic dysfunction.

Data evaluation showed that GDF15 correlations to systolic and diastolic function parameters did not reach significance.

In HFpEF patients best combinations (with IGFBP7) are:
PRIO1: Osteopontin
PRIO2: cTNThs
PRIO3: NT-proBNP
PRIO4: Endostatin
PRIO5: Mimecan
PRIO6: uric acid
PRIO7: GDF15.

The invention claimed is:

1. A method for monitoring diastolic function and/or at least one parameter of diastolic function, said method comprising the steps of
   a) measuring the level of the biomarker IGFBP7 (Insulin like growth factor binding protein 7) by immunoassay and, optionally, at least one further biomarker selected from the group consisting of Osteopontin, a cardiac Troponin, a B-type natriuretic peptide (BNP), Endostatin, Mimecan, uric acid, and GDF15 (Growth differentiation factor 15) in first and in second serum or plasma samples from a human patient suffering from heart failure, said patient having a reduced left ventricular ejection fraction (LVEF), wherein said second sample has been obtained after the first sample, and
   b) comparing the level of the biomarker IGFBP7, and optionally the level of said at least one further biomarker measured in the second sample to the level in the first sample,
   wherein the at least one parameter of diastolic function is selected from the group consisting of left atrial size, left atrial superior-inferior diameter, left atrial volume index, E peak velocity, A peak velocity, transmitral E/A ratio, mitral inflow E velocity to tissue Doppler E' velocity ratio, E'/A' ratio, pulmonary vein systolic peak velocity, pulmonary vein diastolic peak velocity, pulmonary vein systolic/diastolic ratio, increased right ventricular area, right ventricular systolic pressure (RVSP), right ventricular dilation, right atrium size, the right atrial superior-inferior diameter, mitral regurgitation and tricuspid regurgitation;
   wherein the second sample is obtained at least three months after the first sample.

2. The method according to claim 1, wherein the patient suffers from heart failure stage C or D according to the ACC/AHA classification, and/or from heart failure NYHA class III or IV according to the NYHA classification.

3. The method according to claim 1, wherein the patient has a LVEF of less than 50%.

4. The method of claim 1, wherein the patient has left ventricular hypertrophy.

5. The method of claim 1, wherein the patient suffers from heart failure due left ventricular systolic dysfunction.

6. The method of claim 1 wherein the BNP is N-terminal pro B-type natriuretic peptide (NT-proBNP).

7. The method according to claim 3, wherein the patient has a LVEF of less than 40%.

8. The method of claim 4, wherein the patient has a left ventricular mass index of larger than 126 $g/m^2$.

9. The method of claim 1 wherein at least one further biomarker selected from the group consisting of Osteopontin, a cardiac Troponin, a B-type natriuretic peptide (BNP), Endostatin, Mimecan, uric acid, and GDF15 (Growth differentiation factor 15) is measured in step a).

10. The method of claim 2, wherein the level of IGFBP7 and, optionally, of the at least one further biomarker in the second sample, is increased as compared to the level in the first sample, indicative of deterioration of diastolic function and/or of deterioration of the at least one parameter of diastolic function, and the method further comprises administering a therapy to the patient, the therapy selected from the group consisting of Spironolactone, Sildenafil and Anakinra.

* * * * *